United States Patent
Lewinsohn et al.

(10) Patent No.: US 10,457,682 B2
(45) Date of Patent: Oct. 29, 2019

(54) SMALL MOLECULES THAT BIND MR1

(71) Applicants: OREGON HEALTH & SCIENCE UNIVERSITY, Portland, OR (US); THE UNITED STATES OF AMERICA AS REPRESENTED BY THE DEPARTMENT OF VETERANS AFFAIRS, Washington, DC (US)

(72) Inventors: David Lewinsohn, Portland, OR (US); Melanie Harriff, Portland, OR (US); Aaron Nilsen, Portland, OR (US); Haihong Jin, Portland, OR (US); Erin Adams, Chicago, IL (US); Cara Froyd, Chicago, IL (US); Curtis McMurtrey, Norman, OK (US); William Hildebrand, Norman, OK (US)

( * ) Notice: Subject to any disclaimer, the term of this patent is extended or adjusted under 35 U.S.C. 154(b) by 0 days.

(21) Appl. No.: 15/789,955

(22) Filed: Oct. 20, 2017

(65) Prior Publication Data

US 2018/0273536 A1 Sep. 27, 2018

Related U.S. Application Data

(60) Provisional application No. 62/411,208, filed on Oct. 21, 2016.

(51) Int. Cl.
| | | |
|---|---|---|
| *C07D 475/14* | (2006.01) | |
| *A61P 31/06* | (2006.01) | |
| *C07D 475/02* | (2006.01) | |

(52) U.S. Cl.
CPC ............ *C07D 475/14* (2013.01); *A61P 31/06* (2018.01); *C07D 475/02* (2013.01)

(58) Field of Classification Search
CPC ................................ C07D 475/14; A61P 31/06
See application file for complete search history.

(56) References Cited

U.S. PATENT DOCUMENTS

| | | | | | |
|---|---|---|---|---|---|
| 4,113,859 | A | * | 9/1978 | Wood ................... | C07D 471/04 514/264.1 |
| 4,252,946 | A | * | 2/1981 | Wood ................... | C07D 471/04 544/279 |
| 8,802,161 | B2 | * | 8/2014 | Mazzio ................. | A61K 36/00 424/725 |
| 10,011,602 | B2 | * | 7/2018 | Kjer-Nielsen ....... | C07D 475/02 |
| 2015/0166542 | A1 | | 6/2015 | Kjer-Nielsen et al. | |

FOREIGN PATENT DOCUMENTS

WO 2016046734 A2 3/2016

OTHER PUBLICATIONS

Blount et al., Novel Riboswitch-Binding Flavin Analog That Protects Mice against Clostridium difficile Infection without Inhibiting Cecal Flora, Antimicrobial Agents and Chemotherapy, Sep. 2015, vol. 59, No. 9, pp. 5376-5746.

Edmondson, Intramolecular Hemiacetal Formation in 8-Formylriboflavine, Biochemistry, vol. 13, No. 14, 1974, pp. 2817-2821.

Hill, Interrelationship Between Thioctic Acid, L-Lyxoflavin, and Riboflavin in *Streptococcus faecalis*, J. Bacteriology, vol. 65, 1953, pp. 578-580.

Howe et al., Selective small-molecule inhibition of an RNA structural element, Nature, vol. 526, Oct. 29, 2015, pp. 672-677.

McNutt et al., A Naturally Occurring Indolylpteridine, Biochemistry, vol. 8, Issue 4, pp. 1370-1376, 1969.

Pedrolli et al., Riboflavin Analogs as Antiinfectives: Occurrence, Mode of Action, Metabolism and Resistance, Current Pharmaceutical Design, 2013, 19, 000-000, pp. 1-9.

Reantragoon et al., Antigen-loaded MR1 tetramers define T cell receptor heterogeneity in mucosal-associated invariant T cells, Journal of Experimental Medicine, vol. 210, Issue 11, pp. 2305-2320, 2013.

Talkukdar et al., Discover and Development of a Small Molecule Library with Lumazine Synthase Inhibitory Activity, Journal of Organic Chemistry, vol. 74, Issue 15, pp. 5123-5134, 2009.

Walsh et al., Chemical and Enzymatic Properties of Riboflavin Analogues, Biochemistry, vol. 17, Issue 10, pp. 1942-1951, 1978.

Zhang et al., A New Series of N-[2,4-Dioxo-6-D-ribitylamino-1,2,3,4-tetrahydropyrimidin-5-yl]oxalamic Acid Derivatives as Inhibitors of Lumazine Synthase and Riboflavin Synthase: Design, Synthesis, Biochemical Evaluation, Crystallography, and Mechanistic Implications, J. Org Chem 2008, 73, pp. 2715-2724.

Gold et al, MR1-restricted MAIT cells display ligand discrimination and pathogen selectivity through distinct T cell receptor usage, J. Exp. Med., 2014, pp. 1601-1610, vol. 211, No. 8.

Gold et al, Human mucosal associated invariant T cells detect bacterially infected cells, PLoS Biol., 2010, pp. e1000407, vol. 8, No. 6.

Riegert et al, Genomics, isoforms, expression, and phylogeny of the MHC class I-related MR1 gene, J. Immunol., 1998, pp. 4066-4077, vol. 161, No. 8.

Bourhis et al, Antimicrobial activity of mucosal-associated invariant T cells, Nat. Immunol., 2010, pp. 701-708, vol. 11, No. 8.

Dusseaux et al, Human MAIT cells are xenobiotic-resistant, tissue-targeted, CD161hi IL-17-secreting T cells, Blood, 2011, pp. 1250-1259, vol. 117, No. 4.

Kjer-Nielsen et al, MR1 presents microbial vitamin B metabolites to MAIT cells, Nature, 2012, pp. 717-723, vol. 491, No. 7426.

Treiner et al, Selection of evolutionarily conserved mucosal-associated invariant T cells by MR1, Nature, 2003, pp. 164-169, vol. 422, No. 6928.

Van Rhijn et al, Lipid and small-molecule display by CD1 and MR1, Nat. Rev. Immunol., 2015, pp. 643-654, vol. 15, No. 10.

Huang et al, MR1 antigen presentation to mucosal-associated invariant T cells was highly conserved in evolution, Proc Natl Acad Sci USA, 2009, pp. 8290-8295, vol. 106, No. 20.

Corbett et al, T-cell activation by transitory neo-antigens derived from distinct microbial pathways, T-cell activation by transitory neo-antigens derived from distinct microbial pathways, Nature, 2014, pp. 361-365, vol. 509, No. 7500.

(Continued)

*Primary Examiner* — Golam M Shameem

(57) ABSTRACT

Disclosed are small molecules and pharmaceutical compositions comprising them that can be used in treating diseases associated with the major histocompatibility complex (MHC) molecule MR1.

7 Claims, 60 Drawing Sheets
(47 of 60 Drawing Sheet(s) Filed in Color)

(56) References Cited

OTHER PUBLICATIONS

Gherardin et al, Diversity of T Cells Restricted by the MHC Class I-Related Molecule MR1 Facilitates Differential Antigen Recognition, Immunity, 2016, pp. 32-45, vol. 44, No. 1.

Meermeier et al, Human TRAV1-2-negative MR1-restricted T cells detect S. pyogenes and alternatives to MAIT riboflavin-based antigens, Nature Communications, 2016, vol. 7, No. 12506.

Lopez-Sagaseta et al, MAIT Recognition of a Stimulatory Bacterial Antigen Bound to MR1, J. Immunol., 2013, pp. 5268-52T7, vol. 191, No. 10.

Sharma et al, High expression of CD26 accurately identifies human bacteria-reactive MR1-restricted MAIT cells, Immunology, 2015, pp. 443-453, vol. 145, No. 3.

Bourgeois et al, Bee venom processes human skin lipids for presentation by CD1a, J. Exp. Med., 2015, pp. 149-163, vol. 212, No. 2.

Jong et al, CD1a-autoreactive T cells recognize natural skin oils that function as headless antigens, Nat. Immunol. 2014, pp. 177-185, vol. 15, No. 2.

Adams et al, Structure of a gammadelta Cell Receptor in Complex with the Nonclassical MHC T22, Science, 2005, pp. 227-231, vol. 308, No. 5719.

Bashiri et al, Metabolic Engineering of Cofactor F420 Production in *Mycobacterium smegmatis*, PLoS One, 2010, pp. e15803, vol. 5, No. 12.

Selengut et al, Unexpected Abundance of Coenzyme F420-Dependent Enzymes in *Mycobacterium tuberculosis* and Other Actinobacteria, J. Bacteriol, 2010, pp. 5788-5798, vol. 192, No. 21.

Suzuki et al, Isolation and Characterization of Pteridines from Pseudomonas ovalis, Bulletin of the Chemical Society of Japan, 1971, pp. 1869-1872, vol. 44, No. 7.

Harriff et al, Endosomal MR1 Trafficking Plays a Key Role in Presentation of *Mycobacterium tuberculosis* Ligands to MAIT Cells, PLoS Pathog, 2016, pp. e1005524, vol. 12, No. 3.

Eckle et al, A molecular basis underpinning the T cell receptor heterogeneity of mucosal-associated invariant T cells, J. Exp. Med., 2014, pp. 1585-1600, vol. 211, No. 8.

Wang et al, Sharing and community curation of mass spectrometry data with Global Natural Products Social Molecular Networking, Nat. Biotechnol. 2016, pp. 828-837, vol. 34, No. 8.

* cited by examiner hpMR1+MS        hpMR1+EC        hpMR1-bac

RL-6-Me-7-OH

Theoretical [M-H]⁻
327.0946

Chemical Formula
$C_{12}H_{16}N_4O_7$

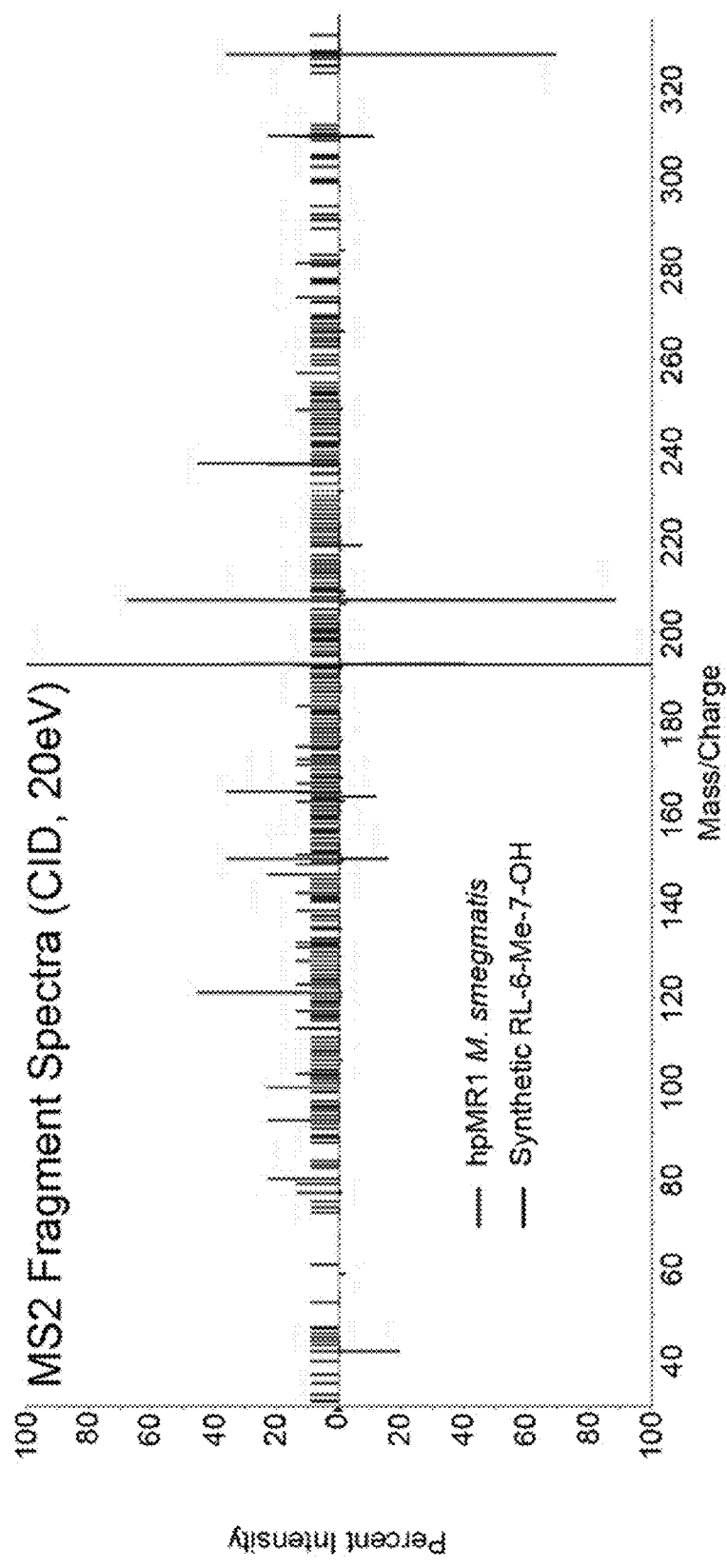

5-OE-RU

Theoretical [M-H]⁻
315.0946

Chemical Formula
$C_{11}H_{16}N_4O_7$

RL-6,7-diMe

Theoretical [M-H]⁻
325.1154

Chemical Formula
$C_{13}H_{18}N_4O_6$

Aectyl RL-6-Me-7-OH

Theoretical [M-H]⁻
369.1052

Chemical Formula
$C_{14}H_{18}N_4O_8$ 6-hydroxy-riboflavin

Theoretical [M-H]⁻
391.1265

Chemical Formula $C_{17}H_{20}N_4O_7$ 8-demethyl-8-hydroxy-riboflavin

Theoretical [M-H]⁻
377.1108

Chemical Formula $C_{16}H_{18}N_4O_7$ 8-demethyl-8-formyl-riboflavin

Theoretical [M-H]⁻
389.1108

Chemical Formula $C_{17}H_{18}N_4O_7$

Riboflavin

Theoretical [M-H]⁻
375.1310

Chemical Formula
$C_{17}H_{20}N_4O_6$ 7,8-didemtehyl-8-hydroxy-5-deazariboflavin (FO)

Theoretical [M-H]$^-$ = 362.0994

Chemical Formula $C_{16}H_{17}N_3O_7$ 6-(1H-indol-3-yl)-7-hydroxy-8-ribityllumazine (Photolumazine III)

Theoretical [M-H]⁻ = 428.1212

Chemical Formula $C_{19}H_{19}N_5O_7$ 6-(2-carboxyethyl)-7-hydroxy-8-ribityllumazine
(Photolumazine I)

Theoretical [M-H]$^-$ = 385.1001

Chemical Formula $C_{14}H_{18}N_4O_9$

SMALL MOLECULES THAT BIND MR1

RELATED APPLICATIONS

This application claims priority to U.S. Provisional Patent Application 62/411,208, filed on 21 Oct. 2016, entitled SMALL MOLECULES THAT BIND MR1, which is incorporated by reference herein.

FIELD OF THE INVENTION

Generally, the field involves small molecular entities. More specifically, the field involves compounds in the F420 biosynthesis pathway that bind the major histocompatibility complex (MHC) molecule MR1.

BACKGROUND

The T cell receptor (TCR), a heterodimer comprised of α and β chains derived by recombination in the thymus, enables T cells to recognize non-self ligands presented in the context of conventional and non-conventional major histocompatibility (MHC) molecules. Conventional MHC molecules have undergone divergent evolution to present a broad array of peptides However, the non-conventional CD1 molecules are highly conserved and present lipid and glycolipid antigens (Van Rhijn I et al, Nat Rev Immunol 15, 643-654 (2015); incorporated by reference herein). Like CD1, MR1 is a non-conventional MHC molecule that is highly conserved and located on human chromosome 1 (Riegert P et al, J Immunol 161, 4066-4077 (1998); incorporated by reference herein). CD1 presents small molecules from microbes such as *Mycobacterium tuberculosis, Salmonella typhimurium*, and *Candida albicans* (Gold M C et al, PLoS Biol 8 e1000407 (2010); Gold M C et al, J Exp Med 211, 1601-1610 (2014); Le Bourhis L et al, Nat Immunol 11, 701-708 (2010); all of which are incorporated by reference herein). MR1-restricted T cells (MR1Ts) are the T cell subset that recognizes these microbial small molecules bound to MR1 (Gold 2010 supra, Le Bourhis 2010 supra, Dusseaux M et al, *Blood* 117, 1250-1259 (2011); Kjer-Nielsen L et al, *Nature* 491, 717-723 (2012); Treiner E et al, *Nature* 422, 164-169 (2003); all of which are incorporated by reference herein). Mucosal-associated invariant T cells (MAITs), a subset of human MR1Ts, were defined by the use of a semi-invariant T cell receptor that includes a single c chain rearrangement (TRAV1-2 and TRAJ33) paired with a limited number of 3 chains (TRBV6 and TRBV20) (Treiner 2003 supra). The use of a highly conserved antigen presentation molecule along with limited TCR diversity suggested that MAIT cells were limited to recognizing a small repertoire of ligands and unable to discriminate between ligands (Huang S et al, *Proc Natl Acad Sci USA* 106, 8290-8295 (2009); incorporated by reference herein).

That the known activating ligands for MAIT cells are solely derived from the riboflavin biosynthesis pathway, (Kjer-Nielsen 2012 supra, Corbett A J et al, Nature 509, 361-365 (2014); incorporated by reference herein), and that only microbes that synthesize riboflavin were initially demonstrated to stimulate MAIT cells was viewed as further proof of this restriction. Furthermore, the semi-invariant nature of the MAIT cell TCR has been used to argue that MAIT cells do not possess properties of immunologic memory, specifically antigen-driven clonal expansions reflective of antigenic exposure and persistence. However, recent evidence of diverse TCR usage among MR1T cells (Gold 2014 supra; Gherardin N A et al, *Immunity* 44, 32-45 (2016); Meermeier E W et al, Nat Commun 16, 12506 (2016); both of which are incorporated by reference herein) and structural flexibility in the MR1 binding pocket (Lopez-Sagaseta et al, *J Immunol* 191, 5268-5277 (2013); incorporated by reference herein) raise the possibility of ligand diversity and the ability to discriminate between specific microbes.

SUMMARY OF THE INVENTION

MR1-restricted T cells (MR1Ts) are a T cell subset that recognize and mediate host defense to a broad array of microbial pathogens important to human health, including respiratory pathogens (e.g. *Mycobacterium tuberculosis* and *Streptococcus pyogenes*) and enteric pathogens (e.g. *E. coli* and *Salmonella* species). MR1Ts were historically defined by the use of a semi-invariant T cell receptor (TCR), which recognizes microbial small molecules derived from the riboflavin biosynthesis pathway presented on MR1.

Disclosed herein is the use of mass spectrometry to identify MR1 ligands derived from cells infected with *E. coli* and *M. smegmatis*. We found that the MR1 ligandome is unexpectedly broad, and demonstrate functionally distinct ligands derived from *E. coli* and *M. smegmatis*-infected cells. The identification, synthesis, and functional analysis of unique mycobacterial ligands reveals that novel MR1T ligands can be distinguished by MR1Ts with diverse TCR usage. These data suggest that MR1 serves as an immune sensor of the microbial ligandome. Disclosed herein are functional and biochemical analysis of MR1 ligands presented in the context of infection with discrete microbes and defined MR1 as a sensor of the microbial metabolome.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 8D depicts a MS2 fragment spectra of the precursor ion in indicated sample.

DETAILED DESCRIPTION OF THE INVENTION

Figure 1A:
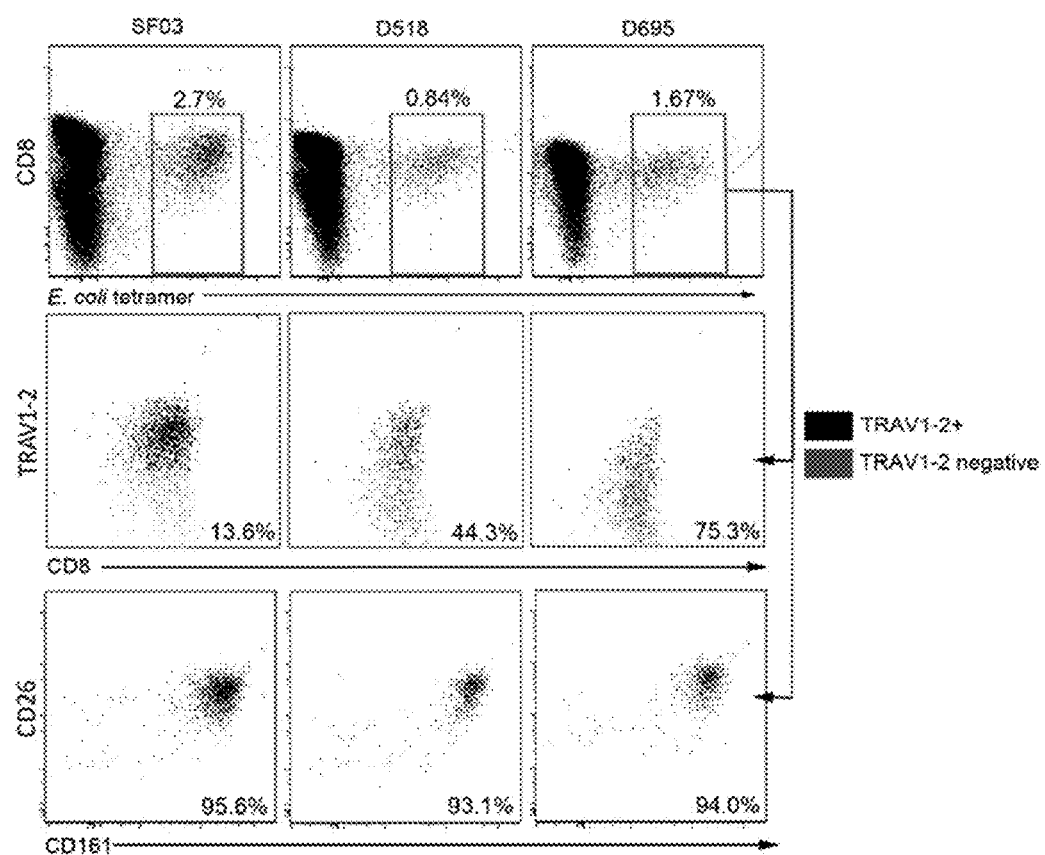
FIG. 1A provides a representative dot plot denoting (red box) the frequency of CD3+CD4−hpMR1+EC tetramer+ cells; (middle box) TRAV1-2 staining of hpMR1+EC tetramer+ cells; and (bottom box) CD26 and CD161+ staining of hpMR1+EC tetramer+ cells.

Provided herein are compounds of Formula 1a, Formula 2a, Formula 1b, and Formula 2b, or a pharmaceutically acceptable salt thereof:

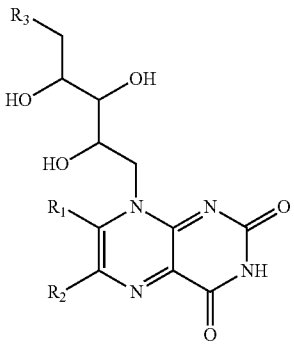

1a

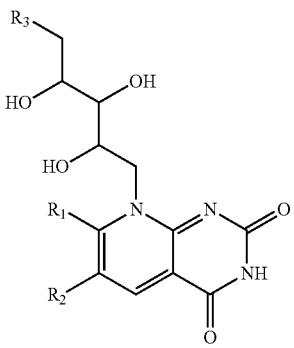

2a

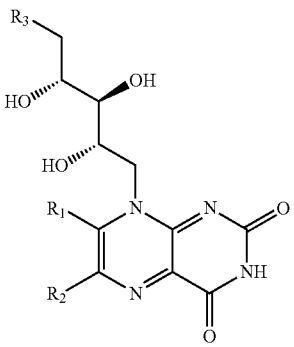

1b

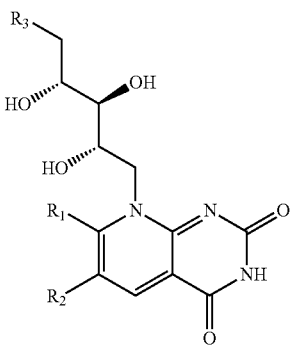

2b wherein, in each appearance:

$R_1$ is independently selected from H, OH, $C_1$-$C_3$ alkyl, and —CH=O;

$R_2$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from H, OH, $CH_3$, and —CH=O;

$R_2$ is independently selected from H, a 5-10-membered carbocycle, a 5-10-membered heterocycle, $CH_3$, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from H, OH, $CH_3$, and —CH=O;

$R_2$ is independently selected from H, phenyl, indole, $CH_3$, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from H, OH, $CH_3$, and —CH=O;

$R_2$ is independently selected from H, indole, $CH_3$, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from OH, $CH_3$, and —CH=O;

$R_2$ is independently selected from indole, $CH_3$, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from OH;

$R_2$ is independently selected from indole, $CH_3$, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from $CH_3$;

$R_2$ is independently selected from indole, —$CH_2$—OH and —$CH_2$—$CO_2H$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is independently selected from OH and $CH_3$;

$R_2$ is $CH_3$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is OH;

$R_2$ is $CH_3$; and $R_3$ is selected from OH and —O(C=O)—$C_1$-$C_3$ alkyl.

Also are provided are compounds of Formula 1a, Formula 1b, Formula 2a, and Formula 2b, or a pharmaceutically acceptable salt thereof, wherein, in each appearance:

$R_1$ is $CH_3$;

$R_2$ is $CH_3$; and $R_3$ is selected from OH and —O(C=O)—$C_1$-$C_3$ alkyl.

Within the scope of Formula 1a, Formula 1b, Formula 2a, or Formula 2b, or a pharmaceutically acceptable salt thereof, are provided the following compounds, or a pharmaceutically acceptable salt thereof:

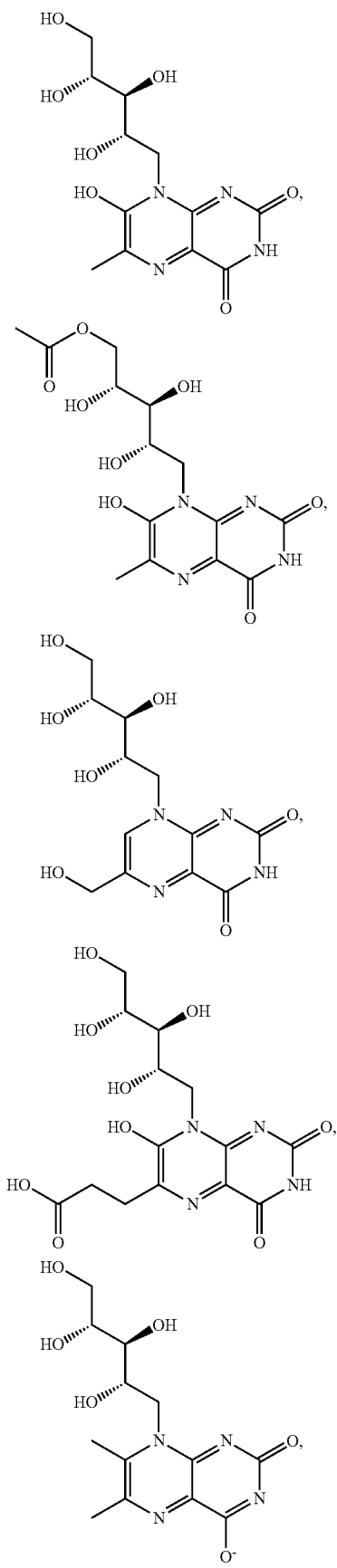

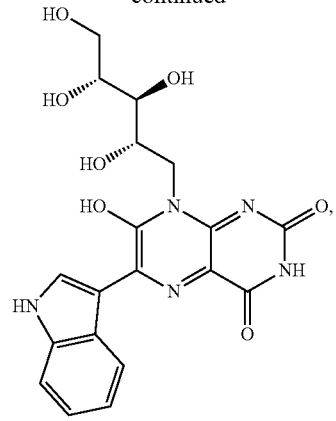

-continued

Also provided are compounds of Formula 3a and Formula 3b:

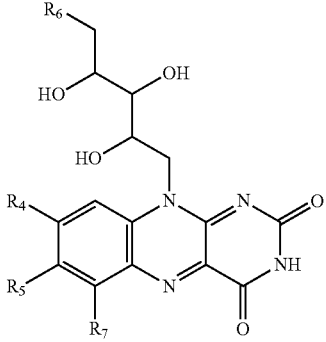

3a

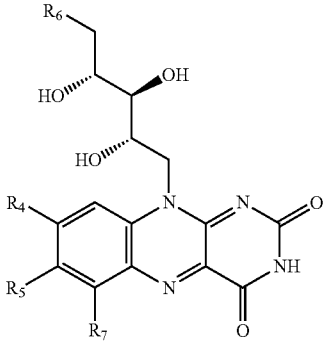

3b wherein, in each appearance:

$R_4$ is independently selected from H, OH, $C_1$-$C_3$ alkyl, and —CH=O;

$R_5$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$;

$R_6$ is selected from OH and —O(C=O)—$C_1$-$C_3$ alkyl; and $R_7$ is H or OH.

Also provided are compounds of Formula 3a and Formula 3b, or a pharmaceutically acceptable salt thereof wherein, in each appearance:

$R_4$ is independently selected from H, OH, $CH_3$, and —CH=O;

$R_5$ is independently selected from H, a 5-10-membered carbocycle, a 5-10-membered heterocycle, $CH_3$, —$CH_2$—OH and —$CH_2$—$CO_2H$;

$R_6$ is selected from OH and —O(C=O)-$C_1$-$C_3$ alkyl;

$R_7$ is H or OH.

Also are provided are compounds of Formula 3a and Formula 3b, or a pharmaceutically acceptable salt thereof wherein, in each appearance:

$R_4$ is independently selected from H, OH, $CH_3$, and —CH=O;

$R_5$ is independently selected from H, phenyl, indole, $CH_3$, —$CH_2$—OH and —$CH_2$—$CO_2H$;

$R_6$ is selected from OH and —O(C=O)—$C_1$-$C_3$ alkyl;

$R_7$ is H or OH.

Also are provided are compounds of Formula 3a and Formula 3b, or a pharmaceutically acceptable salt thereof wherein, in each appearance:

$R_4$ is independently selected from H, OH, $CH_3$, and —CH=O;

$R_5$ is independently selected from H, indole, $CH_3$, —$CH_2$—OH and —$CH_2$—$CO_2H$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is independently selected from OH, $CH_3$, and —CH=O;

$R_5$ is independently selected from indole, $CH_3$, —$CH_2$—OH and —$CH_2$—$CO_2H$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is independently selected from OH;

$R_5$ is independently selected from indole, $CH_3$, —$CH_2$—OH and —$CH_2$—$CO_2H$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is independently selected from $CH_3$;

$R_5$ is independently selected from indole, —$CH_2$—OH and —$CH_2$—$CO_2H$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is independently selected from OH and $CH_3$;

$R_5$ is $CH_3$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is OH;

$R_5$ is $CH_3$; and $R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is $CH_3$;

$R_5$ is $CH_3$;

$R_6$ is selected from OH and —O(C=O)—$C_1$-$C_3$ alkyl; and $R_7$ is H or OH.

Also are provided are compounds of Formula 3a and Formula 3b, or a pharmaceutically acceptable salt thereof wherein, in each appearance:

$R_4$ is —CH=O;

$R_5$ is $CH_3$;

$R_6$ is selected from OH and —O(C=O)—$C_1$-$C_3$ alkyl; and $R_7$ is H or OH.

Specific compounds herein within the scope of Formula 3a and Formula 3b include:

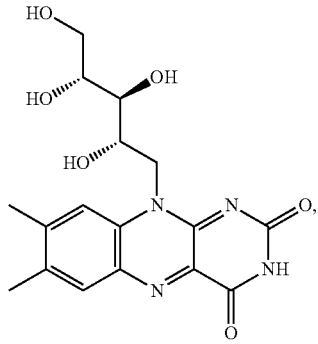

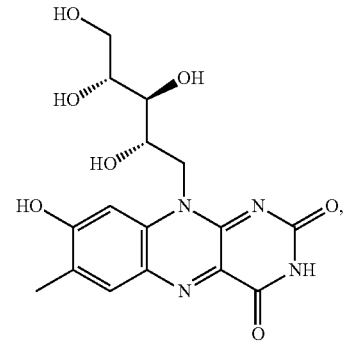

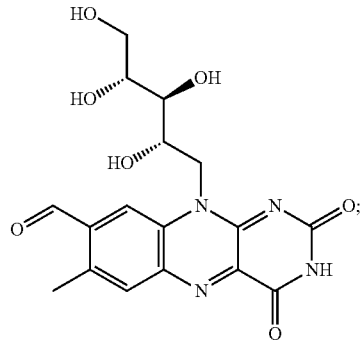

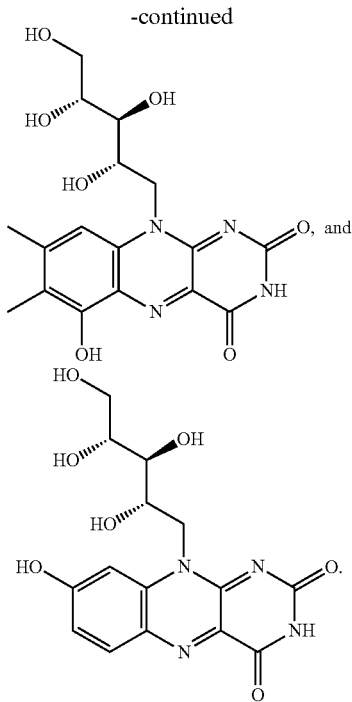

or a pharmaceutically acceptable salt thereof.

It is understood that each of the compounds described herein includes each possible tautomer of the compound, such as the tautomeric pair shown below.

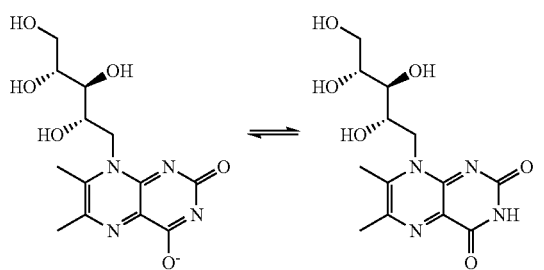 [SMILES: Cc1nc2c([O-])nc(=O)nc-2n(C[C@H](O)[C@H](O)[C@H](O)CO)c1C ; Cc1nc2c(=O)[nH]c(=O)nc-2n(C[C@H](O)[C@H](O)[C@H](O)CO)c1C]

Within each of the groups of compounds listed above there is a further group of compounds in which each of $R_1$, $R_2$, $R_3$, $R_4$, $R_5$ and $R_7$ are as defined and $R_6$ is selected from OH and —O(C=O)—CH$_3$.

Within each of the groups of compounds listed above there is a further group of compounds in which each of $R_1$, $R_2$, $R_3$, $R_4$, $R_5$ and $R_7$ are as defined and $R_6$ is OH.

Within each of the groups listed above for a compound of Formula 3a or Formula 3b there is a further embodiment in which $R_4$, $R_5$, and $R_6$ are as defined for the group and $R_7$ is H.

Within each of the groups listed above for a compound of Formula 3a or Formula 3b there is also a further embodiment in which $R_4$, $R_5$, and $R_6$ are as defined for the group and $R_7$ is OH.

In the compounds herein a 5-10-membered carbocycle can comprise a monocyclic or bicyclic, aliphatic or aromatic carbocyclic ring system including cycloheptyl, cyclohexyl, cycloheptyl, phenyl, and naphthyl groups. A 5-10 membered heterocycle can also be a monocyclic or bicyclic, aliphatic or aromatic heterocyclic ring system, including pyrrolyl, pyrrolidinyl, imidazolyl, thiazolyl, thiofenyl (thiophenyl), furanyl, tetrahydrofuranyl, pyridinyl, piperidinyl, pyrimidinyl, pyrazinyl, pyranyl, tetrahydropyranyl, indolyl, quinolinyl, isoquinolinyl, and purinyl.

Also provided herein is a method of treating respiratory bacterial pathogen infections in a subject, such as a human subject, the method comprising administering to the subject a pharmaceutically effective amount of a compound described herein, or a pharmaceutically acceptable salt thereof.

As such, provided is a method of treating respiratory bacterial pathogen infections in a subject, such as a human subject, the method comprising administering to the subject a pharmaceutically effective amount of a compound of Formula 1a, or a pharmaceutically acceptable salt thereof.

Also provided is a method of treating respiratory bacterial pathogen infections in a subject, such as a human subject, the method comprising administering to the subject a pharmaceutically effective amount of a compound of Formula 1b, or a pharmaceutically acceptable salt thereof.

Further provided is a method of treating respiratory bacterial pathogen infections in a subject, such as a human subject, the method comprising administering to the subject a pharmaceutically effective amount of a compound of Formula 2a, or a pharmaceutically acceptable salt thereof.

Provided is a method of treating respiratory bacterial pathogen infections in a subject, such as a human subject, the method comprising administering to the subject a pharmaceutically effective amount of a compound of Formula 2b, or a pharmaceutically acceptable salt thereof.

Further provided is a method of treating respiratory bacterial pathogen infections in a subject, such as a human subject, the method comprising administering to the subject a pharmaceutically effective amount of a compound of Formula 3a, or a pharmaceutically acceptable salt thereof.

Provided is a method of treating respiratory bacterial pathogen infections in a subject, such as a human subject, the method comprising administering to the subject a pharmaceutically effective amount of a compound of Formula 3b, or a pharmaceutically acceptable salt thereof.

There are comparable methods provided herein for treating respiratory bacterial pathogen infections in a subject, such as a human subject, the methods each comprising administering to the subject a pharmaceutically effective amount of one of the specific compounds described herein, or a pharmaceutically acceptable salt thereof.

Also provided herein is a method of treating *Mycobacterium tuberculosis* infections in a subject, such as a human subject, the method comprising administering to the subject a pharmaceutically effective amount of a compound described herein, or a pharmaceutically acceptable salt thereof.

As such, provided is a method of treating *Mycobacterium tuberculosis* infections in a subject, such as a human subject, the method comprising administering to the subject a pharmaceutically effective amount of a compound of Formula 1a, or a pharmaceutically acceptable salt thereof.

Also provided is a method of treating *Mycobacterium tuberculosis* infections in a subject, such as a human subject, the method comprising administering to the subject a pharmaceutically effective amount of a compound of Formula 1b, or a pharmaceutically acceptable salt thereof.

Further provided is a method of treating *Mycobacterium tuberculosis* infections in a subject, such as a human subject, the method comprising administering to the subject a pharmaceutically effective amount of a compound of Formula 2a, or a pharmaceutically acceptable salt thereof.

Provided is a method of treating *Mycobacterium tuberculosis* infections in a subject, such as a human subject, the method comprising administering to the subject a pharmaceutically effective amount of a compound of Formula 2b, or a pharmaceutically acceptable salt thereof.

Further provided is a method of treating *Mycobacterium tuberculosis* infections in a subject, such as a human subject, the method comprising administering to the subject a pharmaceutically effective amount of a compound of Formula 3a, or a pharmaceutically acceptable salt thereof.

Provided is a method of treating *Mycobacterium tuberculosis* infections in a subject, such as a human subject, the method comprising administering to the subject a pharmaceutically effective amount of a compound of Formula 3b, or a pharmaceutically acceptable salt thereof.

There are comparable methods provided herein for treating *Mycobacterium tuberculosis* infections in a subject, such as a human subject, the methods each comprising administering to the subject a pharmaceutically effective amount of one of the specific compounds described herein, or a pharmaceutically acceptable salt thereof.

For each of the methods described above for the treatment of *Mycobacterium tuberculosis*, there is an additional method for the treatment of a *Streptococcus pyogenes* infection in a subject, such as a human subject, each method comprising administering a compound defined herein or a pharmaceutically acceptable salt thereof.

For each of the methods described above for the treatment of *Mycobacterium tuberculosis*, there is an additional method for the treatment of enteric biological infections in a subject, such as a human subject, each method comprising administering a compound defined herein or a pharmaceutically acceptable salt thereof.

For each of the methods described above for the treatment of enteric biological infections in a subject, such as a human subject, there is a further embodiment wherein the enteric biological infection is an *E. coli* infection.

For each of the methods described above for the treatment of enteric biological infections in a subject, such as a human subject, there is a further embodiment wherein the enteric biological infection is a *Salmonella* infection.

Also provided are pharmaceutical compositions, each pharmaceutical composition comprising a pharmaceutically effective amount of a compound as described herein, or a pharmaceutically acceptable salt thereof, and a pharmaceutically acceptable carrier or excipient.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for the treatment of a respiratory biological pathogen.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for treating *Mycobacterium tuberculosis* infections in a subject, such as a human subject.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for the treatment of a *Streptococcus pyogenes* infection in a subject, such as a human subject.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for the treatment of an enteric biological pathogen.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for treating an *E. coli* infection in a subject, such as a human subject.

Also provided are individual methods comprising the use of a compound of Formula 1a, Formula 1b, Formula 2a, Formula 2b, Formula 3a, Formula 3b, or any of the specific compounds disclosed herein, or a pharmaceutically acceptable salt thereof, in the preparation of a medicament for the treatment of a *Salmonella* infection in a subject, such as a human subject.

The present compounds may also be utilized as an adjuvant or an excipient in the preparation of a medicament for the treatment of any of the maladies referenced herein in combination with one or more other pharmaceutically active agents.

The present compounds may also be used as a vaccine in a subject, such as a human subject, in advance of each of the maladies described herein.

Terms:

7,8-didemethyl-8-hydroxy-5-deazariboflavin (FO) is a small molecule metabolite in the coenzyme F420 biosynthesis pathway. Microbes that generate $F_{420}$ produce FO moiety using a pyrimidine intermediate from riboflavin biosynthesis and the 4-hydroxyphenylpyruvate precursor of tyrosine—a reaction that is catalyzed by 7,8-didemethyl-8-hydroxy-5-deazariboflavin synthase (Graham D E et al, Arch Microbiol 180, 455-464 (2003); incorporated by reference herein)

FO binds MR1, but blocks the activation of MAIT cells. 6,7-dimethyl-5-deazalumazine (DZ) is a synthetic compound designed based on the structure and activity of FO and other known mycobacterial ligands for MR1. It binds MR1 and activates MR1 restricted T cells. Photolumazines I and III are small molecule secondary metabolites produced by bacteria. The photolumazines bind MR1 and activated MR1 restricted T cells.

Binding or stable binding: An association between two substances or molecules such as the association of a small molecule such as 7,8-didemethyl-8-hydroxy-5-deazariboflavin, 6,7-dimethyl-5-deazalumazine, photolumazine I or photolumazine III with MR1. Binding can be detected by any procedure known to one skilled in the art, such as by physical or functional properties including cellular properties. Binding can also be detected by visualization of a label (such as a fluorescent label) conjugated to one of the molecules.

Cancer: A disease or condition in which abnormal cells divide without control and are able to invade other tissues. Cancer cells spread to other body parts through the blood and lymphatic systems. Cancer is a term for many diseases, there are more than 100 different types of cancer in humans. Most cancers are named after the organ in which they originate. For instance, a cancer that begins in the colon is called a colon cancer. However, the characteristics of a cancer, especially with regard to the sensitivity of the cancer to therapeutic compounds, are not limited to the organ in which the cancer originates.

Cancer is a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes all phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

While historically, cancers have been and still are characterized by their tissues of origin, more recently, cancers, including solid tumors, have been characterized by other features including expression of gene products such as mRNA or proteins (including cell surface proteins) as well as their resistance or susceptibility to drugs, hormones, or other compounds.

Effective Amount: An amount of an agent that is sufficient to generate a desired response such as reducing or eliminating a sign or symptom of a condition or a disease. Such signs or symptoms can include reduction in the rate of growth of a tumor (including halting the growth of a tumor or shrinking a tumor), preventing or otherwise treating a metastatic tumor, or preventing or reducing the spread of an infectious disease.

Subject: A living multicellular vertebrate organism, a category that includes, for example, mammals and birds. A "mammal" includes both human and non-human mammals, such as mice. In some examples, a subject is a patient.

Treating a disease: Inhibiting the full development of a disease or condition. "Treatment" refers to any therapeutic intervention that ameliorates a sign or symptom of a disease or pathological condition. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology. A "therapeutic" treatment is a treatment administered after the development of significant signs or symptoms of the disease.

Tumor: All neoplastic cell growth and proliferation, whether malignant or benign, and all pre-cancerous and cancerous cells and tissues.

Pharmaceutical Compositions

The compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients.

Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acidglycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5-isobutyl 2-cyanoacrylate (see, for example, Michael et al., *J. Pharmacy Pharmacol.* 43, 1-5, (1991), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (betahydroxy butyric acid), poly(alkyl-2-cyanoacrilate), hydrogels, such as poly(hydroxyethyl methacrylate), poly-amides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Treatment

Disclosed herein are methods of treating a subject with a neurodegenerative disorder through administration of one or more of the disclosed compounds. The compounds can be administered by any appropriate route including orally, parenterally, or topically. In particular examples, a PTPσ inhibitor disclosed herein, or a pharmaceutically acceptable salt thereof, is administered orally. In certain examples, the PTPσ inhibitor, or pharmaceutically acceptable salt thereof, is administered parenterally. In some embodiments, the PTPσ inhibitor, or pharmaceutically acceptable salt thereof, is administered buccally, sublingually, sublabially, or by inhalation. In other embodiments, the PTPσ inhibitor, or pharmaceutically acceptable salt thereof, is administered sublingually. In yet other embodiments, the PTP-σ inhibitor, or pharmaceutically acceptable salt thereof, is administered parenterally. In particular embodiments, the PTPσ inhibitor, or pharmaceutically acceptable salt thereof, is administered intra-arterially, intravenously, intraventricularly, intramuscularly, subcutaneously, intraspinally, intraorbitally, intracranially or intrathecally.

The administration of a pharmaceutical composition comprising the disclosed compounds can be for prophylactic or therapeutic purposes. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with a disease or condition characterized by neuronal injury.

An effective amount or concentration of the disclosed compounds may be any amount of a composition that alone, or together with one or more additional therapeutic agents, is sufficient to achieve a desired effect in a subject. The effective amount of the agent will be dependent on several factors, including, but not limited to, the subject being treated and the manner of administration of the therapeutic composition. In one example, a therapeutically effective amount or concentration is one that is sufficient to prevent advancement, delay progression, or to cause regression of a disease or condition, or which is capable of reducing symptoms caused by any disease or condition, including a disease or condition characterized by neuronal injury.

In one example, a desired effect is to reduce or inhibit one or more symptoms associated with a disease or condition characterized by neuronal injury. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to how the sign or symptom would have progressed in the absence of the composition or in comparison to currently available treatments.

The actual effective amount will vary according to factors such as the type of neurological disorder to be protected against/therapeutically treated and the particular status of the subject (for example, the subject's age, size, fitness, extent of symptoms, susceptibility factors, and the like) time and route of administration, other drugs or treatments being administered concurrently, as well as the specific pharmacology of treatments for viral infection for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for viral infection within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight to about 10 mg/kg body weight per dose.

Determination of effective amount is typically based on animal model studies followed up by human clinical trials and is guided by administration protocols that significantly reduce the occurrence or severity of targeted disease or condition symptoms in the subject. Suitable models in this regard include, for example, murine, rat, rabbit, porcine, feline, non-human primate, and other accepted animal model subjects known in the arts. Using such models, only ordinary calculations and adjustments are required to determine an appropriate concentration and dose to administer a therapeutically effective amount of the treatments for cancer immunotherapy and/or for infectious disease such as a mycobacterial or bacterial infection.

EXAMPLES

The following examples are for illustration only. In light of this disclosure, those of skill in the art will recognize that variations of these examples and other examples of the disclosed invention be possible without undue experimentation.

Example 1

The Microbial MR1 Ligandome

Figure 5A:
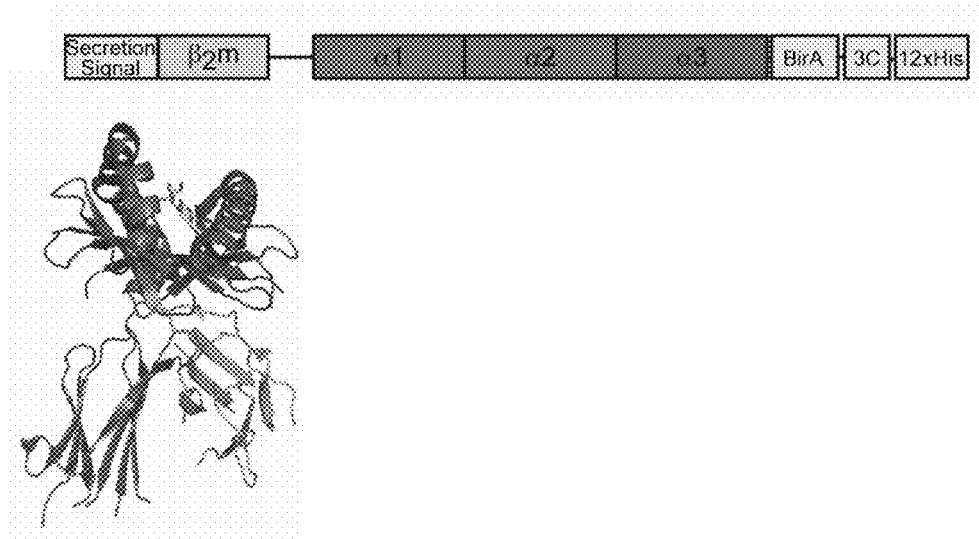
FIG. 5A depicts a schematic representation of hpMR1 construct. Human MR1 sequence is represented in blue and bovine MR1 sequence is represented in pink. Also shown is the structure of MR1 (PDB: 4LCC) colored to match the schematic of the hpMR1 construct.
Figure 5B:
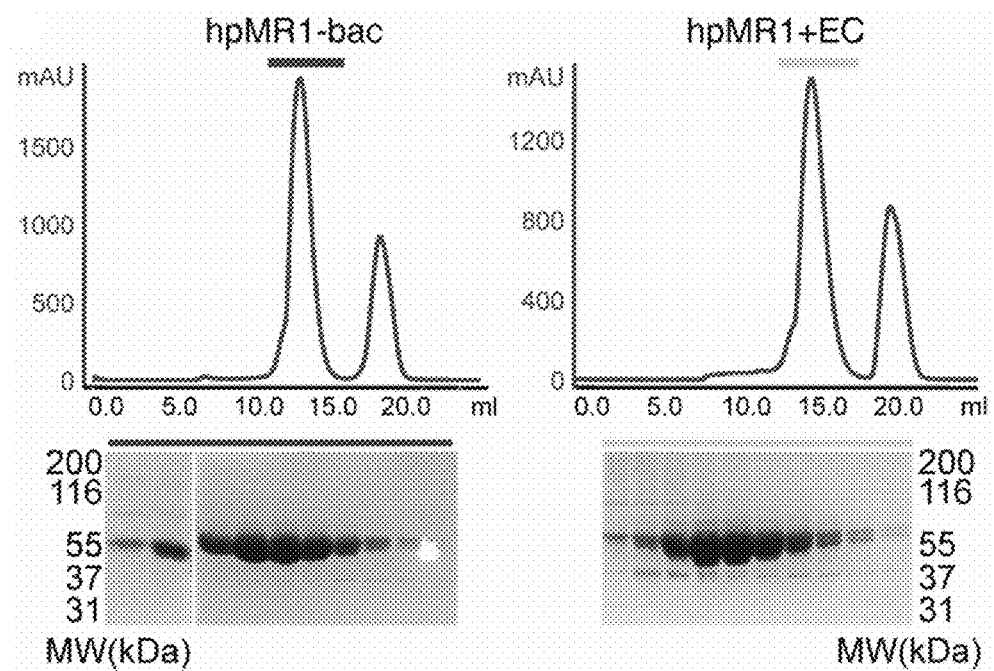
FIG. 5B demonstrates size exclusion chromatography of hpMR1-bac and hpMR1+EC and SDS-PAGE of fractions from the purification. Bars represent the fractions that were collected and run on an SDS-PAGE gel.
Figure 5C:
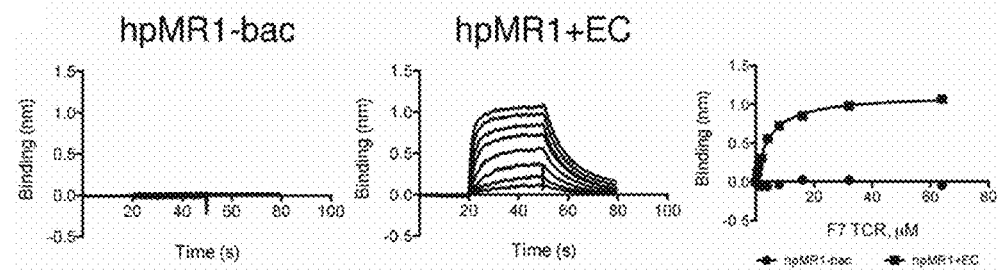
FIG. 5C demonstrates bio-layer interferometry analysis of the F7 MAIT TCR binding to hpMR1-bac or hpMR1+EC. Biotinylated hpMR1-bac or +EC was immobilized on a streptavidin biosensor followed by running increasing concentrations of the F7 MAIT TCR from 0 to 64 µM. Buffer alone (0 µM TCR) was subtracted from each, and the subtracted equilibrium binding was plotted against TCR concentration.
Figure 5D:
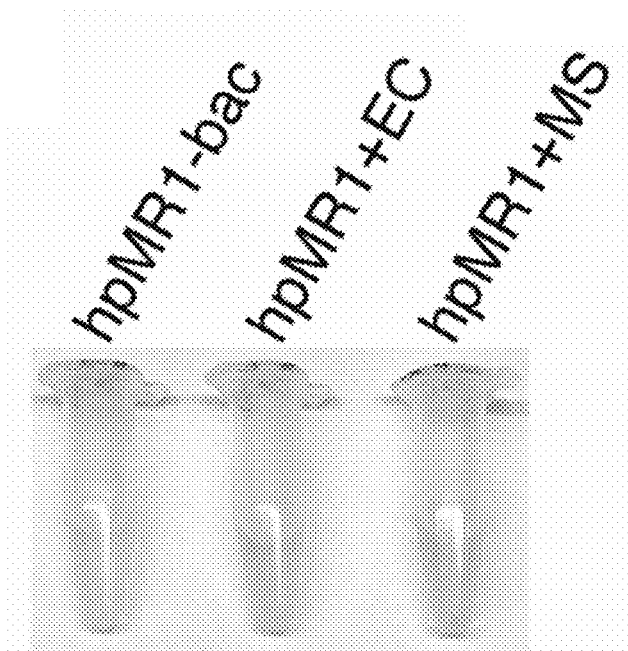
FIG. 5D shows concentrated hpMR1-bac, hpMR1+EC, and hpMR1+MS proteins after size exclusion purification. Each protein has a distinctly different color, likely due to the different repertoire of ligands present from the specific bacteria or absence of bacteria.

MR1 expressed in cells infected with two distinct microbes recognized by MR1Ts, *E. coli* and *M. smegmatis*, were analyzed by flow cytometry, ELISPOT assay, and mass spectrometry. A chimeric version of soluble MR1 (hpMR1) comprised of human $\alpha 1$ and $\alpha 2$ sequences with bovine $\alpha 3$ and $\beta 2m$ sequences (FIG. 5A) was generated. The hpMR1 protein is stable and highly expressed (FIG. 5B), and recapitulates ligand binding and TCR interactions of human MR1 (FIG. 5C). Insect cells expressing hpMR1 were left uninfected or infected with live *E. coli* or *M. smegmatis*. hpMR1 expressed in the absence of any bacteria (hpMR1-bac), or following infection with either *E. coli* (hpMR1+EC) or *M. smegmatis* (hpMR1+MS), had distinctly different colors (FIG. 5D), suggesting a difference in the ligand repertoire.

Figure 6:
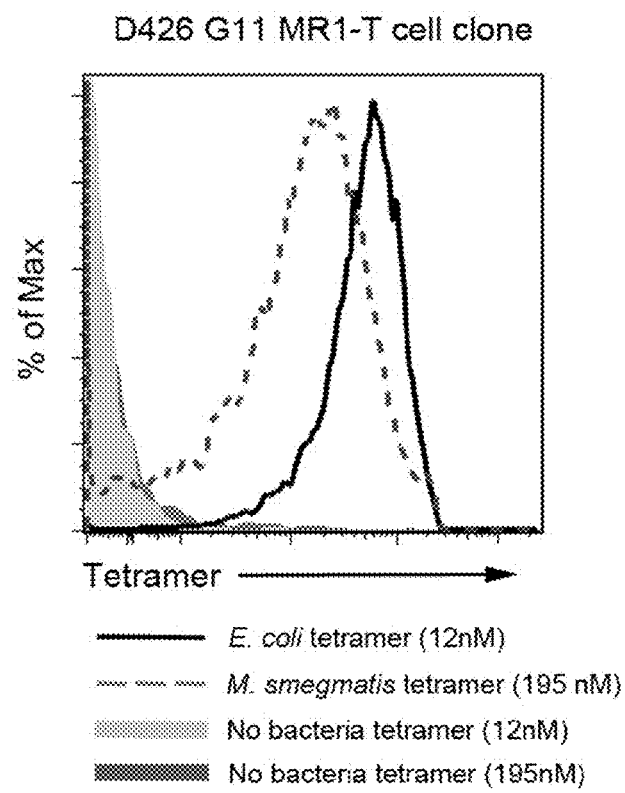
FIG. 6 depicts hpMR1 tetramer staining of MR1T cell clone. The D426 G11 MR1T cell clone was stained with the hpMR1-bac and +EC tetramers at 12 nM per test or the hpMR1-bac and +MS tetramers at 195 nM per test. The solid light and dark grey histograms represent the hpMR1-bac staining at either concentration.
Figure 7A:
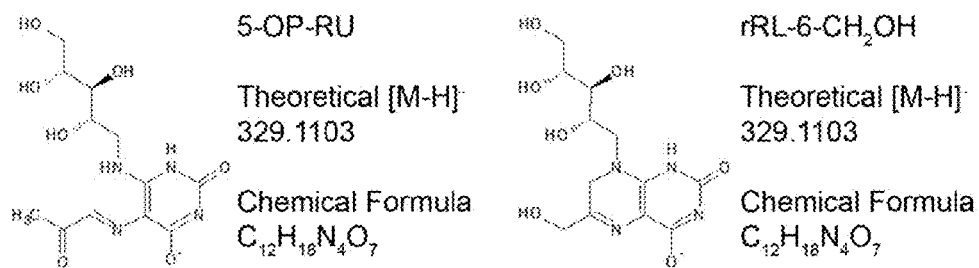
FIG. 7A shows the [M-H]− ion structure, theoretical monoisotopic mass, and chemical formula for 5-OP-RU (left) and rRL-6-CH2—OH (right).
Figure 7B:
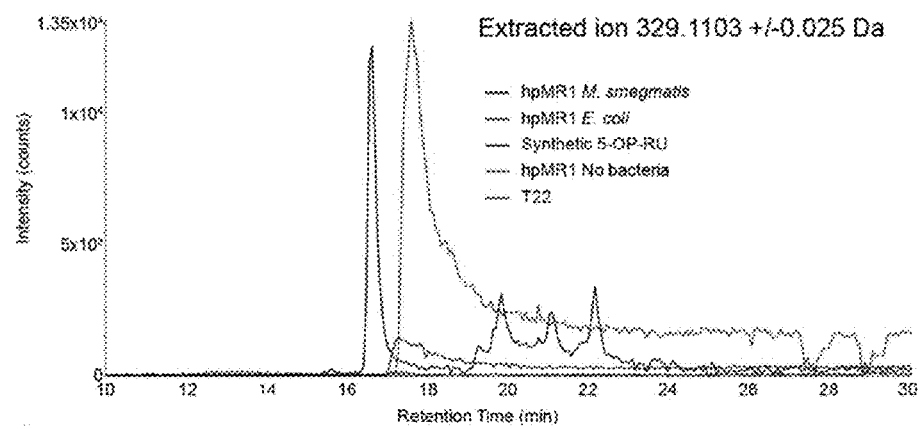
FIG. 7B depicts an extracted ion chromatogram overlay of the theoretical mass of 5-OP-RU/rRL-6CH2OH in hpMR1+MS (blue), hpMR1+EC (red), hpMR1-bac (purple), T22 (green), or synthetic 5-OP-RU (black).
Figure 7C:
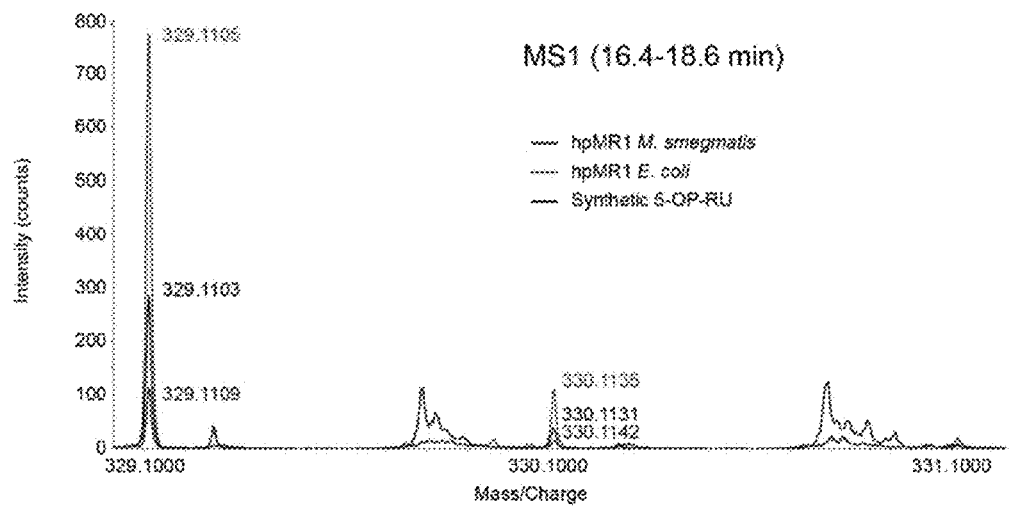
FIG. 7C depicts a MS1 survey spectra overlay of the relevant ion over the indicated retention time range in hpMR1+EC. Observed m/z for the ion and the respective +1 isotope are labeled and color coded to match the sample trace color.
Figure 7D:
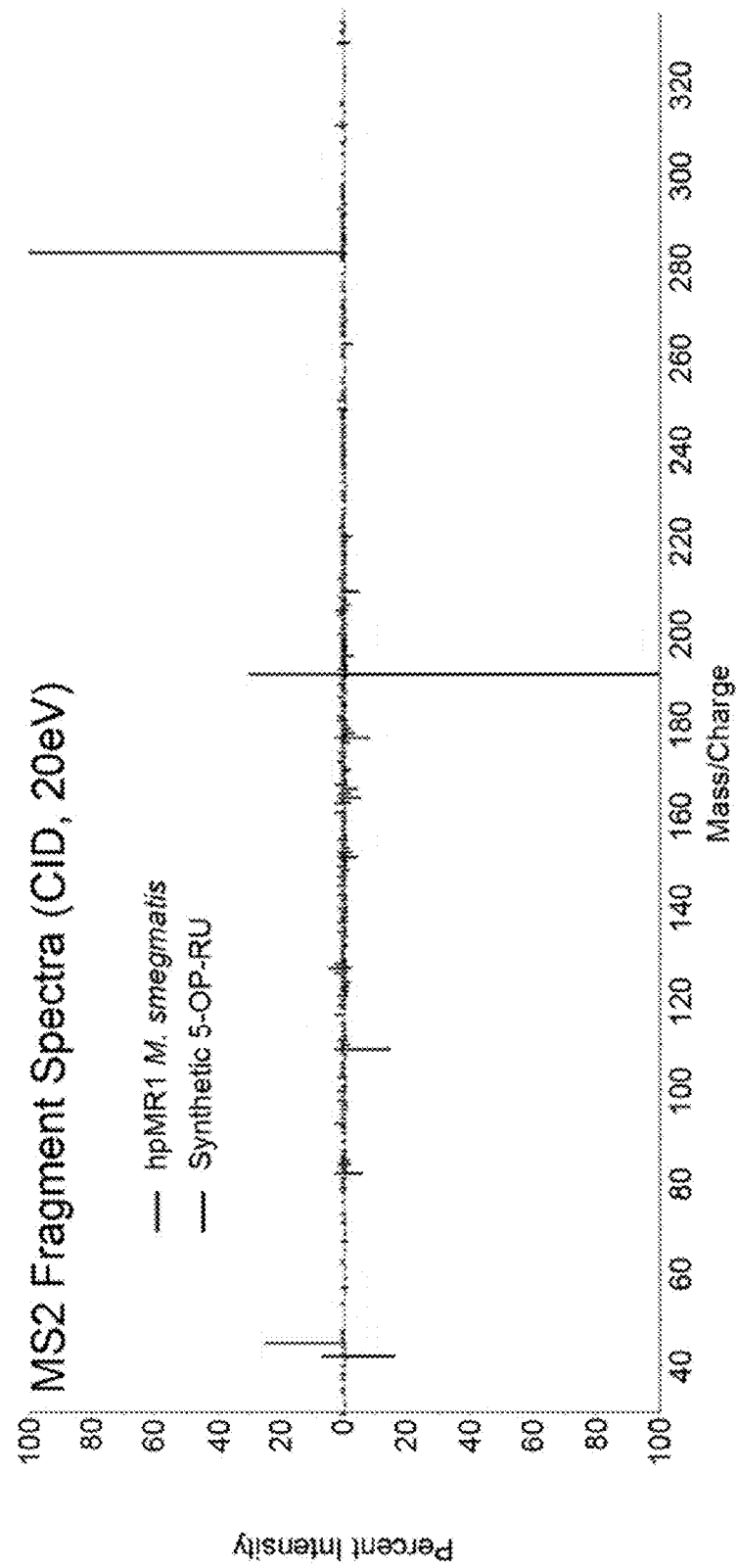
FIG. 7D depicts a MS2 fragment spectra of the precursor ion in indicated sample.
Figure 7E:
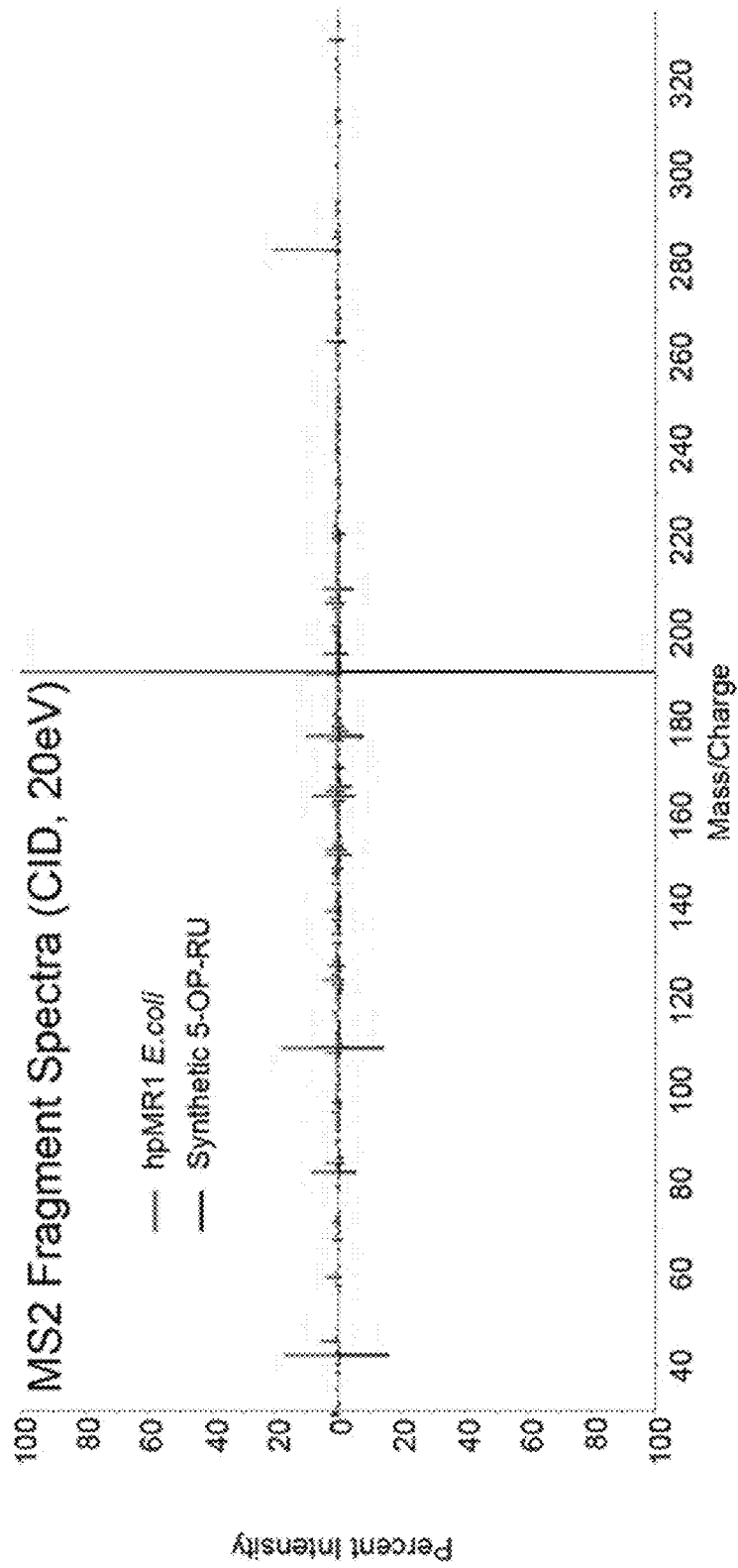
FIG. 7E depicts a MS2 fragment spectra of the precursor ion in indicated sample.
Figure 8A:
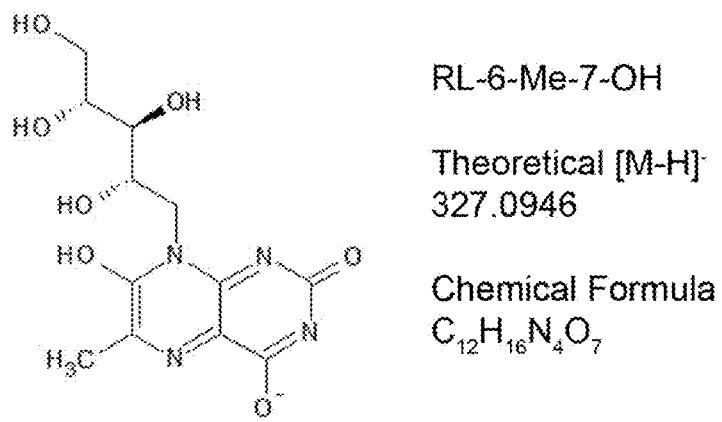
FIG. 8A shows the [M-H]− ion structure, theoretical monoisotopic mass, and chemical formula for RL-6-Me-7-OH.
Figure 8B:
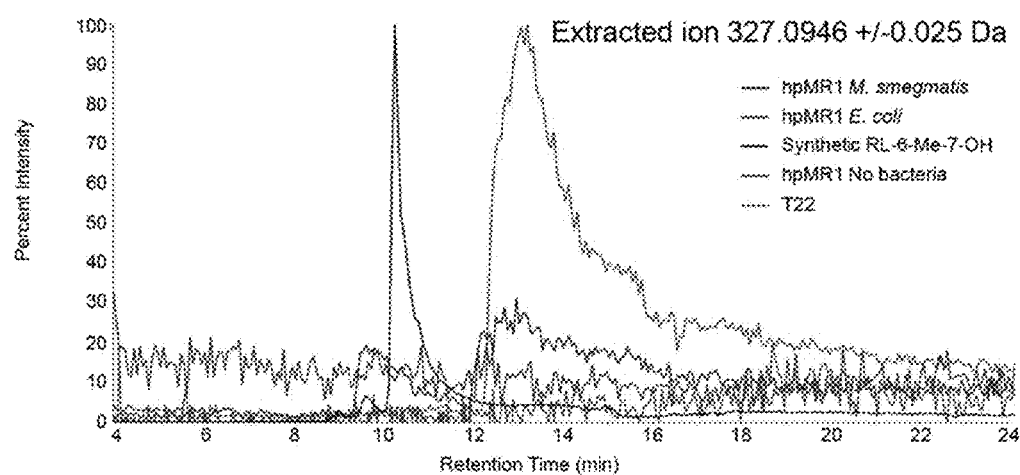
FIG. 8B depicts an extracted ion chromatogram overlay of the theoretical mass of RL-6-Me-7-OH in hpMR1+MS (blue), hpMR1+EC (red), hpMR1-bac (purple), T22 (green), or synthetic RL-6-Me-7-OH (black).
Figure 8C:
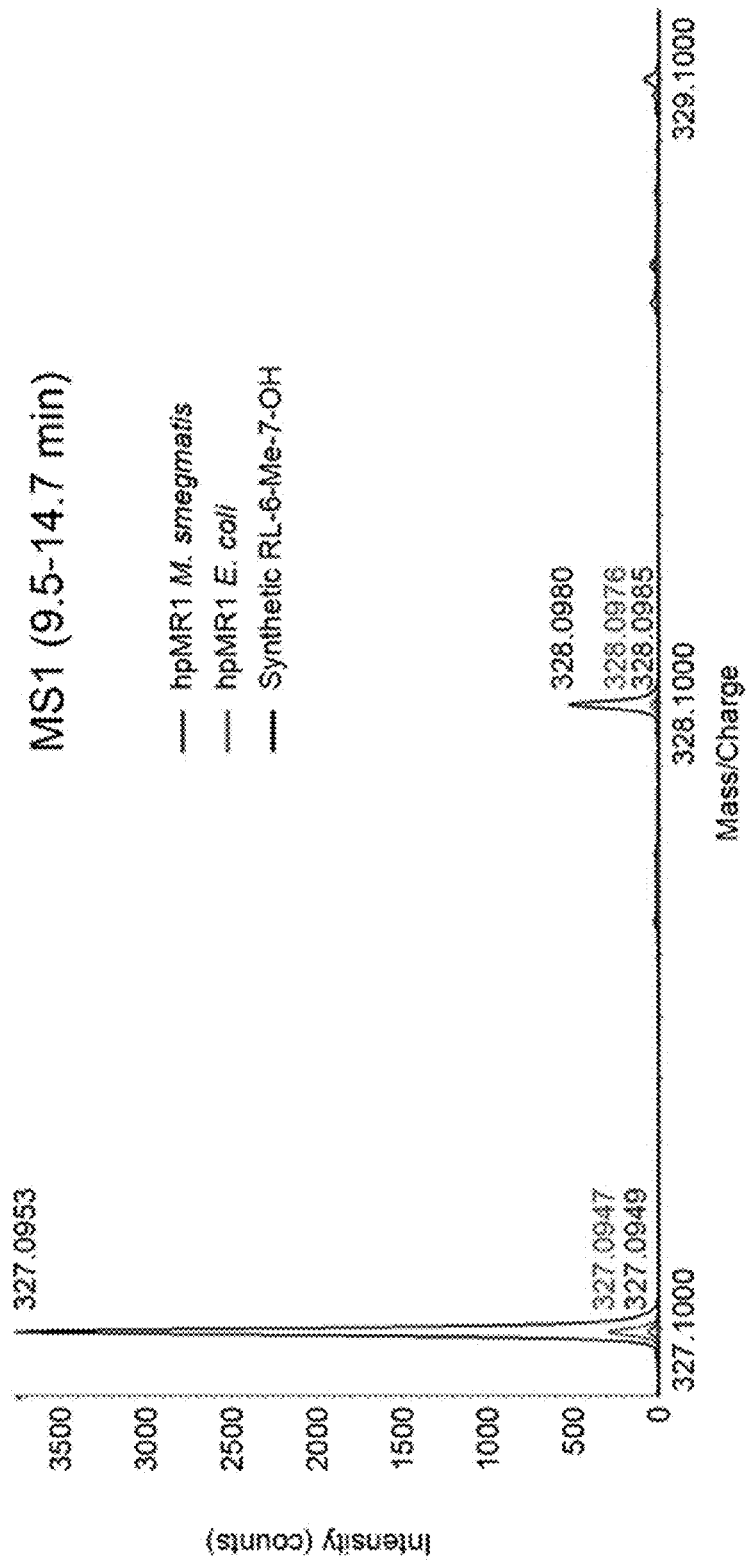
FIG. 8C depicts a MS1 survey spectra overlay of the relevant ion over the indicated retention time range in hpMR1+EC. Observed m/z for the ion and the respective +1 isotope are labeled and color coded to match the sample trace color.
Figure 8E:
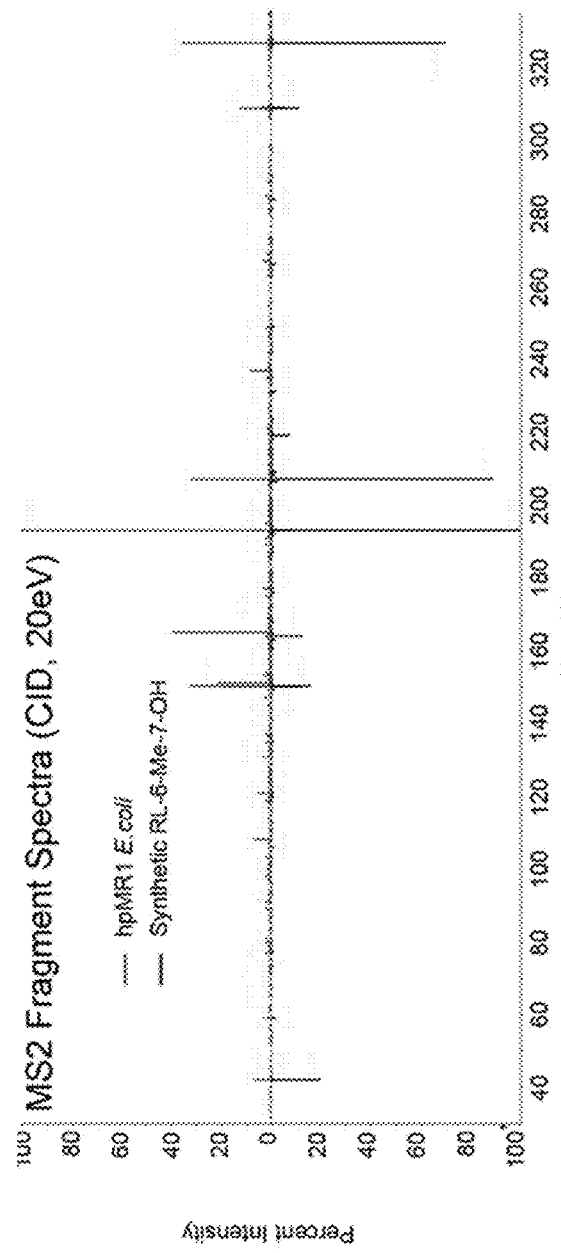
FIG. 8E depicts a MS2 fragment spectra of the precursor ion in indicated sample.

To analyze whether hpMR1-bac, +EC, and +MS were loaded with ligands capable of recognizing MR1T cells, tetrameric hpMR1 were generated. Previously, MR1 tetramers that identify MR1Ts by flow cytometry have been made from MR1 refolded in the presence of either 5-(2-oxopropylideneamino)-6-D-ribityluracil (5-OP-RU) or 5-(2-oxoethylideneamino)-6-D-ribitylaminouracil (5-OE-RU) (Corbett 2014 supra). The disclosed approach produces tetramers comprised of hpMR1 monomers loaded with a heterogeneous population of media-, host cell-, and bacterially-derived ligands generated in the context of infection, and thus represent an unbiased, broad sampling of microbial MR1 ligands. Using a MR1T cell clone, it was demonstrated that hpMR1 tetramers could specifically stain MR1Ts (FIG. 6). Two complementary methods were then used to identify MR1Ts in human peripheral blood mononuclear cells (PBMC) from 15 donors: a) hpMR1+EC tetramer$^+$ staining, and b) TRAV1-2$^+$CD26$^+$CD161$^+$ triple staining.

It has been previously shown that TRAV1-2, CD161, and CD26 are sufficient to identify the same population of functional MAIT cells defined by the MR1 tetramer generated with the canonical 5-OP-RU ligand (Sharma P K et al, *Immunology* 145, 443-453 (2015); incorporated by reference herein; Meermeier 2016 supra).

Figures 1B, 1C:
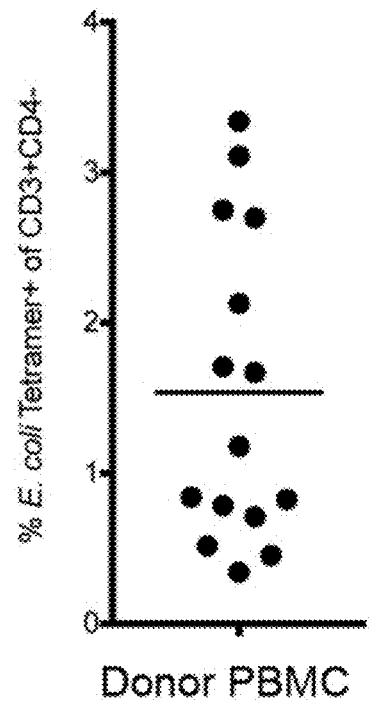
FIG. 1B depicts the frequency of CD3+CD4-hpMR1+EC tetramer+ cells for all 15 PBMC donors (mean: 1.53+/−1.02%; range: 0.35-3.26%).
FIG. 1C depicts the frequency of hpMR1+EC tetramer+ CD26+CD161+ cells.
Figure 1D:
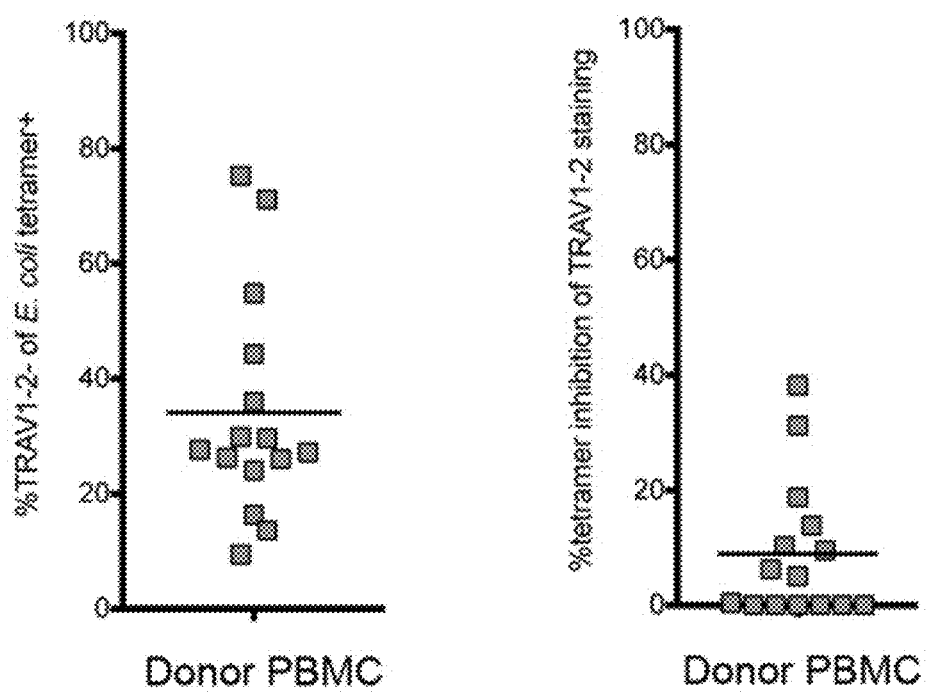
FIG. 1D depicts the frequency of hpMR1+EC tetramer+ TRAV1-2− cells for all 15 PBMC donors.

The hpMR1+EC tetramer could delineate a distinct population of cells in PBMC of each of 15 donors tested (FIGS. 1A-1B). While we previously showed that the MR1/5-OP-RU tetramer stains cells that are nearly entirely TRAV1-2$^+$ (Meermeier 2016 supra), hpMR1+EC tetramer$^+$ cells, while still expressing CD26 and CD161$^+$ (FIG. 1C), were often TRAV1-2 negative (FIGS. 1A, 1D). These data support the hypothesis that MR1T cells, as defined by bacterially-loaded MR1 tetramers, can be distinguished from conventional MAIT cells. Furthermore, hpMR1 tetramers loaded with a heterogenous mixture of microbial ligands may identify MR1T cells that do not express the canonical TRAV1-2 TCR α chain.

Figure 1E:
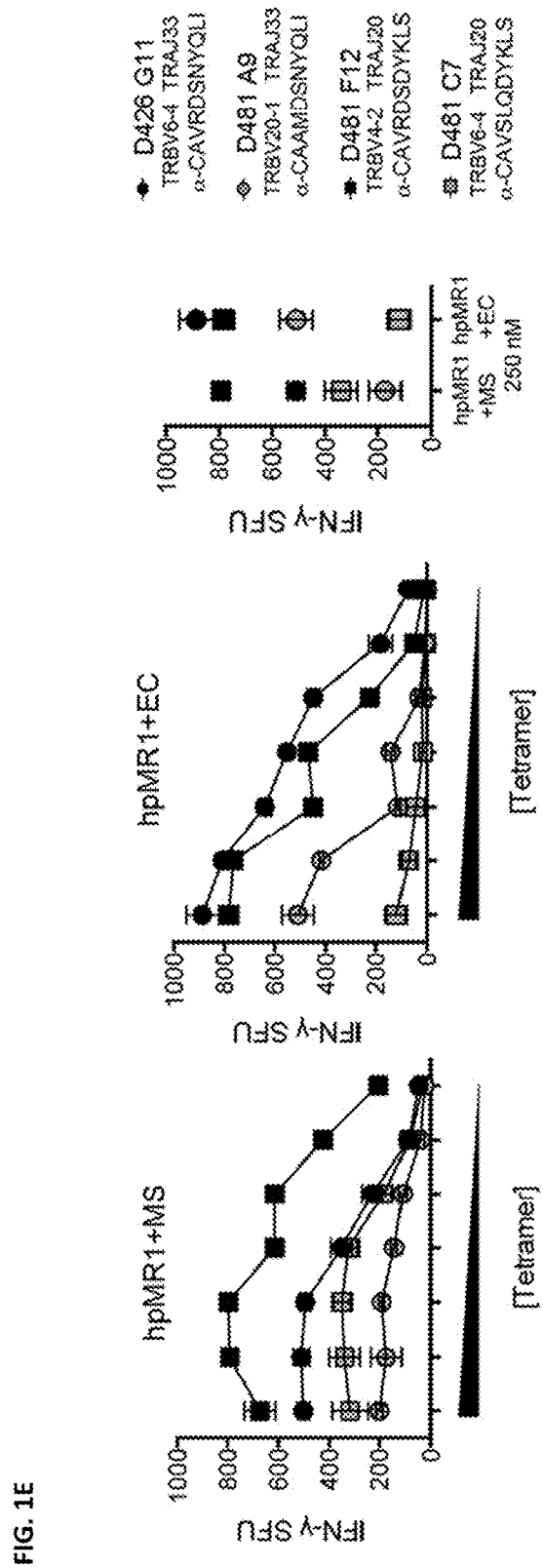
FIG. 1E illustrates MR1T cell clone IFN-γ responses to hpMR1+EC or +MS tetramers at 7.8 ng-500 ng/well. TRBV, TRAJ, and CDR3 sequences are indicated for each MR1T cell clone.
Figure 1F:
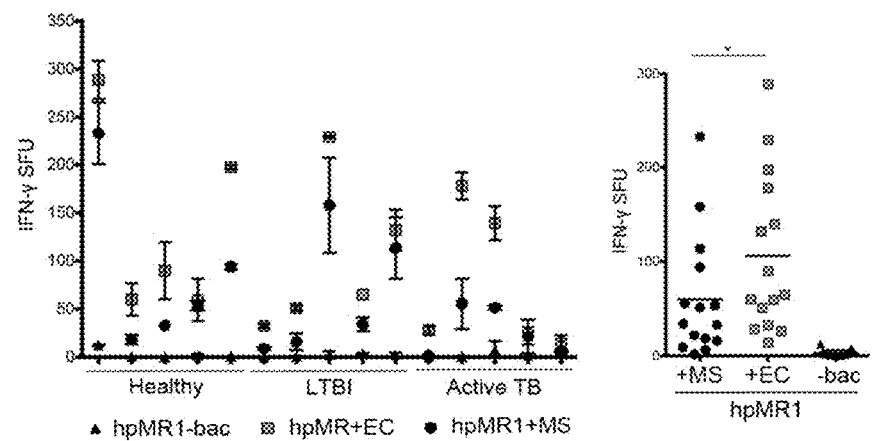
FIG. 1F depicts IFN-γ responses from 5e5 PBMC from donors to hpMR1-bac, +EC (mean: 106+/−81 IFN-γ spot forming units (SFU); range: 14-289 IFN-γ SFU), or +MS tetramers (mean: 60+/−63 IFN-γ SFU; range: 6-123 IFN-γ SFU), plotted by individual donor (left) or pooled (right). $p<0.0^1$.
Figure 1G:
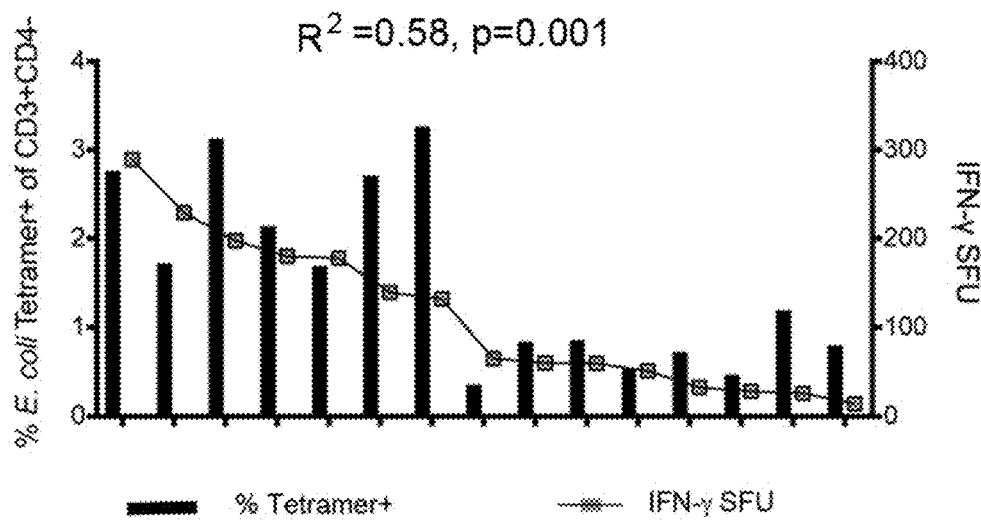
FIG. 1G demonstrates the frequency of CD3+CD4-hpMR1+ECtetramer+ cells identified by flow cytometry is plotted on top of the IFN-γ ELISPOT responses measured for each PBMC donor. $R^2=0.58$, $p=0.001$.

ELISPOT plate-bound hpMR1 tetramers were used to stimulate MR1T cell clones, based on an approach similar to that previously employed for CD1 (Bourgeois E A et al, *J Exp Med* 212, 149-163 (2015); de Jong A et al, *Nat Immunol* 15, 177-185 (2014); incorporated by reference herein), which we termed a tetraSPOT assay. Using the tetraSPOT assay, hpMR1+EC and +MS tetramers robustly stimulated IFN-γ production by a panel of MR1T clones expressing diverse TCR β and TRAJ genes (Gold 2014 supra) (FIG. 1E). Having established the presence of MR1T clone-activating ligands associated with hpMR1, we examined the reactivity of MR1Ts in whole PBMC using the tetraSPOT assay and found that MR1T responses were observed in each of the 15 donors tested (FIG. 1F). While the hpMR1+EC and hpMR1+MS tetramers elicited comparable responses among the MR1T clones (FIG. 1E), activation in PBMC was significantly higher in response to hpMR1+EC compared to hpMR1+MS for every donor tested (FIG. 1F). Overall, the frequency of tetramer$^+$ cells was correlated with the IFN-γ response (FIG. 1G). The differential responses seen between the MR1T clones and directly ex-vivo supports the hypothesis that MR1Ts can discriminate between ligands, which would require diverse TCR usage and the ability of MR1 to present more than one ligand.

Figure 11A:
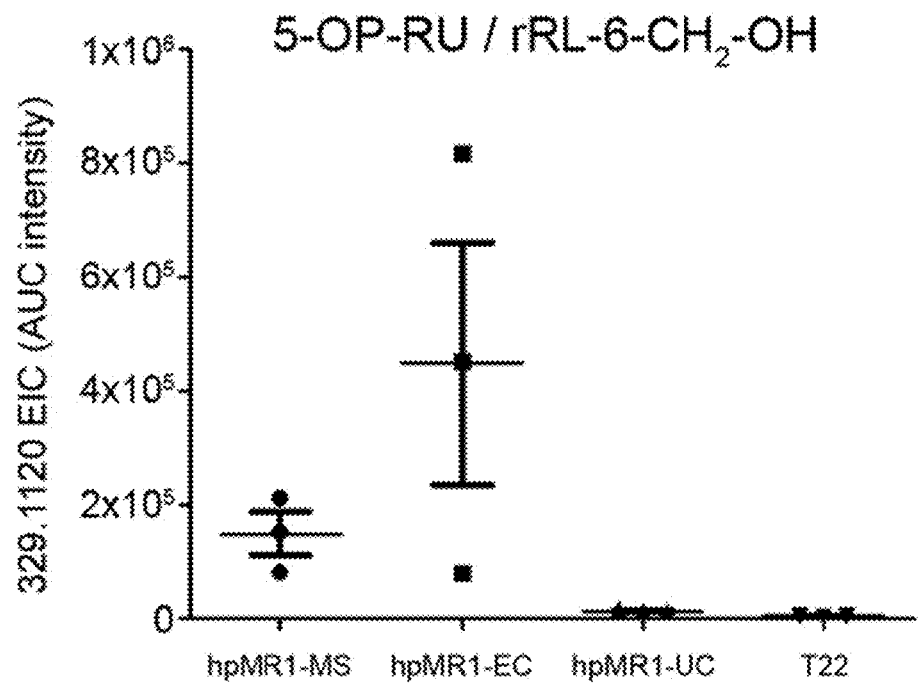
FIG. 11A depicts intensities of previously identified ligands for 5-OP-RU/rRL-6CH2OH. The data originates from triplicate LCMS injections of the same protein preps.
Figure 11B:
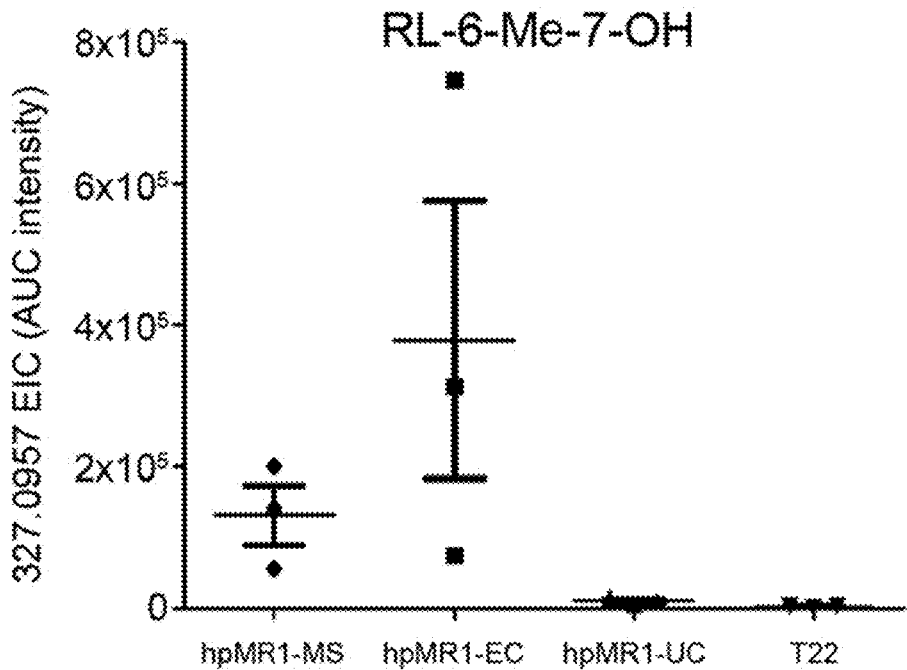
FIG. 11B depicts intensities of previously identified ligands for RL-6-Me-7-OH. The data originates from triplicate LCMS injections of the same protein preps.

The presence and relative abundance of known MR1T ligands was assessed. At present four riboflavin secondary metabolites (5-OP-RU, 5-OE-RU, 7-hydroxy-6-methyl-8-D-ribityllumazine (RL-6-Me-7-OH), and reduced 6-hydroxymethyl-8-D-ribityllumazine (rRL-6-CH$_2$OH)), and the riboflavin biosynthetic precursor 6,7-dimethyl-8-D-ribityllumazine (RL-6,7-diMe) have been identified as activating MR1T ligands. Three of these ligands (5-OP-RU, rRL-6-CH$_2$OH, and RL-6-Me-7-OH) were eluted and identified in hpMR1+EC and +MS but not hpMR1-bac by tandem mass spectrometry (FIGS. 7A, 7B, 7C, 7D, 7E, 8A, 8B, 8C, 8D, 8E), although rRL-6-CH$_2$OH and 5-OP-RU cannot be distinguished because they have identical chemical formulas and fragment spectra. The 5-OE-RU and RL-6,7-diMe ligands (FIGS. 9A, 9B, 10A, 10B, 10C, 10D) were not found in these hpMR1 preparations. Using extracted ion chromatogram area underneath the curve (AUC) analysis, we found that the rRL-6-CH$_2$OH/5-OP-RU and RL-6-Me-7-OH were 3.0- and 2.8-fold lower, respectively, in hpMR1+MS as compared to hpMR1+EC (FIGS. 11A, 11B). These data demonstrate that despite similar activation of MR1T cell clones, there are relative quantitative differences between *E. coli* and *M. smegmatis* in the loading of hpMR1 canonical bacterial ligands.

Figure 2A:
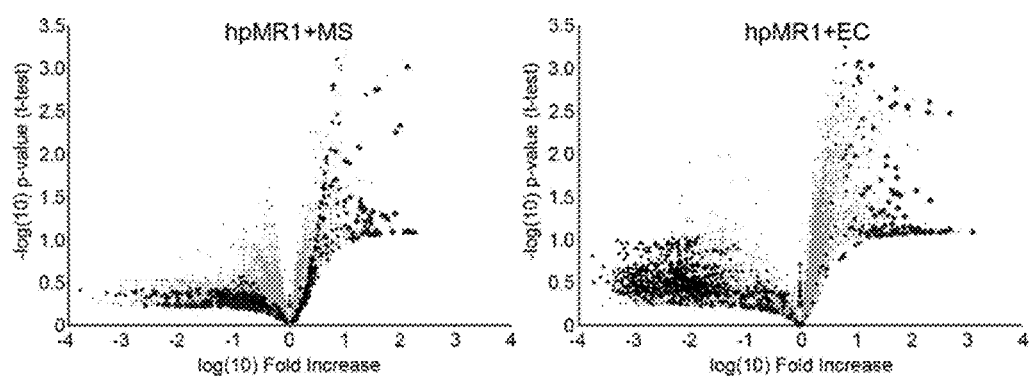
FIG. 2A provides a volcano plot of eluted hpMR1 ions, with all ions plotted for hpMR1+MS (left panel) and hpMR1+EC (right panel).
Figure 2B:
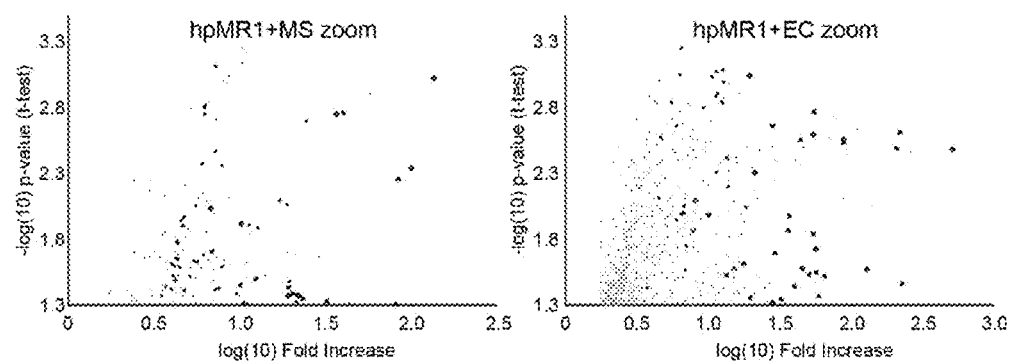
FIG. 2B indicates only significantly ($p<=0.05$, $-\log$ p-value=1.3) increased ions for either hpMR1+MS (left) or +EC (right).

To further explore the MR1 ligandome, all ligands eluted from hpMR1-bac, +EC, and +MS were evaluated using LCMS. Fold increase was calculated for each ion/ligand in either hpMR1+MS or +EC compared to all other samples and plotted on volcano plots (FIG. 2A). As a background control we collected data on the non-MR1 class I MHC molecule T22, which does not present antigen (Adams E J et al, *Science* 308 227-231 (2005); Wang M et al, *Nat Biotechnol* 34 828-837 (2016); both of which are incorporated by reference herein). A total of 970 ions were observed above the T22 background intensity in hpMR1-bac, +EC, or +MS preparations and were considered putative MR1 ligands. Of these, 127 ions were observed at >10-fold increased intensity in hpMR1+EC or +MS compared to hpMR1-bac and were considered putative microbial-derived ligands. Twelve bacteria-derived monoisotopic ions were distinct to hpMR1+MS, and 29 bacteria-derived monoisotopic ions were distinct to hpMR1+EC (FIG. 2B). These data demonstrate that disparate bacterial species produce distinct ligands for MR1.

Figure 3A:
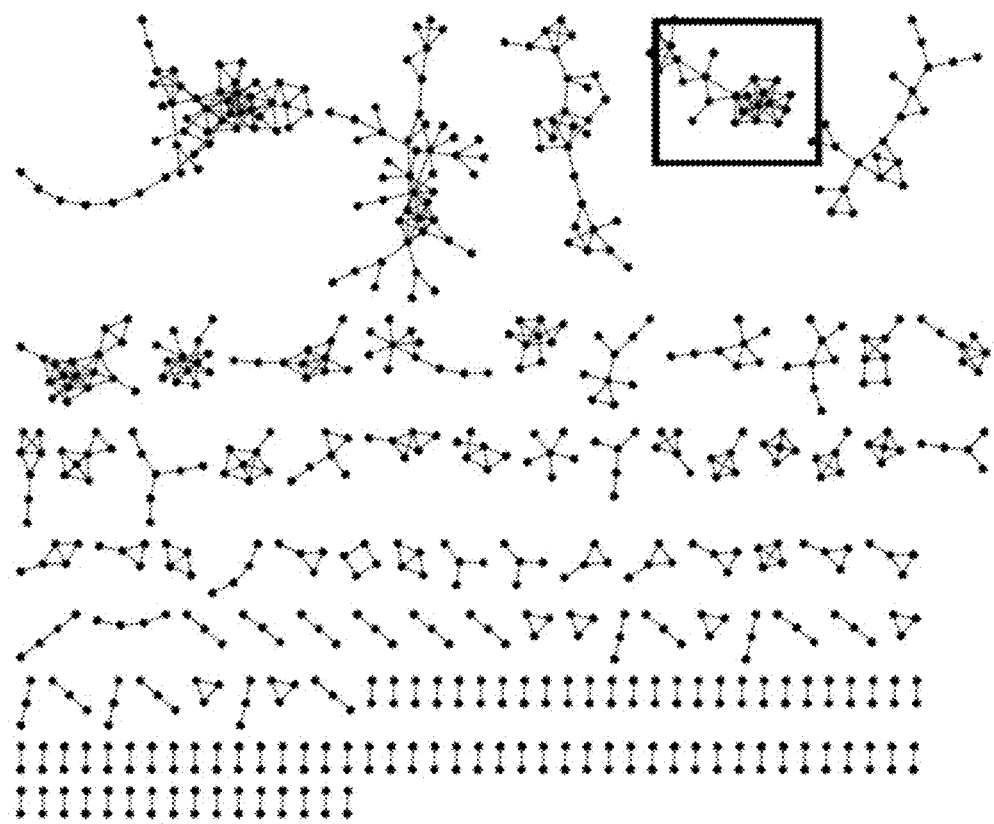
FIG. 3A depicts molecular networking of hpMR1 eluted ions from hpMR1 in a force-directed layout showing clusters ≥2 nodes.
Figure 3B:
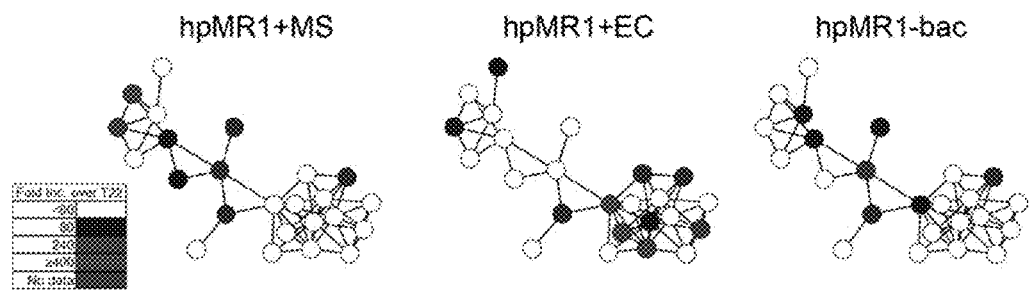
FIG. 3B depicts the relative abundance of ions in the riboflavin cluster in hpMR1+MS (left), hpMR1+EC (center), and hpMR1-bac (right).
Figure 3C:
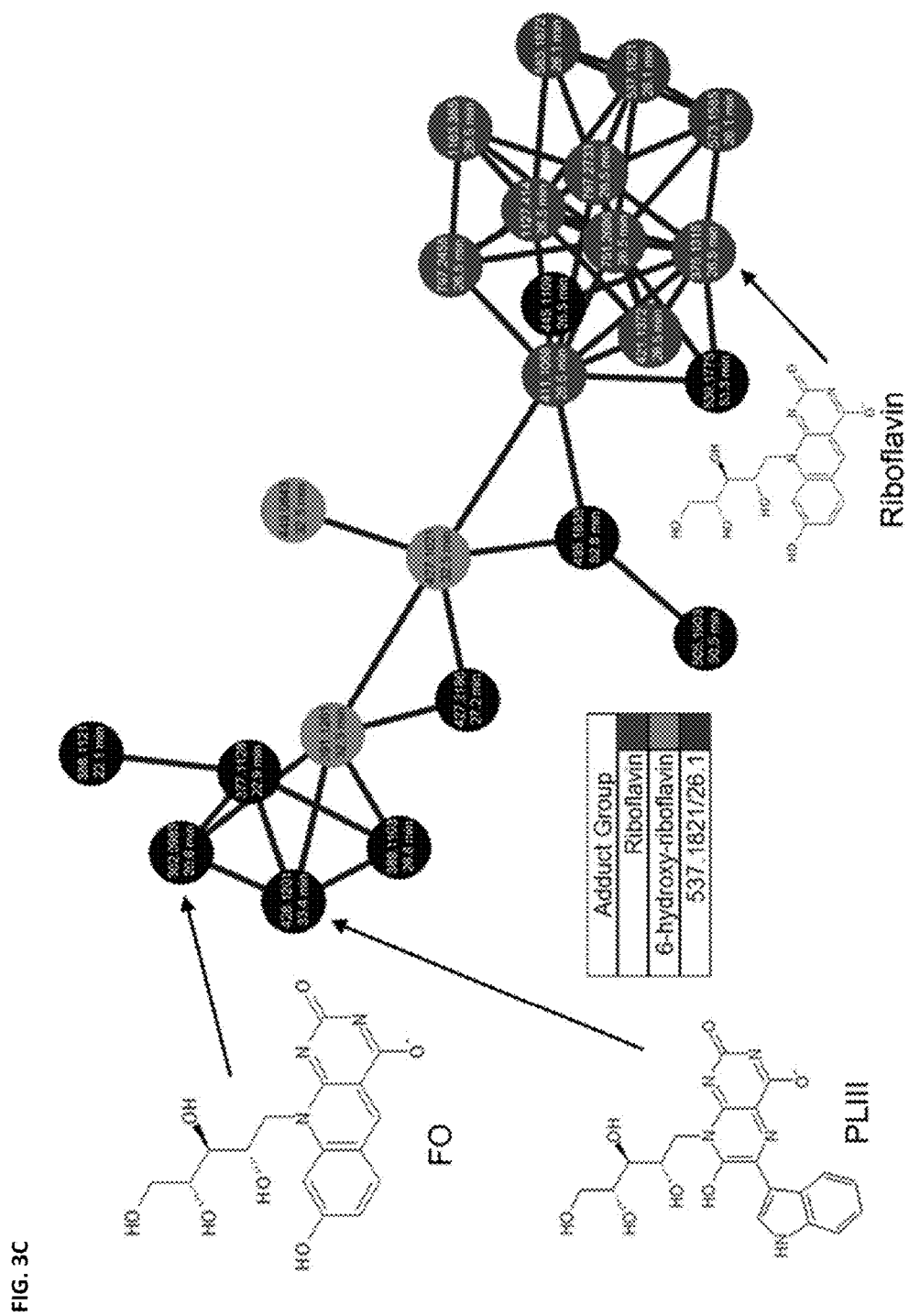
FIG. 3C depicts a detailed image of the riboflavin network, with each node labeled with the average ion m/z and normalized average retention time for that ion.
Figure 3D:
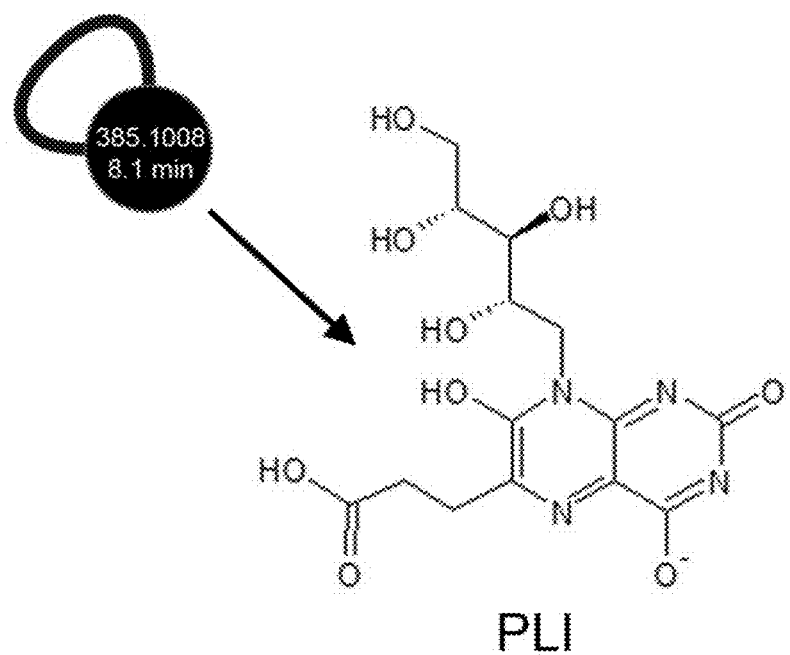
FIG. 3D depicts a single non-clustering node associated with Photolumazine I (PLI: 385.1008/8.1).

Global Natural Products Social Molecular Networking (GNPS) was used to assist in the identification of these novel ligands. Key to this GNPS analysis is that compounds with similar MS2 fragment spectra and molecular structures form clusters. In all, 154 clusters with anywhere from 2 to 48 nodes per cluster (FIG. 3A) were identified, with 1069 ions that could not be clustered. Remarkably, no ions clustered with rRL-6-CH$_2$OH/5-OP-RU (FIGS. 12A, 12B, 12C), and RL-6-Me-7-OH clustered with only one other ion which we identified as acetylated RL-6-Me-7-OH (FIGS. 13A, 13B, 13C, 13D). One large cluster contained two of the most distinct ions for hpMR1+MS (FIG. 3B). Database spectral matching identified riboflavin and several riboflavin adducts or derivatives as constituents of this cluster (FIG. 3C, FIGS. 14A, 14B, 14C, 14D, 14E, 14F, 15A, 15B, 15C, 15D, 15E, 16A, 16B, 16C, 16D, 16E, 17A, 17B, 17C, 17D, 17E). Using mass accurate database searches and comparing fragment spectra, three additional novel MR1 ligands were identified in this cluster. The most prevalent hpMR1+MS-specific ion in the cluster was identified as 7,8-didemethyl-8-hydroxy-5-deazariboflavin (FO) (Bashiri A M et al, *PLoS One* 5, e15803 (2010); incorporated by reference herein) (FIG. 3C, FIGS. 18A, 18B, 18C, 18D). FO is the precursor to coenzyme F$_{420}$, an essential component of methanogenesis. The coenzyme F$_{420}$ biosynthesis pathway is limited to soil-based bacteria such as archaea and some actinobacteria, including mycobacteria, and is rare among normal microbial flora (Selengut J D and Haft D H, *J Bacteriol* 192, 5788-5798 (2010); incorporated by reference herein) FO is generated when 4-hydroxyphenylpyruvate from the tyrosine biosynthesis pathway and 5-amino-6-D-ribitylaminouracil (5-A-RU) from the riboflavin biosynthesis pathway react, catalyzed by the FO synthase enzyme. An ion nearby FO in the riboflavin cluster and present in both hpMR1+EC and +MS was identified as 6-(1H-indol-3-yl)-7-hydroxy-8-ribityllumazine, or photolumazine III (PLIII) (Suzuki A et al, *Bull Chem Soc Japan* 44, 1869-1872 (1971); incorporated by reference herein) (FIG. 3C, FIG. 19A, 19B, 19C, 19D, 19E). Interestingly, another ion unique to hpMR1+MS had similar fragments and neutral loss ions as PLIII and RL-6-Me-7-OH but did not cluster with riboflavin. This ion was identified as 6-(2-carboxyethyl)-7-hydroxy-8-ribityllumazine, or photolumazine I (PLI) (FIG. 3D, FIG. 20A, 20B, 20C, 20D). To confirm the identification of these ligands, riboflavin was obtained and from that was synthesized FO, PLI, and PLIII (FIGS. 14A, 14B, 14C, 14D, 14E, 14F, 15A, 15B, 15C, 15D, 15E, 16A, 16B, 16C, 16D, 16E, 17A, 17B, 17C, 17D, 17E). All confirmed and proposed structures are summarized in Table S3 and FIG. 22.

Figure 4A:
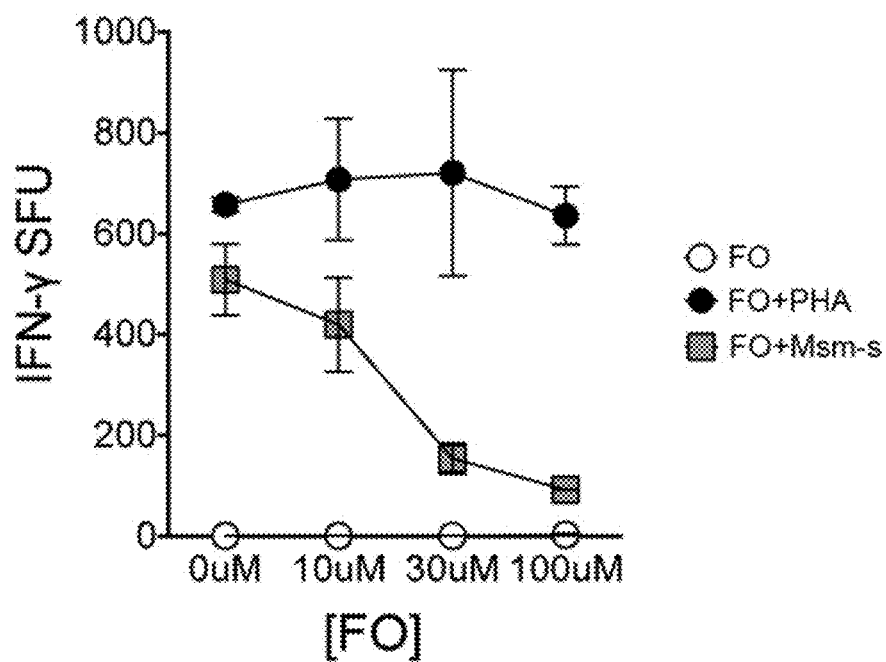
FIG. 4A depicts a graph MR1T cell clone responses to synthetic ligand FO at 3 concentrations prior to addition of *M. smegmatis* supernatant (Msm-s).
Figure 4B:
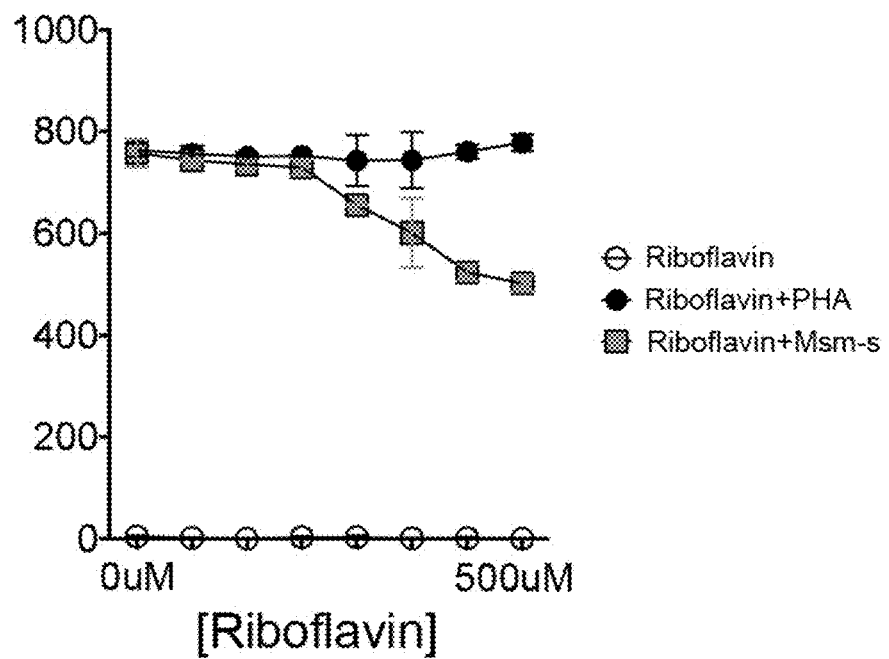
FIG. 4B depicts a graph MR1T cell clone responses to Riboflavin (7.8 µM-500 µM) prior to addition of *M. smegmatis* supernatant (Msm-s) or PHA.
Figure 4C:
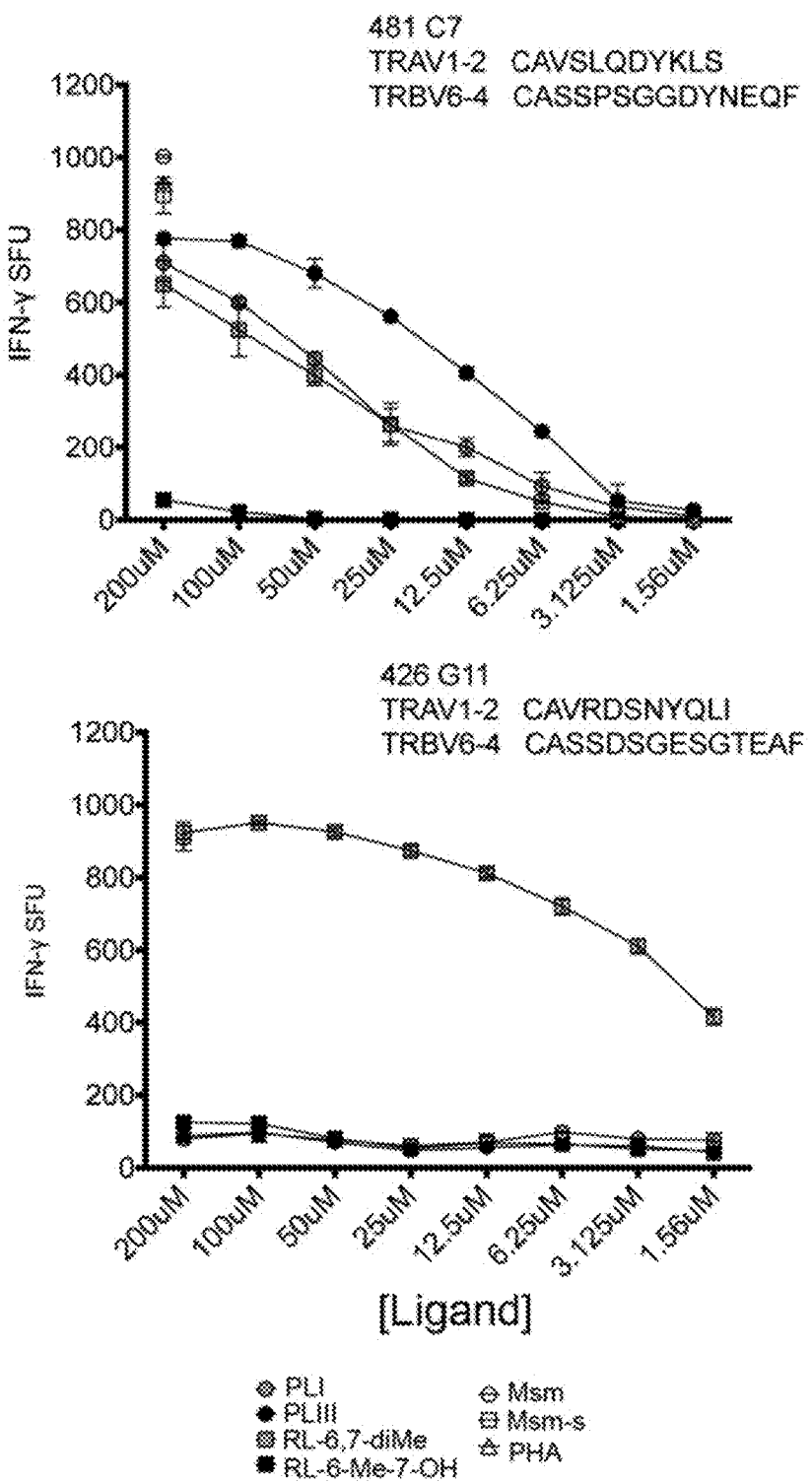
FIG. 4C depicts MR1 cell clone D481 C7 responses to DC incubated with synthetic PLI, PLIII, RL-6,7,-diMe (DMRL), or RL-6-Me-7-OH (HMRL), at 1.56 µM-200 µM, or *M. smegmatis* (Msm), *M. smegmatis* supernatant (Msm-s), or PHA.

To determine whether riboflavin, FO, PLI, and PLIII were antigens, they were tested for their ability to stimulate MR1T clones. Neither riboflavin nor FO was capable of MR1T cell activation. (FIGS. 4A, 4B). The ligand 6-FP antagonizes MR1T activation (Harriff M J et al, *PLoS Pathog* 12, e1005524 (2016); Eckle S B et al, *J Exp Med* 211, 1585-1600 (2014); both of which are incorporated by reference herein). To determine whether riboflavin or FO are also antagonistic, antigen presenting cells (APC) were pre-loaded with riboflavin or FO and then tested for their ability to present antigens from *M. smegmatis* supernatant (Msm-sup) to MR1Ts. Pre-incubation of APC with both riboflavin and FO blocked the MR1T clone response to Msm-sup, and less FO was required to reach 50% inhibition (FIGS. 4A, 4B) suggesting that FO is a more potent antagonist of MR1T activation than riboflavin. In contrast, PLI and PLIII were found to be antigenic. PLI and PLIII were each tested for their ability to stimulate two MR1T clones with distinct TCRs. For MR1T clone D481_C7, PLI and PLIII were potent activating ligands similar to RL-6,7-diMe (FIG. 4C, top). In contrast, there were only modest responses to PLI and PLIII for the D426_G11 clone (FIG. 4C, bottom).

Figure 4D:
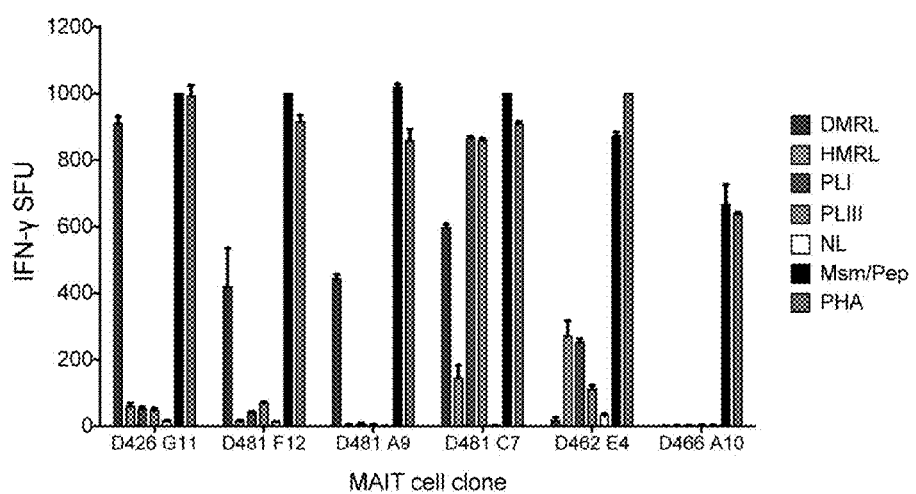
FIG. 4D depicts a panel of MR1T cell clones or an HLA-B45-restricted T cell clone (D466 A10) incubated with 100µM PLI, PLIII, DMRL, or HMRL.

Given the striking differences in response between D481_C7 and D426_G11, we postulated that discrete TCR usage could be associated with ligand discrimination. To test this, an expanded panel of TCR diverse MR1T clones was tested for their ability to recognize each antigen. Every clone responded robustly to APC infected with *M. smegmatis* (FIG. 4D). However, striking differences were observed in the response to the various ligands. For example, while the D481_F12 and D481_A9 MR1T cell clones responded to RL-6,7-diMe, they had modest or no recognition of RL-6-Me-7-OH, PLI, and PLIII. In contrast, the D481_C7 responded to RL-6-Me-7-OH as well as RL-6,7-diMe, PLI, and PLIII. Because TRAV1-2 negative cells were stained with the hpMR1+EC tetramer, we also tested the ability of a recently described TRAV12-2 MR1T cell clone to respond to these ligands. The D462_E4 TRAV12-2 MR1T cell clone had comparable responses to RL-6-Me-7-OH and PLI that were greater than PLIII (FIG. 4D). The TRAV12-2 MR1T cell clone did not respond to RL-6,7-diMe as previously reported. Together, these data demonstrate that discrete MR1T TCRs can distinguish between distinct MR1 antigens.

Within the immune system, T cells respond to perturbations in the intracellular environment. Broadly speaking, conventional MHC-I and MHC-II sample the peptidome, through the processing and presentation of protein antigens, and CD1 samples the microbial cell wall through the processing and presentation of lipids and glycolipids. While MR1 initially was thought to present only riboflavin metabolites, a small portion of the microbial metabolome, this report argues for greater antigen diversity for MR1 and a broader sampling of the microbial metabolome. In classical MHC and CD1, specific recognition of the microbial ligand is conferred by selective TCR usage. Early work proposed that MR1Ts use a semi-invariant TCR to sense riboflavin metabolites presented by MR1. However, more recent work has observed greater diversity in the gene usage of TRAV1-2$^+$ MR1T TCRs as well as populations of TRAV1-2$^-$ MR1Ts that are recognized by the 5-OP-RU and 6-FP MR1 tetramers and also recognize infection with *S. pyogenes*, a pathogen that cannot synthesize riboflavin. While we have focused on *E. coli* and *M. smegmatis* in this report, we would predict that the selective TCR usage associated with microbes such as *C. albicans* or *S. pyogenes* will in turn be associated with MR1 ligands unique to these microbes. We note that the MR1/5-OP-RU tetramer stains all of the diverse TCR clones used in this report, and hence does not serve to define the ligand specificity of these clones. This contrasts with MHCI/II tetramers, but offers parallels to what has been observed using αGalCer CD1d tetramers, which mask underlying ligand discrimination. Defining how MR1Ts distinguish these distinct small molecules requires structural analysis. One implication of these findings is that the selective expansion or maintenance of MR1T cells with microbial selectivity could be harnessed in immunotherapeutic or vaccination strategies. In this regard, it is not yet known whether MR1T cells have immunologic memory, defined by expansion and retention of antigen-selective T cells.

Disclosed herein is work reflecting the diversity of ligands bound by MR1 in the context of infection with different microbes. MR1 ligand diversity is detected by MR1T cells, as MR1 tetramers loaded with multiple bacterial ligands were broadly recognized by MR1T clones with distinct TCR arrangements and by PBMC from a panel of donors. Mass spectrometric analysis of microbially-derived MR1 ligands revealed diversity and GNPS analysis resulted in the identification of both shared and unique as well as previously unknown ligands. Testing of riboflavin, FO, PLI and PLIII confirmed these molecules as novel MR1 ligands and revealed selective recognition of these ligands by MR1Ts with distinct TCRs. While previous work has only identified a few riboflavin metabolites as activating MR1Ts, our results establishes that MR1 samples the broader microbial metabolome similar to how conventional MHC molecules sample the microbial peptidome and CD1 molecules sample microbial lipids and glycolipids.

Specific recognition of and discrimination among the broad array of peptides presented by conventional MHCs and of lipids presented by CD1 requires diverse TCR gene usage, which MR1Ts were originally thought to lack. However, recent work has observed greater diversity in MR1T TCRs, which could provide the diversity for broad MR1 ligand recognition and discrimination required. Indeed, greater diversity in MR1T gene usage was recently observed in TRAV1-2$^+$ MR1T TCRs, and populations of TRAV1-2$^-$ T cells that are recognized by MR1 tetramers and respond to infection with *S. pyogenes*, a pathogen that cannot synthesize riboflavin, have been discovered. Worth noting is that the MR1/5-OP-RU tetramer stains all of the diverse TCR clones used in this report and hence does not serve to define the ligand specificity of these clones. Reliance solely on this reagent for identification of MAIT cells could mask underlying ligand discrimination similar to observations using CD1d/αGalCer tetramers.

These results provoke many exciting avenues to further explore MR1T function and ligand recognition. Since this work found MR1 ligands that are unique to *E. coli* and *M. smegmatis* and found MR1T discrimination between those ligands, one can predict that the selective TCR usage associated with microbes such as *C. albicans* or *S. pyogenes* indicates the existence of MR1 ligands that are unique to these microbes. One unexpected result was the observation that both *E. coli* and mycobacteria generate inhibitory and activating MR1 ligands. The ability of bacteria to generate inhibitory MR1 ligands suggests that MR1T recognition may reflect a balance between these competing ligands. The disclosed results also raise the question of the molecular basis for the selective ligand recognition observed here. The selective expansion or maintenance of MR1T cells with microbial selectivity could be harnessed in immunotherapeutic or vaccination strategies.

TABLE 1

Antibodies used for flow cytometry staining.

| Antibody | Fluorochrome | Clone | Supplier |
| --- | --- | --- | --- |
| CD26 | FITC | BA5b | Biolegend |
| TRAV1-2 | APC | OFA12 | Biolegend |
| CD8 | APC-eFluor 780 | SK1 | eBiosciences |
| CD4 | BV421 | OKT4 | Biolegend |
| CD3 | BV650 | OKT3 | Biolegend |
| CD161 | PeCy7 | HP-3G10 | Biolegend |
| hpMR1-tetramer | PE | N/A | N/A |

FIGS. 1A, 1B, 1C, 1D, 1E, 1F, 1G. MR1T cell responses to hpMR1 tetramers. A) PBMC were stained with the hpMR1+EC tetramer at 12.5 nM per test and a panel of phenotypic markers. Representative dot plots for three donors are shown. Top: the red box denotes the frequency of $CD3^+CD4^-$hpMR1+EC Tetramer$^+$ cells; Middle: TRAV1-2 staining of hpMR1+EC Tetramer$^+$ cells; Bottom: CD26 and CD161$^+$ staining of hpMR1+EC tetramer$^+$ cells. B) The graph depicts the frequency of $CD3^+CD4^-$hpMR1+EC tetramer$^+$ cells for all 15 PBMC donors (mean: 1.53+/−1.02%; range: 0.35-3.26%). C) The graph depicts the frequency of hpMR1+EC tetramer$^+CD26^+CD161^+$cells. D) Left: The graph depicts the frequency of hpMR1+EC Tetramer$^+$ TRAV1-2$^-$ cells for all 15 PBMC donors (mean: 34.1+/−19.5%). Right: The frequency of TRAV1-2$^+$CD26$^+$ CD161$^+$ triple staining cells was compared in samples with or without hpMR1+EC tetramer to determine the impact of hpMR1+EC tetramer staining on TRAV1-2 staining. E) MR1T cell clone IFN-γ responses to hpMR1+EC or +MS tetramers at 7.8 ng-500 ng/well. TRBV, TRAJ, and CDR3 sequences are indicated for each MR1T cell clone. F) IFN-γ responses from 5e5 PBMC from donors to hpMR1-bac, +EC (mean: 106+/−81 IFN-γ spot forming units (SFU); range: 14-289 IFN-γ SFU), or +MS tetramers (mean: 60+/−63 IFN-γ SFU; range: 6-123 IFN-γ SFU), plotted by individual donor (left) or pooled (right). p<0.01. G) The frequency of $CD3^+CD4^-$hpMR1+EC tetramer$^+$ cells identified by flow cytometry is plotted on top of the IFN-γ ELISPOT responses measured for each PBMC donor. $R^2$=0.58, p=0.001.

FIGS. 2A, 2B Volcano plots of eluted hpMR1 ions. Intensities from all observed MS1 ions in triplicate injections of hpMR1+MS, +EC, -bac, and T22 were determined using extracted ion area-underneath-the curve analysis. hpMR1 ions with an average intensity <=80 fold increase over T22 were considered background ions (grey dots). hpMR1 ions with an average intensity >80 fold increase over T22 were considered putative MR1 ligands (black dots). If an hpMR1+MS or +EC ligand was >10 fold increase from hpMR1-bac, it was considered a bacteria-derived MR1 ligand (blue). For all ions, average intensities in hpMR1+MS (left panels) and +EC (right panels) all ions were compared to the combined average intensity of all other samples and is plotted as the log(10) of the fold-increase. P-values were obtained with a t-test and plotted as the inverse log(10). The plot of all ions is shown for hpMR1+MS (left panel) and hpMR1+EC (right panel) in A). B) Indicates only significantly (p<=0.05, −log p-value=1.3) increased ions for either hpMR1+MS (left) or +EC (right).

FIGS. 3A, 3B, 3C, 3D: Molecular networking of hpMR1 eluted ions. A) Molecular network of ions eluted from hpMR1 in a force-directed layout showing clusters ≥2 nodes. Each black node represents an ion MS2 fragment spectra connected by a blue edge based on spectral similarity. The black outline denotes the riboflavin cluster shown in detail in B) and C). B) Relative abundance of ions in the riboflavin cluster. The three panels show the abundance of the ion in hpMR1+MS (left), hpMR1+EC (center), and hpMR1-bac (right). Each node is colored based on the fold increase over T22 in each respective hpMR1 sample according to the legend inlay. C) Detailed image of the riboflavin network. Each node is labeled with the average ion m/z and normalized average retention time for that ion. Ion structures and names are shown associated with nodes where a structure has been determined (FO: 362.0983/20.6), Photolumazine III (PLIII: 428.1201/33.4), and Riboflavin (375.1315/26.5)). Green nodes are ions that are adducts of riboflavin. Pink nodes are ions that are adducts of ion 391.1261/32.5. Brown nodes are ions that are adducts of ion 537.1821/26.1. Black nodes are have no other adducts in the cluster. D) Single non-clustering node associated with Photolumazine I (PLI: 385.1008/8.1).

FIGS. 4A, 4B, 4C, 4D: MR1T cell responses to synthetic ligands. A-B) MR1T cell clone D426 G11 responses to BEAS-2B cells incubated with FO (A, 10 μM, 30 μM, or 100 μM), or Riboflavin (B, 7.8 μM-500 μM) prior to addition of M. smegmatis supernatant (Msm-s) or PHA. C) MR1 cell clone D481 C7 responses to DC incubated with synthetic PLI, PLIII, RL-6,7,-diMe (DMRL), or RL-6-Me-7-OH (HMRL), at 1.56μM-200μM, or M. smegmatis (Msm), M. smegmatis supernatant (Msm-s), or PHA. D) Panel of MR1T cell clones or an HLA-B45-restricted T cell clone (D466 A10) incubated with 100 μM PLI, PLIII, DMRL, or HMRL.

FIGS. 5A, 5B, 5C, 5D. Expression and validation of hpMR1. (A) Schematic representation of hpMR1 construct. Human MR1 sequence is represented in blue and bovine MR1 sequence is represented in pink. Also shown is the structure of MR1 (PDB: 4LCC) colored to match the schematic of the hpMR1 construct. (B) Size exclusion chromatography of hpMR1-bac and hpMR1+EC and SDS-PAGE of fractions from the purification. Bars represent the fractions that were collected and run on an SDS-PAGE gel. (C) Bio-layer interferometry analysis of the F7 MAIT TCR binding to hpMR1-bac or hpMR1+EC. Biotinylated hpMR1-bac or +EC was immobilized on a streptavidin biosensor followed by running increasing concentrations of the F7 MAIT TCR from 0 to 64 μM. Buffer alone (0 μM TCR) was subtracted from each, and the subtracted equilibrium binding was plotted against TCR concentration. (D) Concentrated hpMR1-bac, hpMR1+EC, and hpMR1+MS proteins after size exclusion purification are shown. Each protein has a distinctly different color, likely due to the different repertoire of ligands present from the specific bacteria or absence of bacteria.

FIG. 6 hpMR1 tetramer staining of MR1T cell clone. The D426 G11 MR1T cell clone was stained with the hpMR1-bac and +EC tetramers at 12 nM per test or the hpMR1-bac and +MS tetramers at 195 nM per test. The solid light and dark grey histograms represent the hpMR1-bac staining at either concentration.

FIGS. 7A, 7B, 7C, 7D, 7E: Raw LCMS data for 5-OP-RU/rRL-6-CH2OH. A) [M-H]− ion structure, theoretical monoisotopic mass, and chemical formula for 5-OP-RU (left) and rRL-6-CH2—OH (right). B) Extracted ion chromatogram overlay of the theoretical mass of 5-OP-RU/rRL-6CH2OH in hpMR1+MS (blue), hpMR1+EC (red), hpMR1-bac (purple), T22 (green), or synthetic 5-OP-RU (black). C) MS1 survey spectra overlay of relevant ion over the indicated retention time range for each indicated sample. Observed m/z for the ion and the respective +1 isotope are labeled and color coded to match the sample trace color. D,E) MS2 fragment spectra of precursor ion in indicated sample.

FIGS. 8A, 8B, 8C, 8D, 8E: Raw LCMS data for RL-6-Me-7-OH. A) [M-H]− ion structure, theoretical monoisotopic mass, and chemical formula for RL-6-Me-7-OH. (B) Extracted ion chromatogram overlay of the theoretical mass of RL-6-Me-7-OH in hpMR1+MS (blue), hpMR1+EC (red), hpMR1-bac (purple), T22 (green), or synthetic RL-6-Me-7-OH (black). C) MS1 survey spectra overlay of relevant ion over the indicated retention time range for each indicated sample. Observed m/z for the ion and the respective +1 isotope are labeled and color coded to match the sample trace color. D,E) MS2 fragment spectra of precursor ion in indicated sample.

Figure 9A:
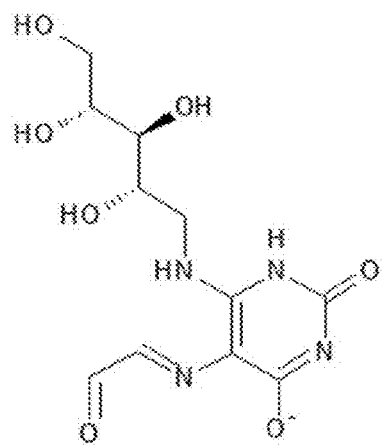
FIG. 9A shows the [M-H]− ion structure, theoretical monoisotopic mass, and chemical formula for 5-OE-RU.
Figure 9B:
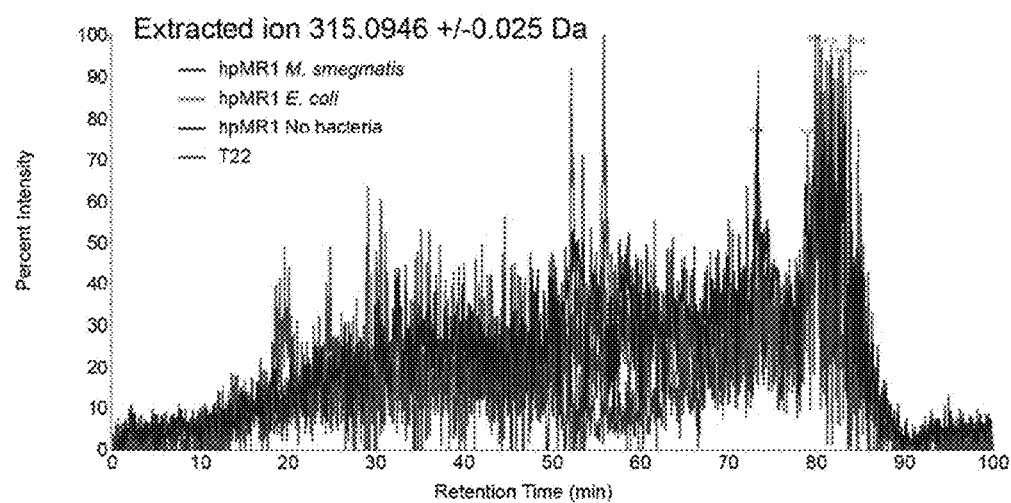
FIG. 9B depicts an extracted ion chromatogram overlay of the theoretical mass of 5-OE-RU in hpMR1+MS (blue), hpMR1+EC (red), hpMR1-bac (purple), or T22 (green).
Figure 10A:
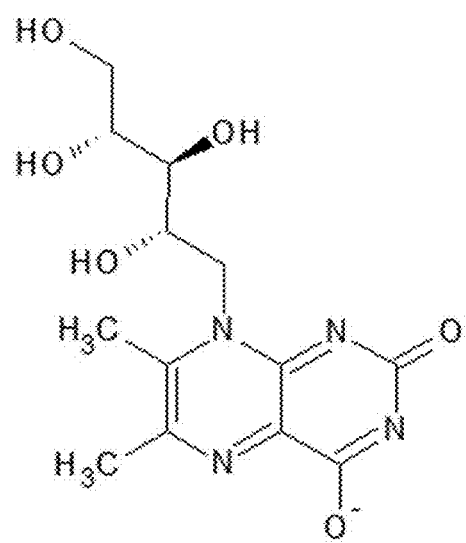
FIG. 10A shows the [M-H]− ion structure, theoretical monoisotopic mass, and chemical formula for RL-6,7-diMe.
Figure 10B:
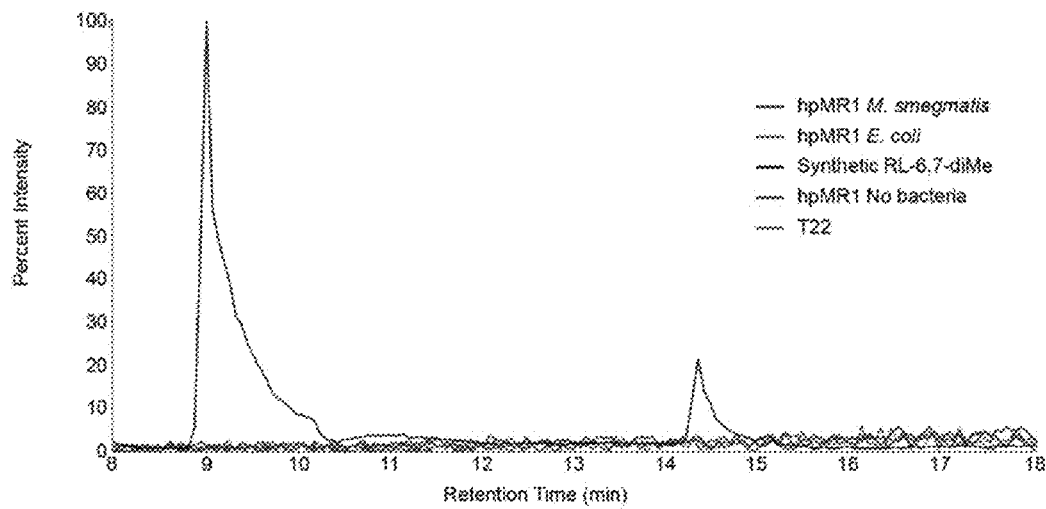
FIG. 10B depicts an extracted ion chromatogram overlay of the theoretical mass of RL-6,7-diMe (blue), hpMR1+EC (red), hpMR1-bac (purple), T22 (green), or synthetic RL-6,7-diMe (black).
Figure 10C:
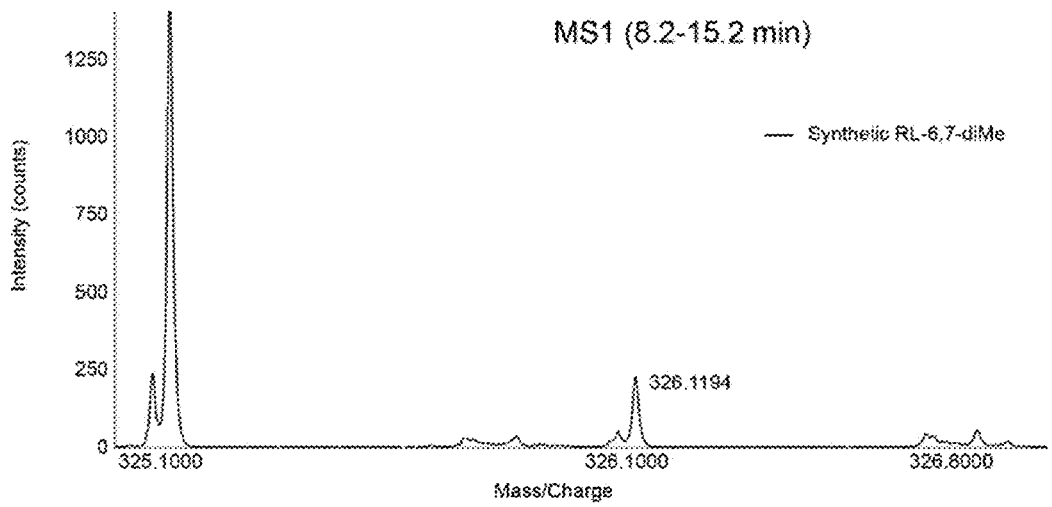
FIG. 10C depicts a MS1 survey spectra overlay of the relevant ion over the indicated retention time range for each indicated sample. Observed m/z for the ion and the respective +1 isotope are labeled and color coded to match the sample trace color.
Figure 10D:
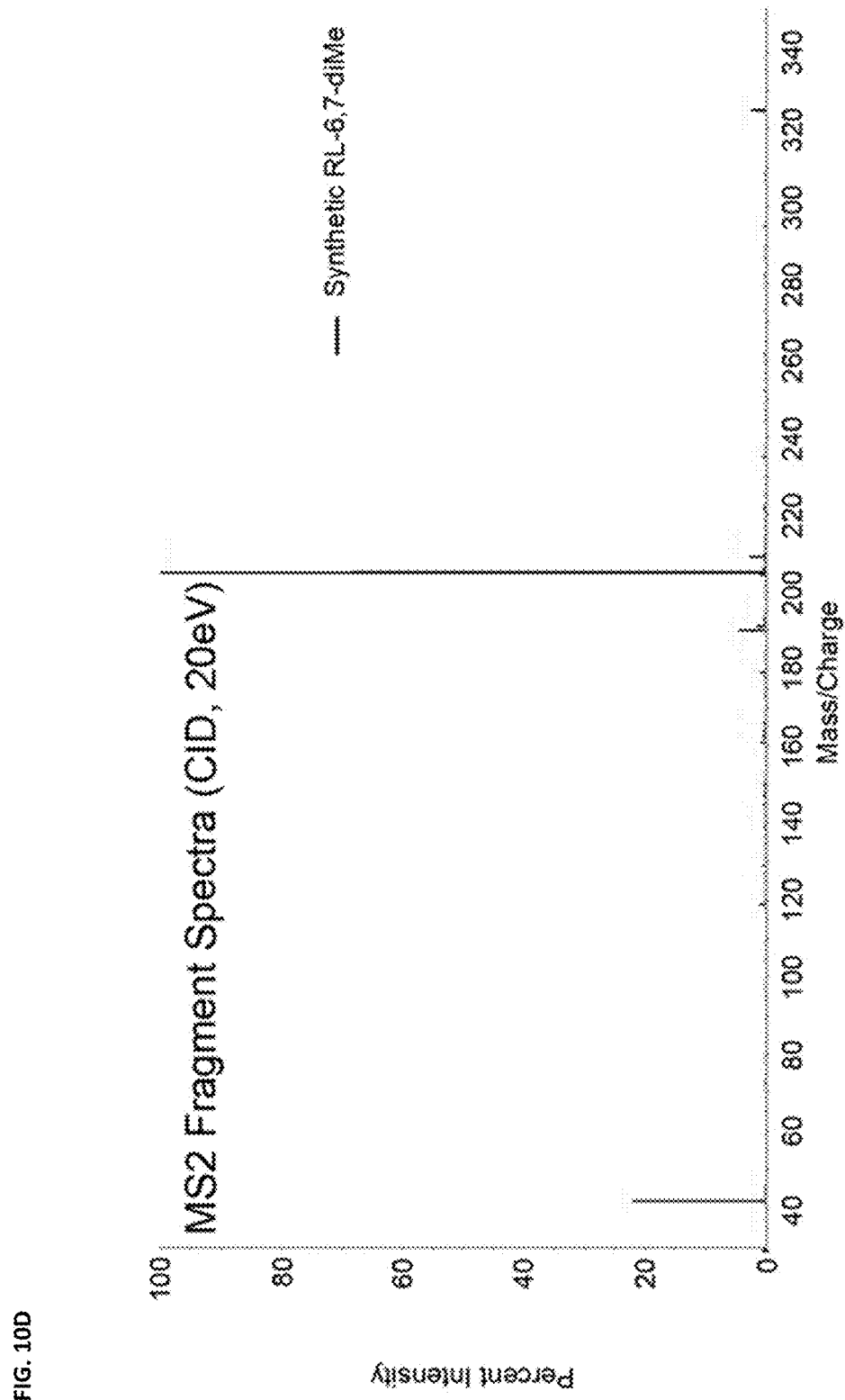
FIG. 10D depicts a MS2 fragment spectra of the precursor ion in indicated sample.

FIGS. 9A, 9B: Raw LCMS data for 5-OE-RU. A) [M-H]− ion structure, theoretical monoisotopic mass, and chemical formula for 5-OE-RU. B) Extracted ion chromatogram overlay of the theoretical mass of 5-OE-RU in hpMR1+MS (blue), hpMR1+EC (red), hpMR1-bac (purple), or T22 (green).

FIGS. 10A, 10B, 10C, 10D: Raw LCMS data for RL-6,7-diMe. A) [M-H]− ion structure, theoretical monoisotopic mass, and chemical formula for RL-6,7-diMe. B) Extracted ion chromatogram overlay of the theoretical mass of RL-6,7-diMe in hpMR1+MS (blue), hpMR1+EC (red), hpMR1-bac (purple), T22 (green), or synthetic RL-6,7-diMe (black). C) MS1 survey spectra overlay of relevant ion over the indicated retention time range for each indicated sample. Observed m/z for the ion and the respective +1 isotope are labeled and color coded to match the sample trace color. D) MS2 fragment spectra of precursor ion in indicated sample.

FIGS. 11A, 11B: Intensities of previously identified ligands: for 5-OP-RU/rRL-6CH2OH (A) and RL-6-Me-7-OH (B). Data originates from triplicate LCMS injections of the same protein preps.

Figure 12:
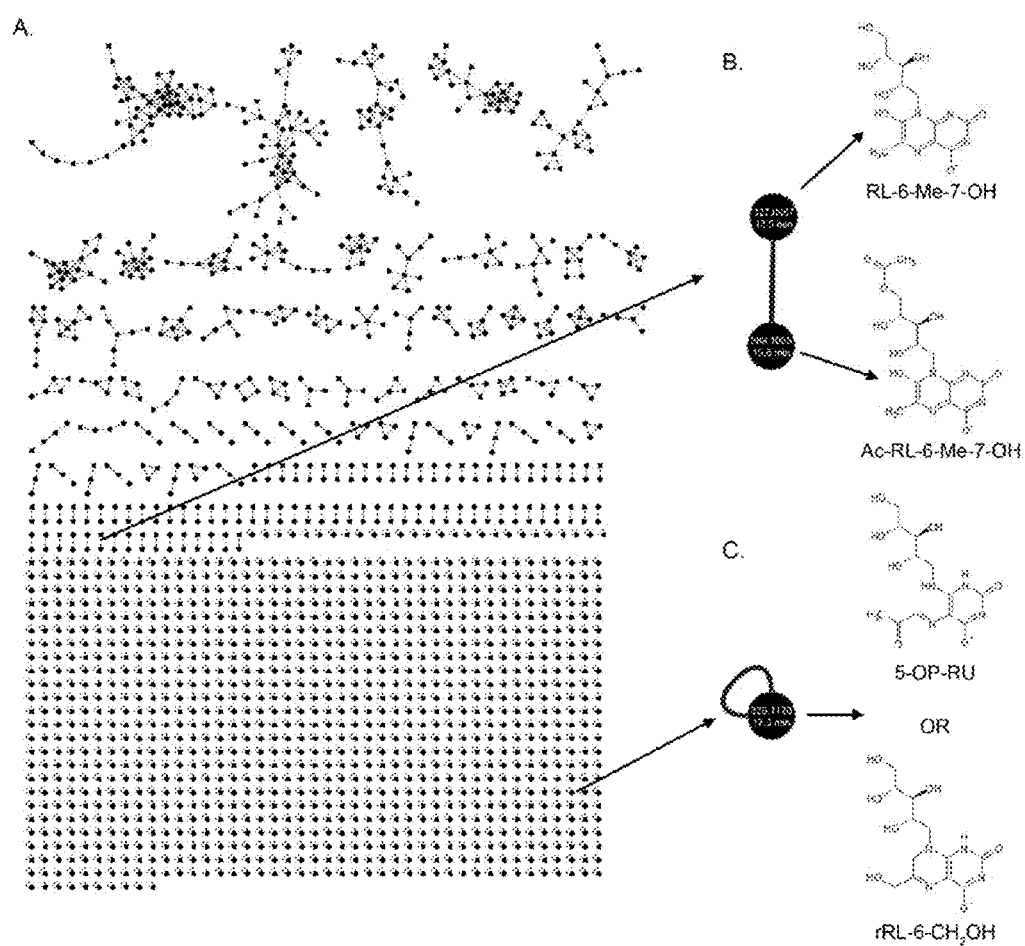
FIG. 12A depicts Complete GNPS molecular network including nodes that clustered with no other node.
FIG. 12B shows detailed information on the RL-6-Me-7-OH cluster, identifying Ac-RL-6-Me-7-OH. The average ion m/z and average normalized retention times are shown for each node.
FIG. 12C shows the node for 5-OP-RU/rRL-6CH2OH that clustered with no other node. The average ion m/z and average normalized retention times are shown for each node.
Figure 13A:
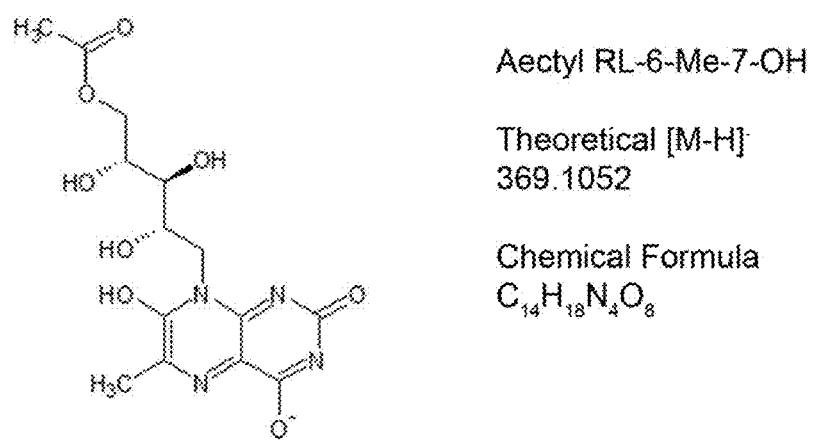
FIG. 13A shows the [M-H]− ion structure, theoretical monoisotopic mass, and chemical formula for Ac-RL-6-Me-7-OH.
Figure 13B:
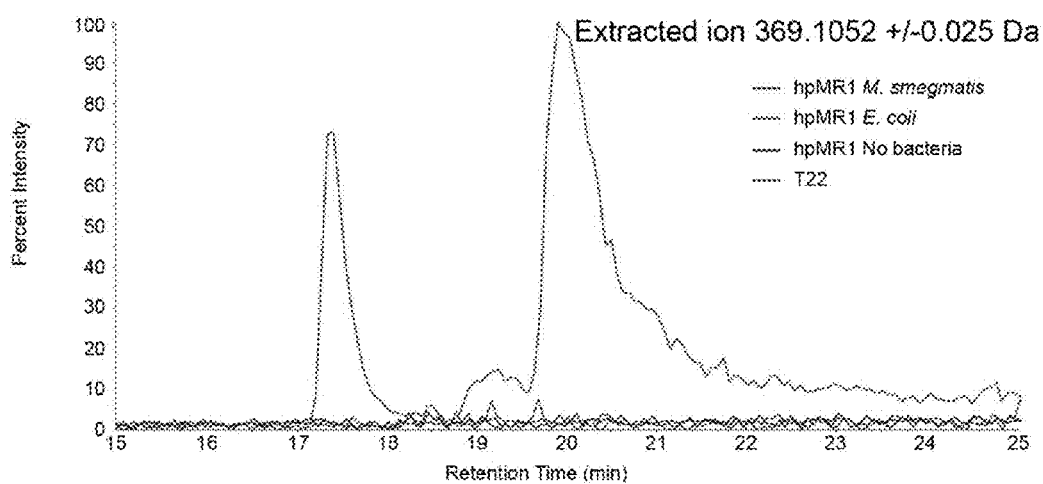
FIG. 13B depicts an extracted ion chromatogram overlay of the theoretical mass of Ac-RL-6-Me-7-OH in hpMR1+MS (blue), hpMR1+EC (red), hpMR1-bac (purple), or T22 (green).
Figure 13C:
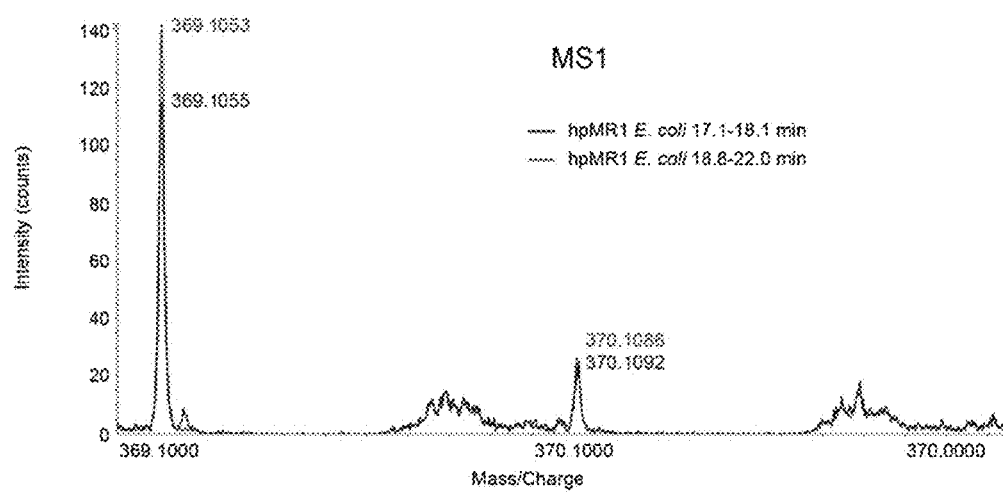
FIG. 13C depicts a MS1 survey spectra overlay of the relevant ion over the indicated retention time range in hpMR1+EC. Observed m/z for the ion and the respective +1 isotope are labeled and color coded to match the sample trace color.
Figure 13D:
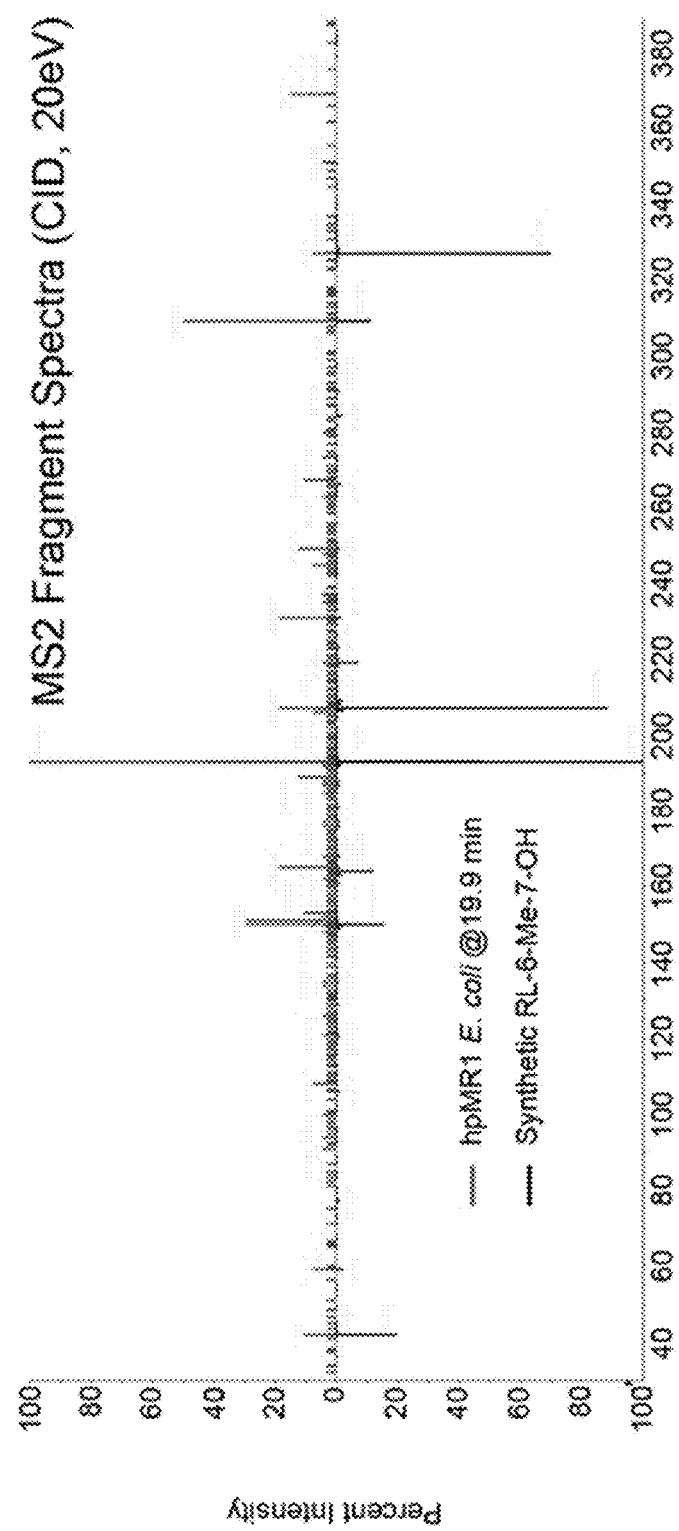
FIG. 13D depicts a MS2 fragment spectra of the precursor ion in indicated sample. The fragment spectra of RL-6-Me-7-OH is shown as a point of comparison.
Figure 14A:
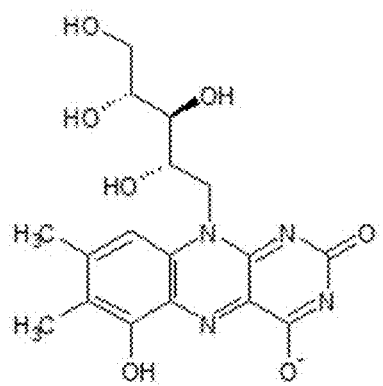
FIG. 14A shows the [M-H]− ion structure, theoretical monoisotopic mass, and chemical formula for 6-hydroxy-riboflavin.
Figure 14B:
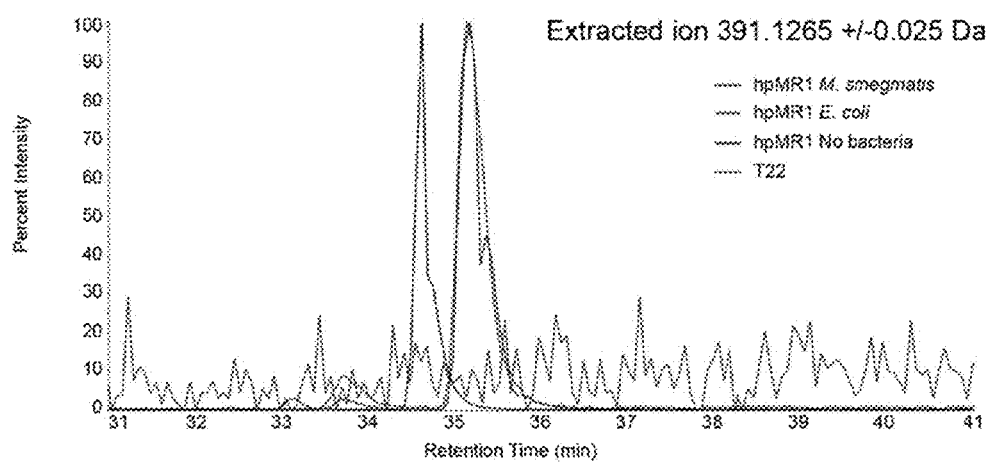
FIG. 14B depicts an extracted ion chromatogram overlay of the theoretical mass of 6-hydroxy-riboflavin in hpMR1+MS (blue), hpMR1+EC (red), hpMR1-bac (purple), or T22 (green).
Figure 14C:
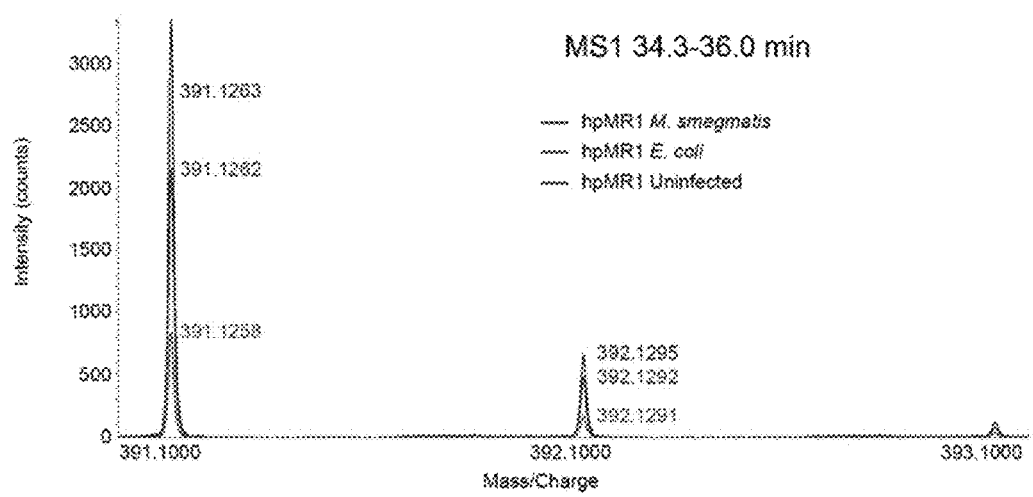
FIG. 14C depicts a MS1 survey spectra overlay of the relevant ion over the indicated retention time range for each indicated sample. Observed m/z for the ion and the respective +1 isotope are labeled and color coded to match the sample trace color.
Figure 14D:
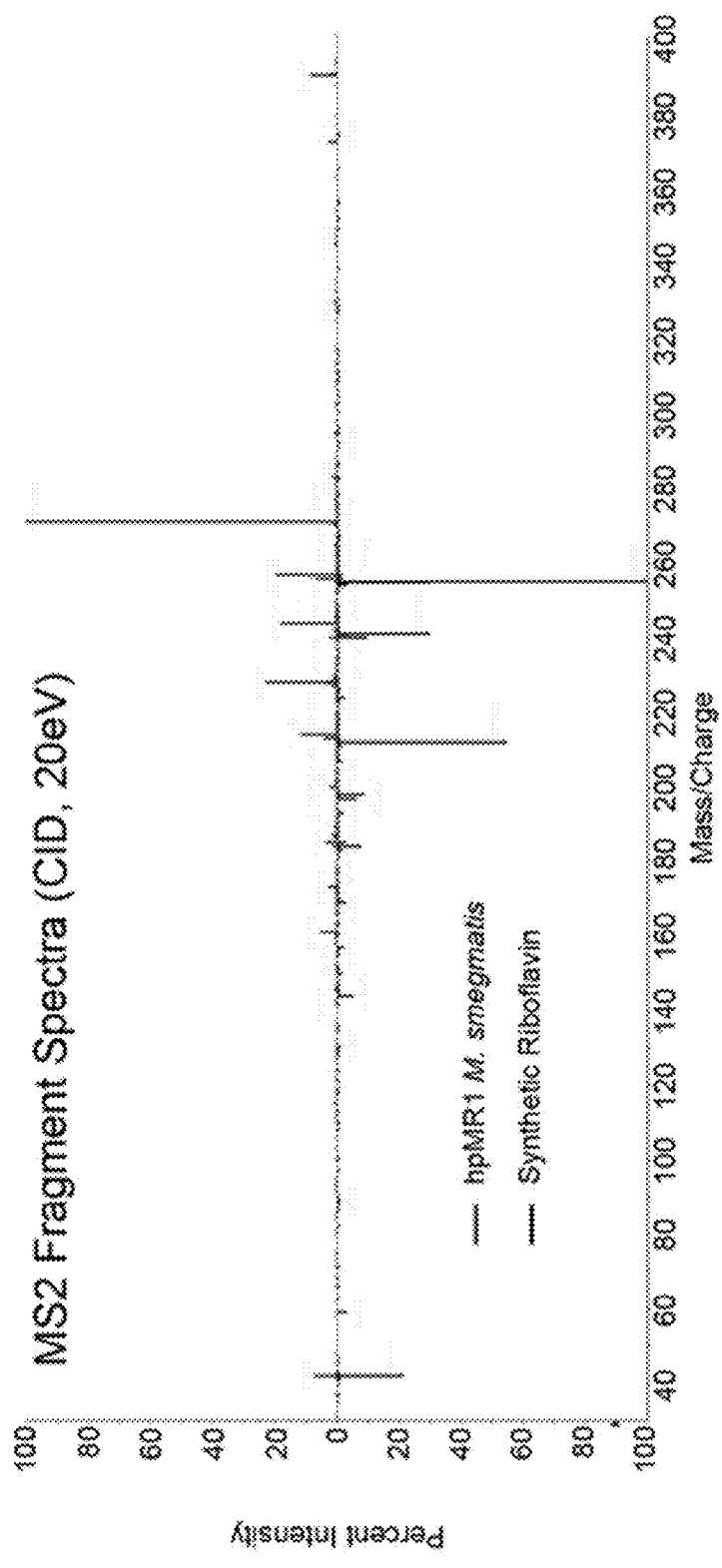
FIG. 14D depicts a MS2 fragment spectra of the precursor ion in indicated sample. The fragment spectra of synthetic riboflavin is shown as a point of comparison.
Figure 14E:
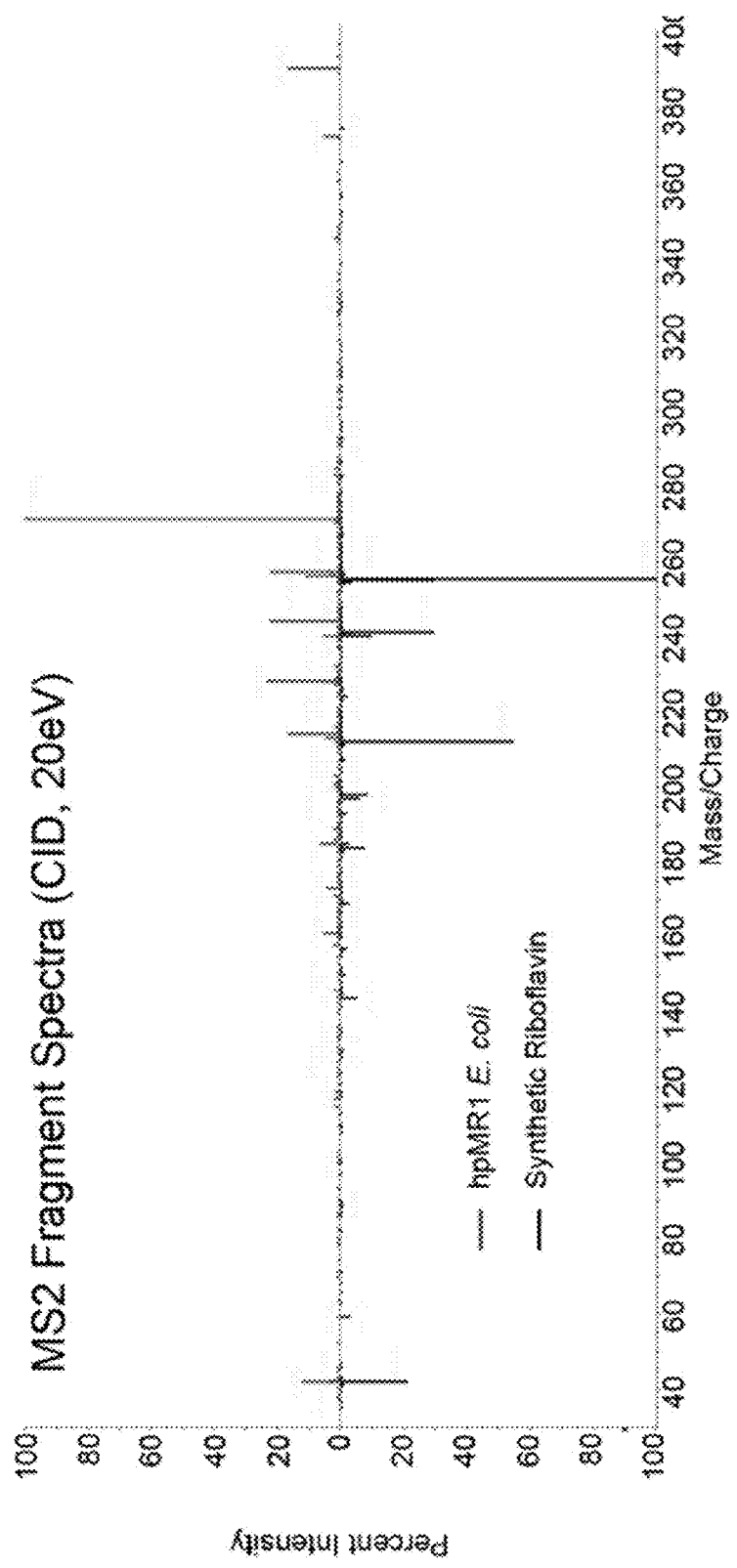
FIG. 14E depicts a MS2 fragment spectra of the precursor ion in indicated sample. The fragment spectra of synthetic riboflavin is shown as a point of comparison.
Figure 14F:
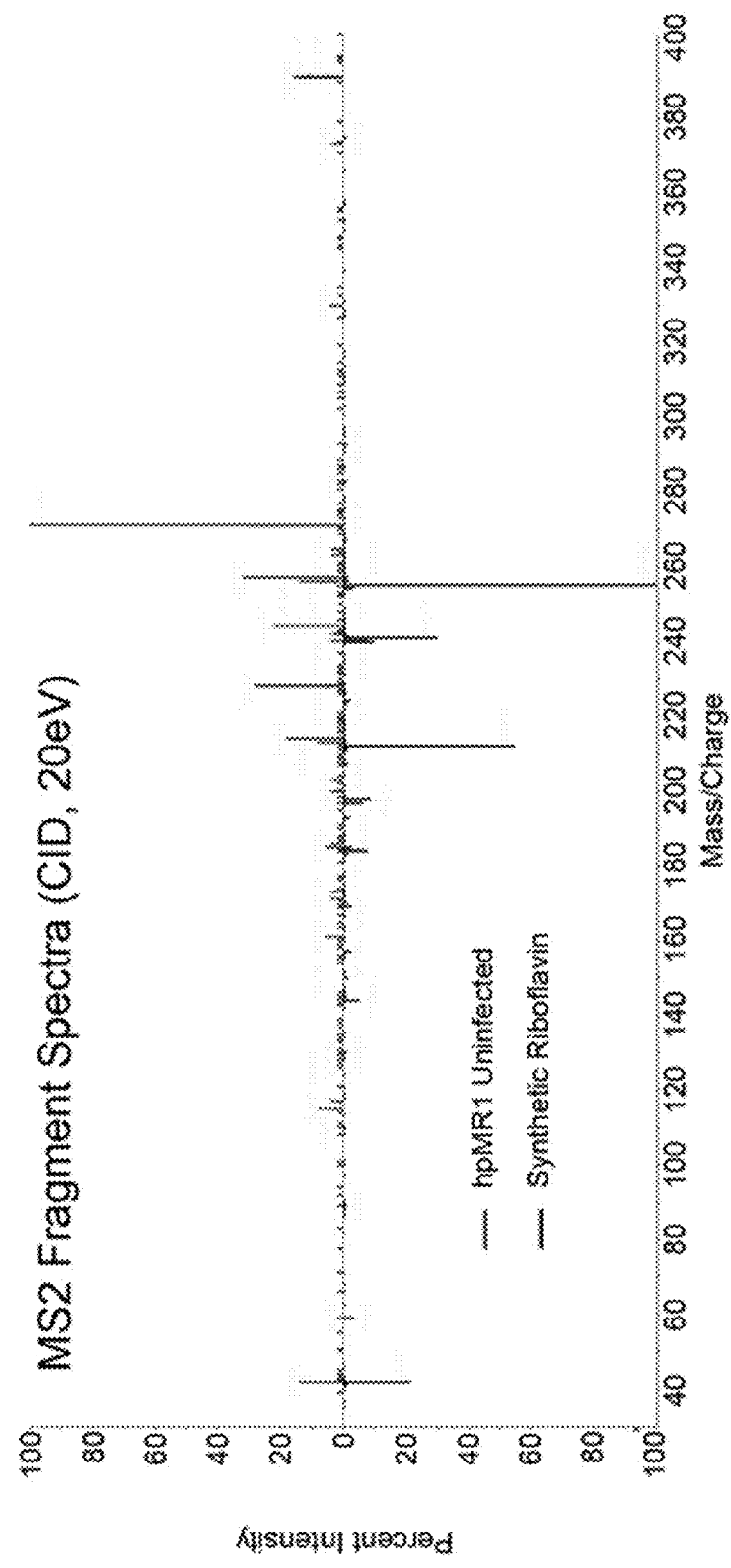
FIG. 14F depicts a MS2 fragment spectra of the precursor ion in indicated sample. The fragment spectra of synthetic riboflavin is shown as a point of comparison.
Figure 15A:
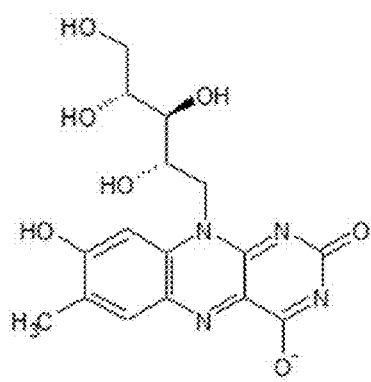
FIG. 15A shows the [M-H]− ion structure, theoretical monoisotopic mass, and chemical formula for 8-demethyl-8-hydroxy-riboflavin.
Figure 15B:
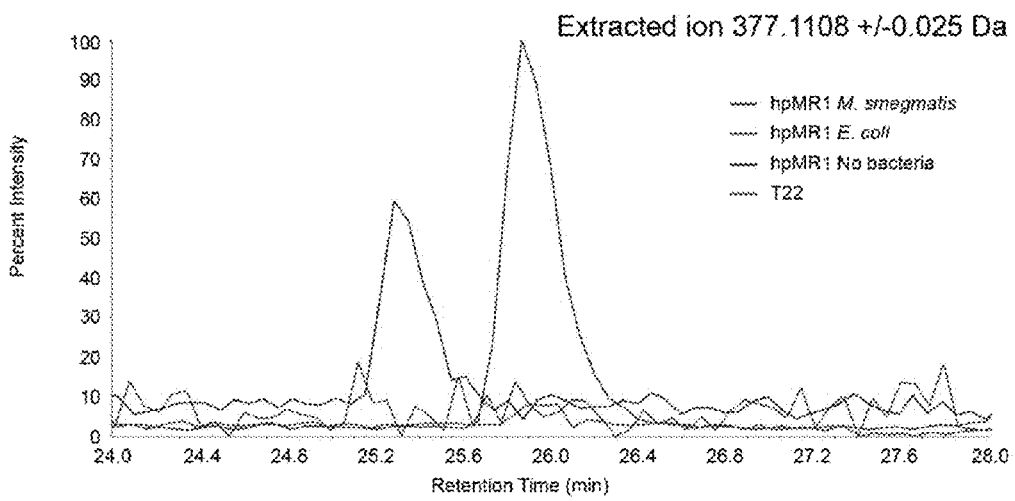
FIG. 15B depicts an extracted ion chromatogram overlay of the theoretical mass of 8-demethyl-8-hydroxy-riboflavin in hpMR1+MS (blue), hpMR1+EC (red), hpMR1-bac (purple), or T22 (green).
Figure 15C:
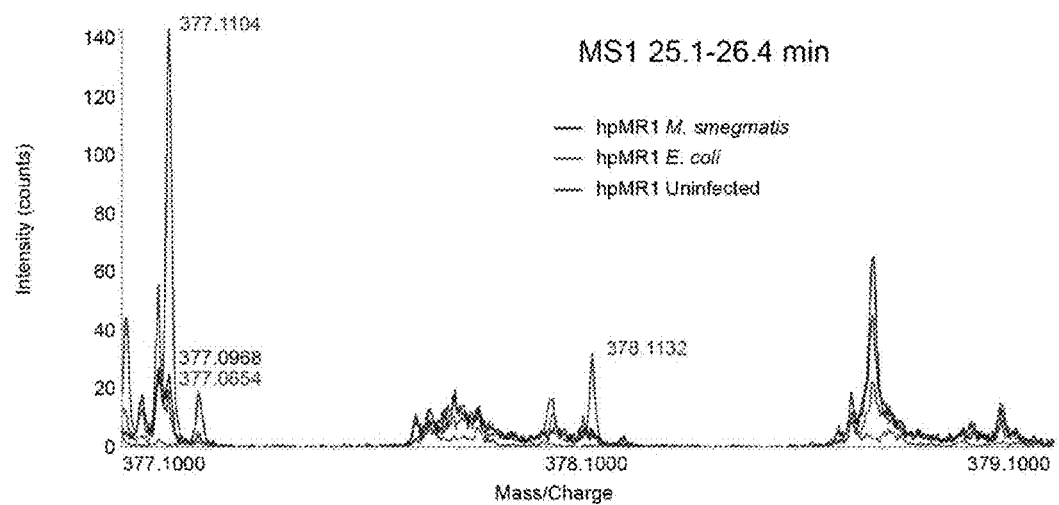
FIG. 15C depicts a MS1 survey spectra overlay of the relevant ion over the indicated retention time range for each indicated sample. Observed m/z for the ion and the respective +1 isotope are labeled and color coded to match the sample trace color.
Figure 15D:
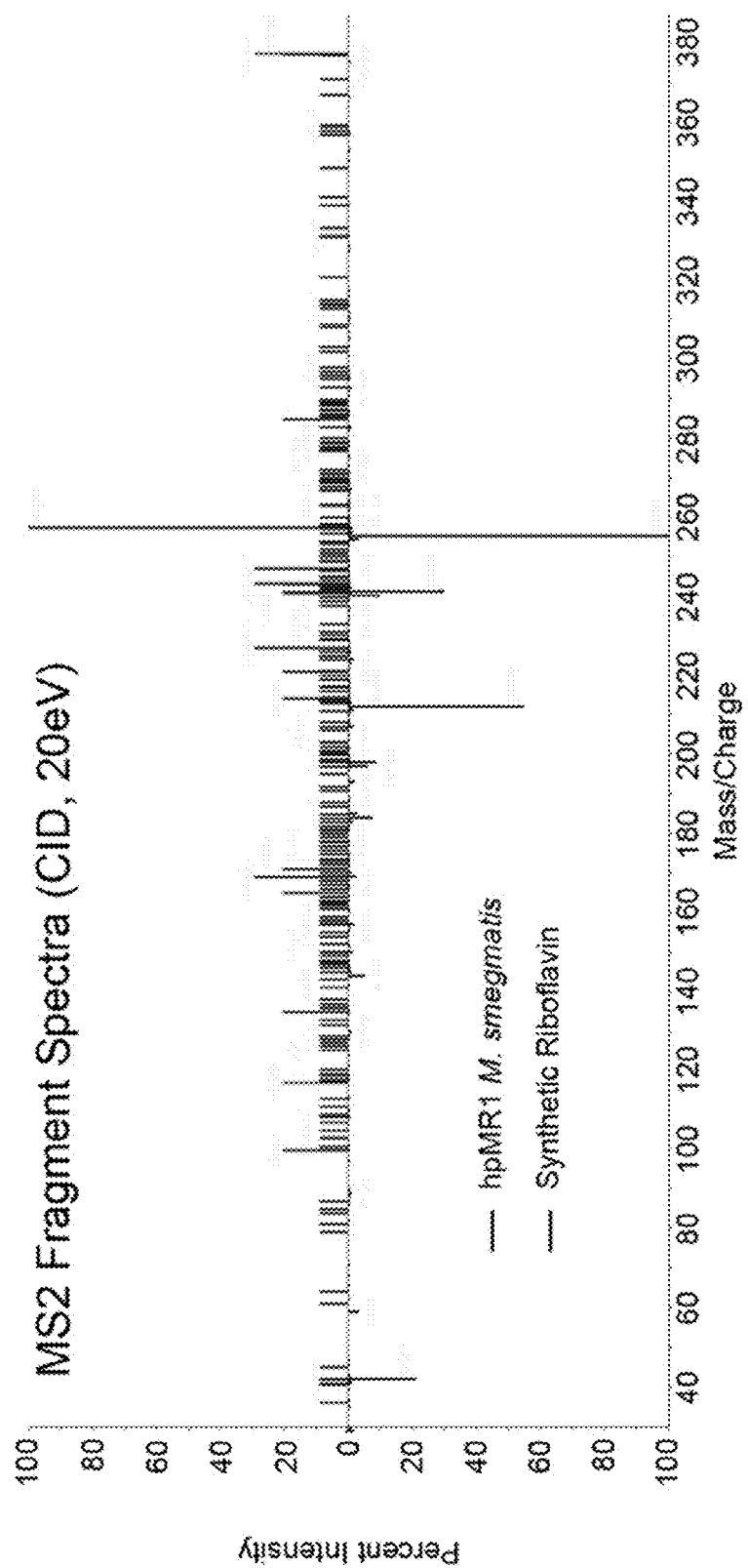
FIG. 15D depicts a MS2 fragment spectra of the precursor ion in indicated sample. The fragment spectra of synthetic riboflavin is shown as a point of comparison.
Figure 15E:
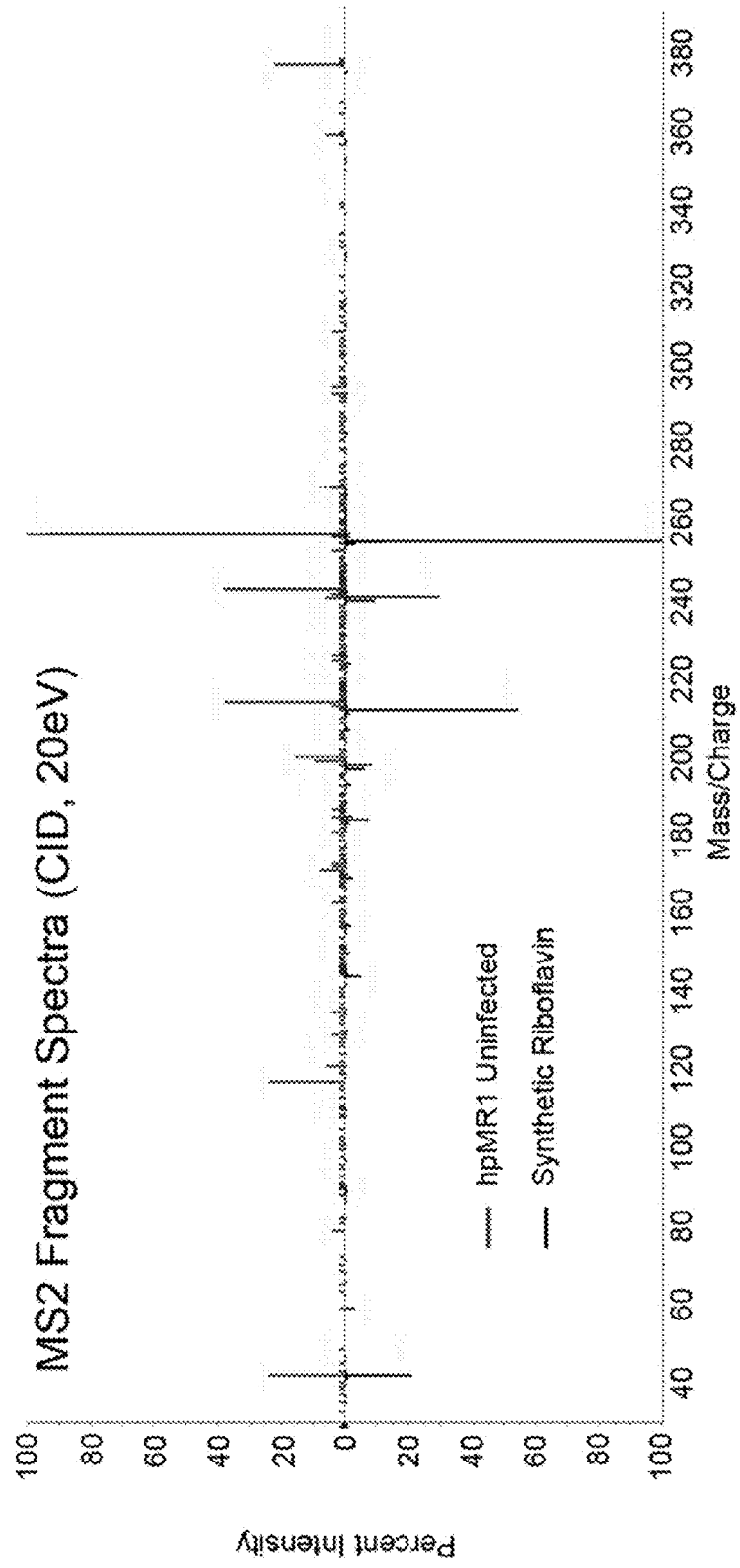
FIG. 15E depicts a MS2 fragment spectra of the precursor ion in indicated sample. The fragment spectra of synthetic riboflavin is shown as a point of comparison.
Figure 16A:
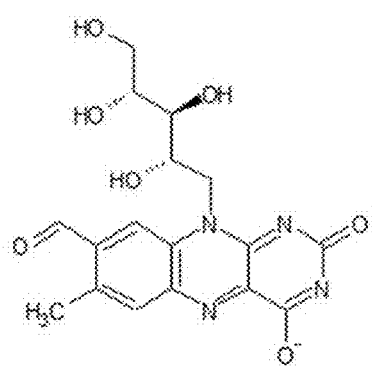
FIG. 16A shows the [M-H]− ion structure, theoretical monoisotopic mass, and chemical formula for 8-demethyl-8-formyl riboflavin.
Figure 16B:
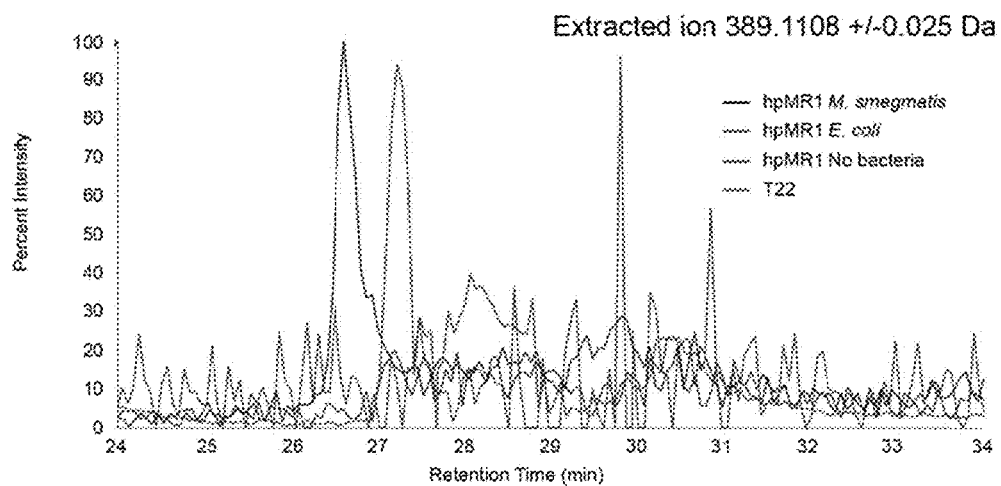
FIG. 16B depicts an extracted ion chromatogram overlay of the theoretical mass of 8-demethyl-8-formyl riboflavin in hpMR1+MS (blue), hpMR1+EC (red), hpMR1-bac (purple), or T22 (green).
Figure 16C:
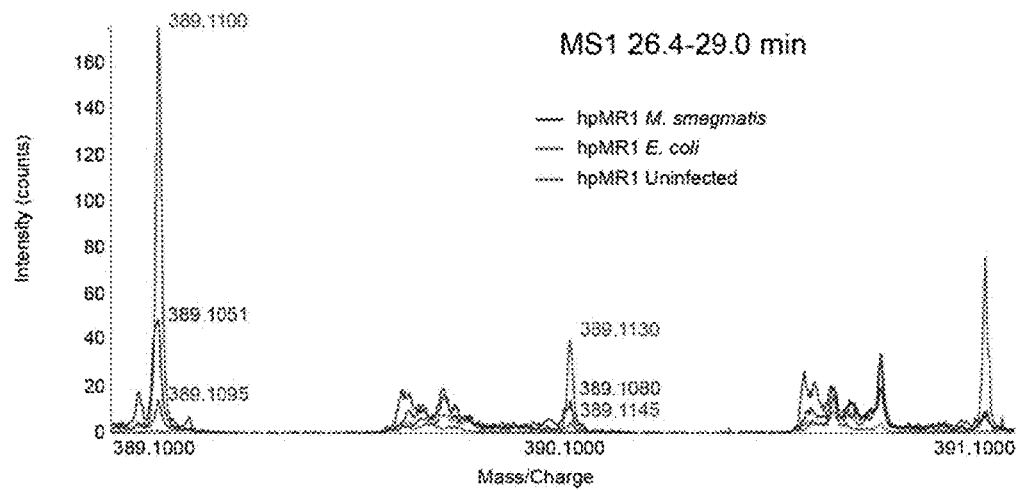
FIG. 16C depicts a MS1 survey spectra overlay of the relevant ion over the indicated retention time range for each indicated sample. Observed m/z for the ion and the respective +1 isotope are labeled and color coded to match the sample trace color.
Figure 16D:
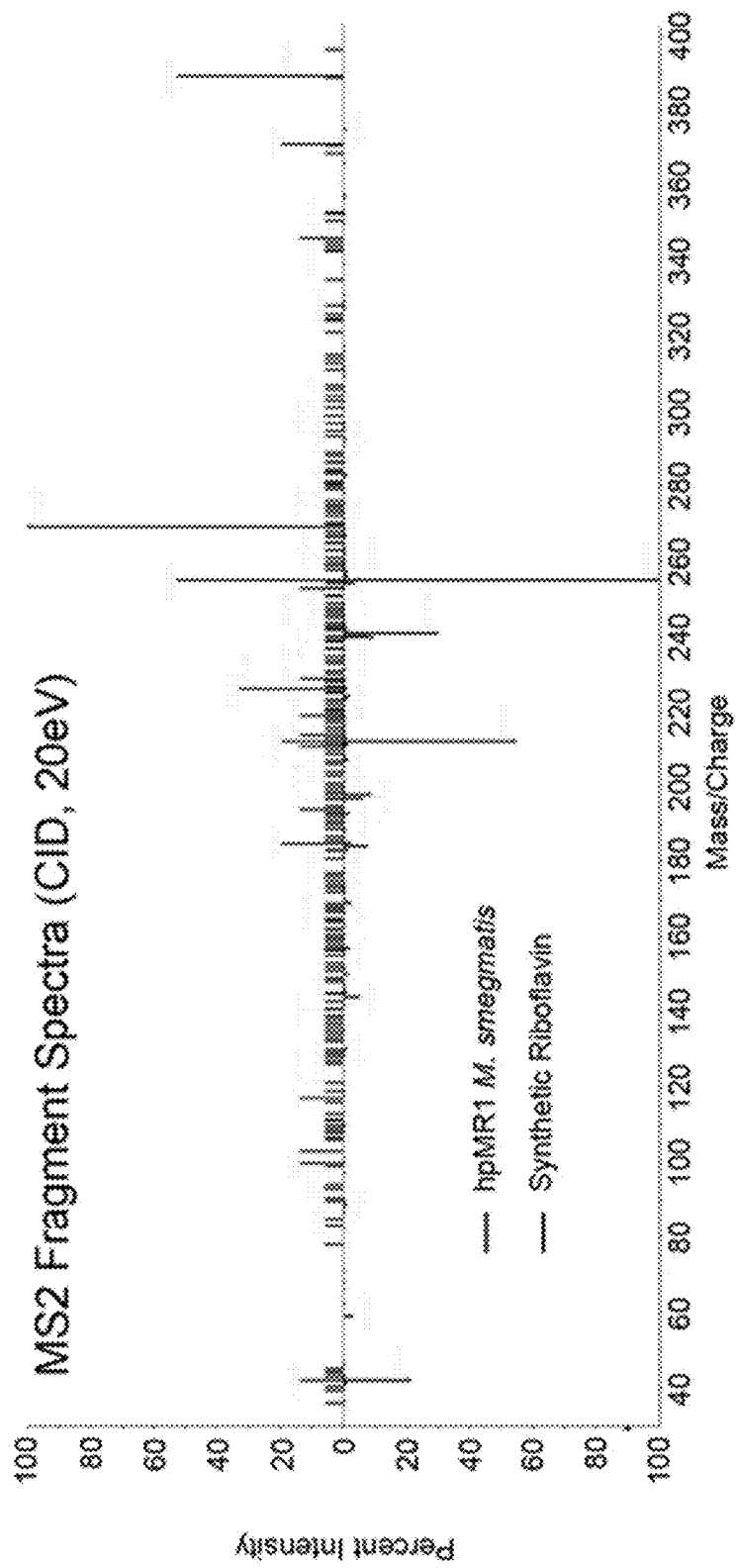
FIG. 16D depicts a MS2 fragment spectra of the precursor ion in indicated sample.
Figure 16E:
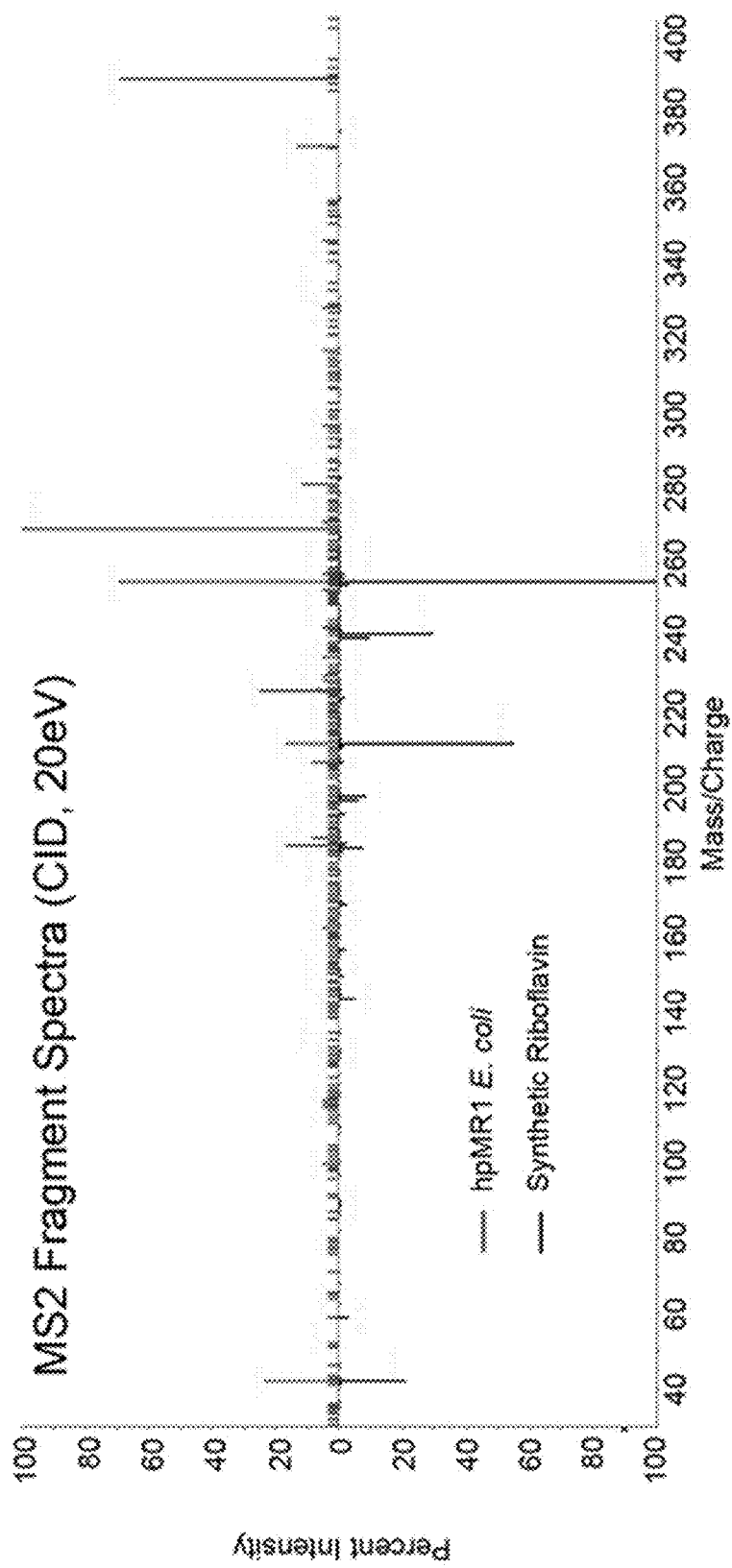
FIG. 16E depicts a MS2 fragment spectra of the precursor ion in indicated sample.
Figure 17A:
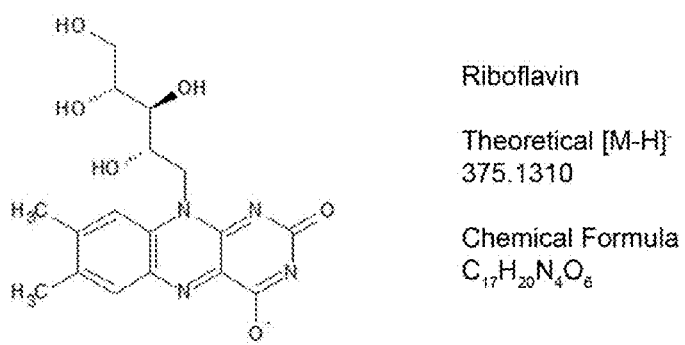
FIG. 17A shows the [M-H]− ion structure, theoretical monoisotopic mass, and chemical formula for riboflavin.
Figure 17B:
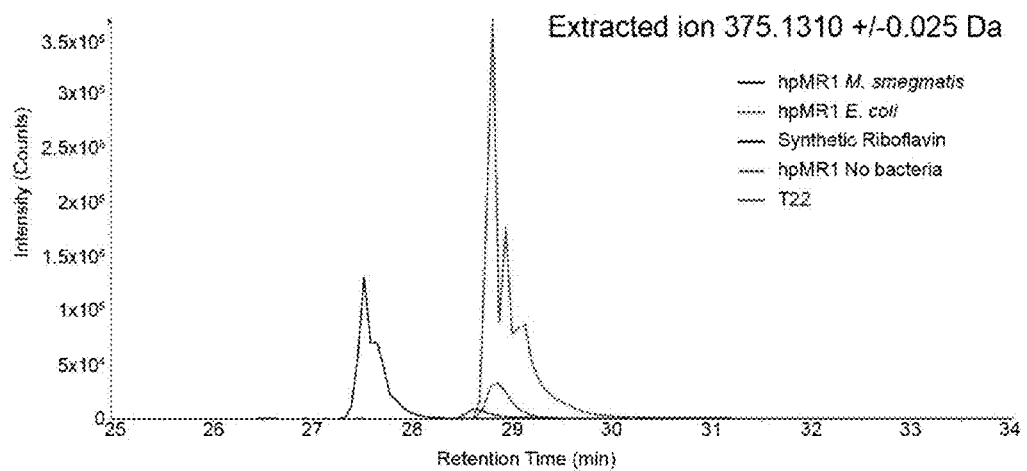
FIG. 17B depicts an extracted ion chromatogram overlay of the theoretical mass of riboflavin in hpMR1+MS (blue), hpMR1+EC (red), hpMR1-bac (purple), T22 (green), or synthetic riboflavin (black).
Figure 17C:
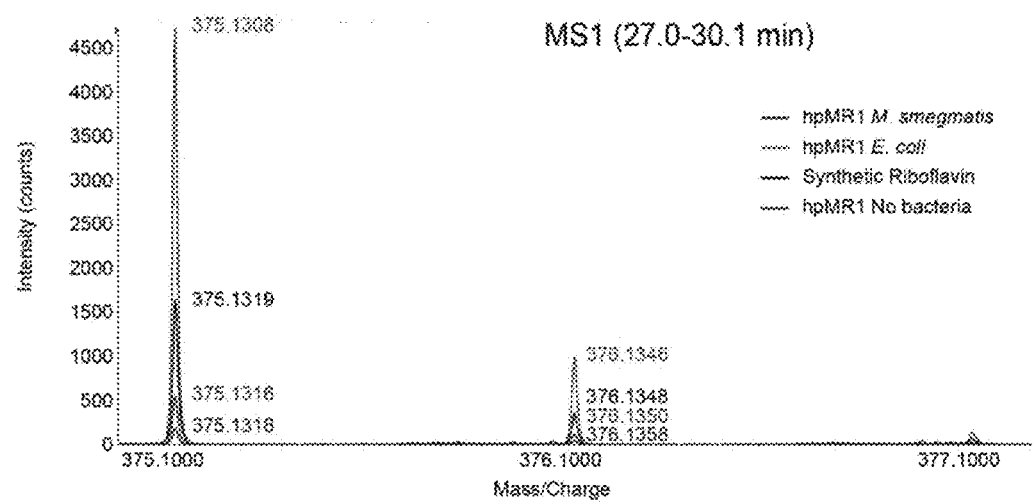
FIG. 17C depicts a MS1 survey spectra overlay of the relevant ion over the indicated retention time range for each indicated sample. Observed m/z for the ion and the respective +1 isotope are labeled and color coded to match the sample trace color.
Figure 17D:
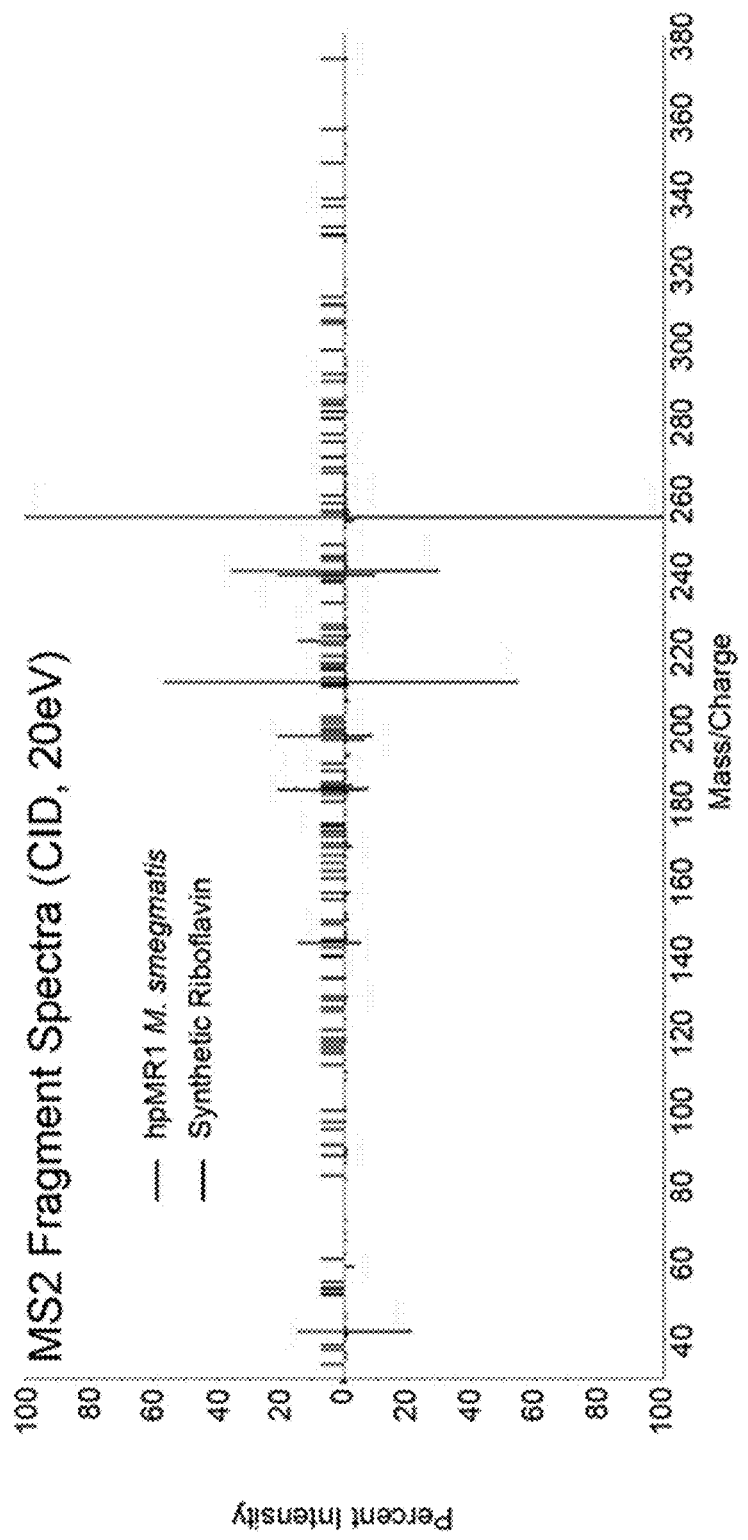
FIG. 17D depicts a MS2 fragment spectra of the precursor ion in indicated sample.
Figure 17E:
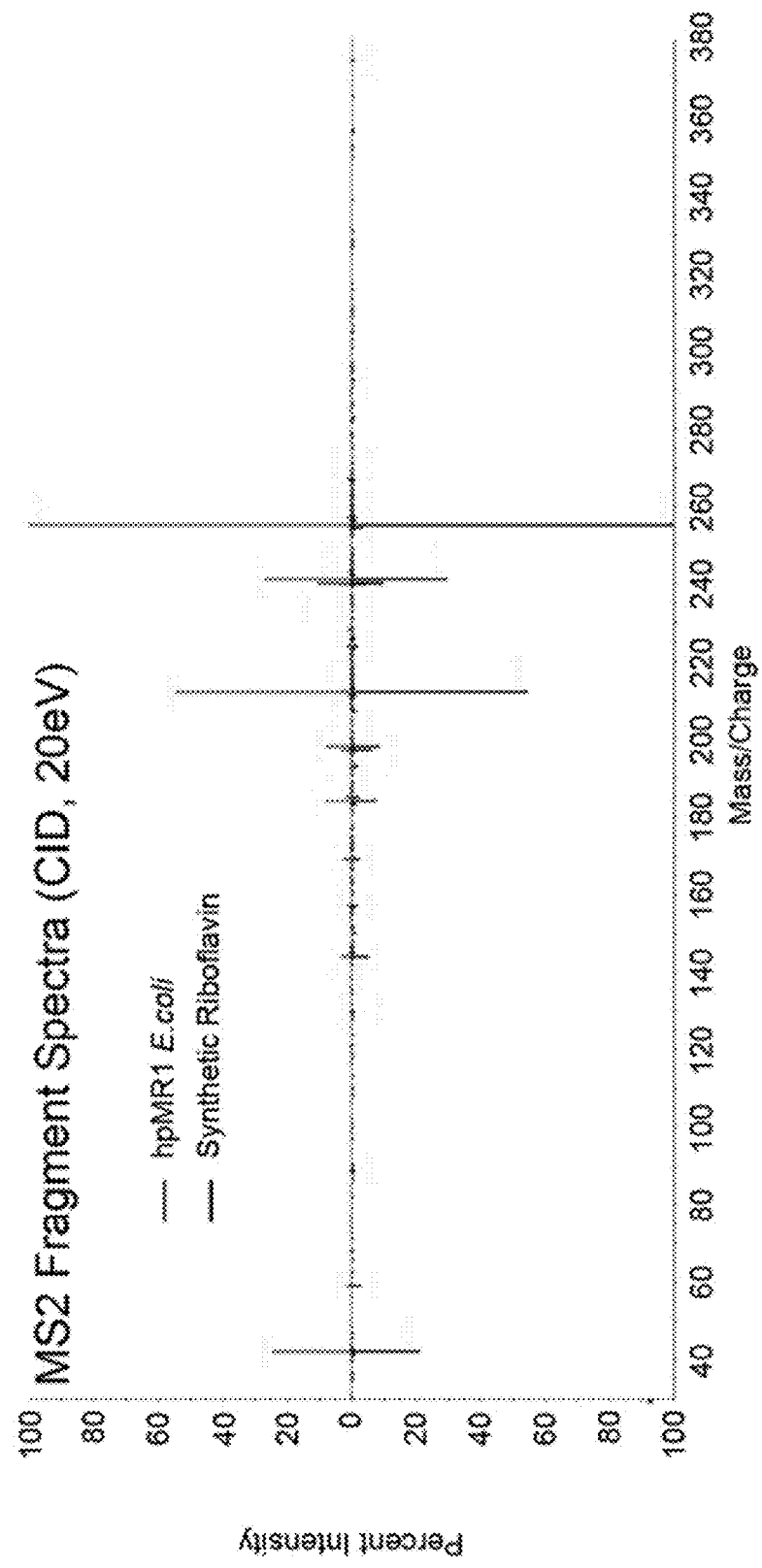
FIG. 17E depicts a MS2 fragment spectra of the precursor ion in indicated sample.
Figure 17F:
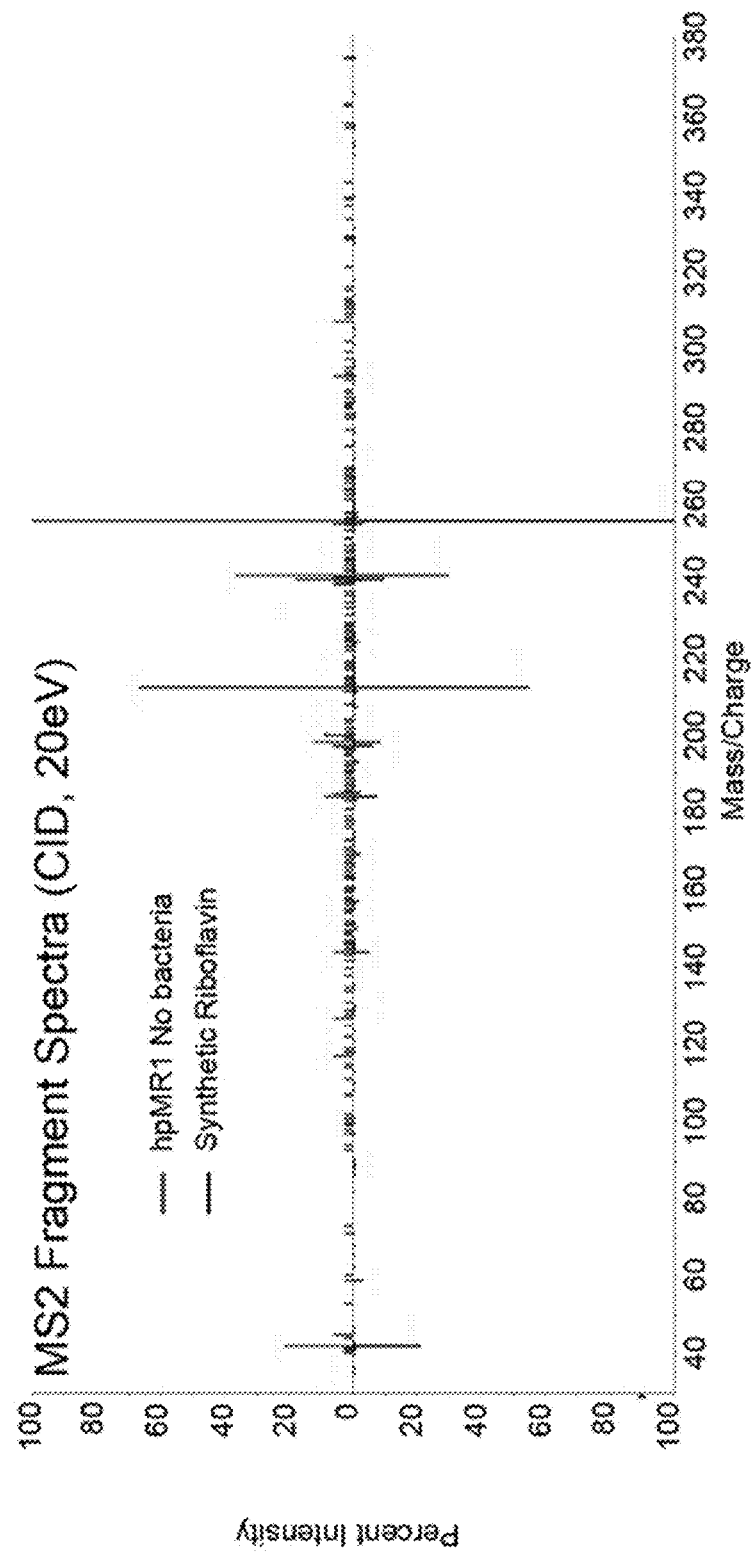
FIG. 17F depicts a MS2 fragment spectra of the precursor ion in indicated sample.
Figure 18A:
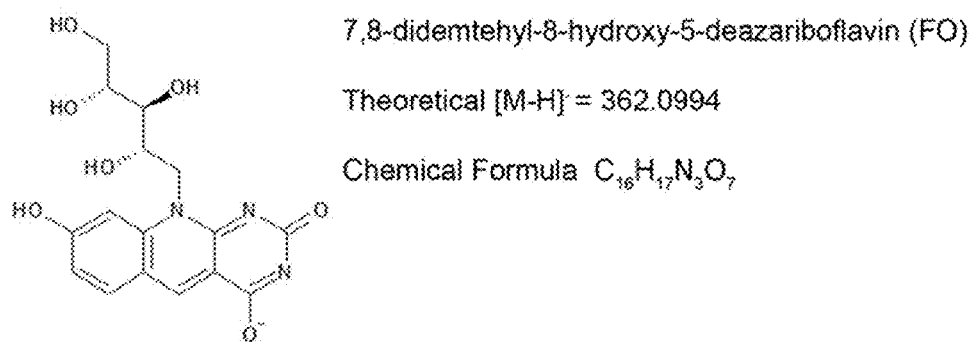
FIG. 18A shows the [M-H]− ion structure, theoretical monoisotopic mass, and chemical formula for 7,8-didemethyl-8-hydroxy-5-deazariboflavin (FO).
Figure 18B:
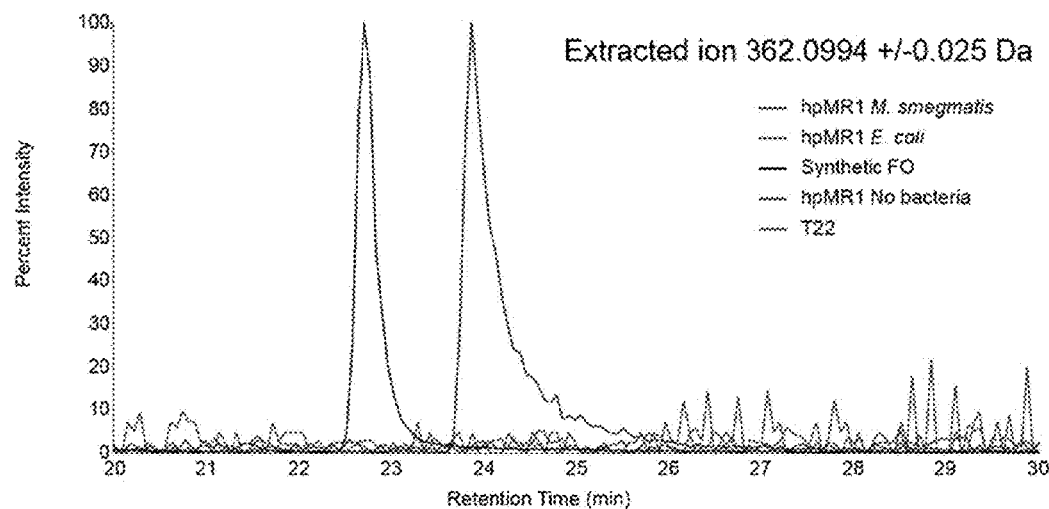
FIG. 18B depicts an extracted ion chromatogram overlay of the theoretical mass of FO in hpMR1+MS (blue), hpMR1+EC (red), hpMR1-bac (purple), T22 (green), or synthetic FO (black).
Figure 18C:
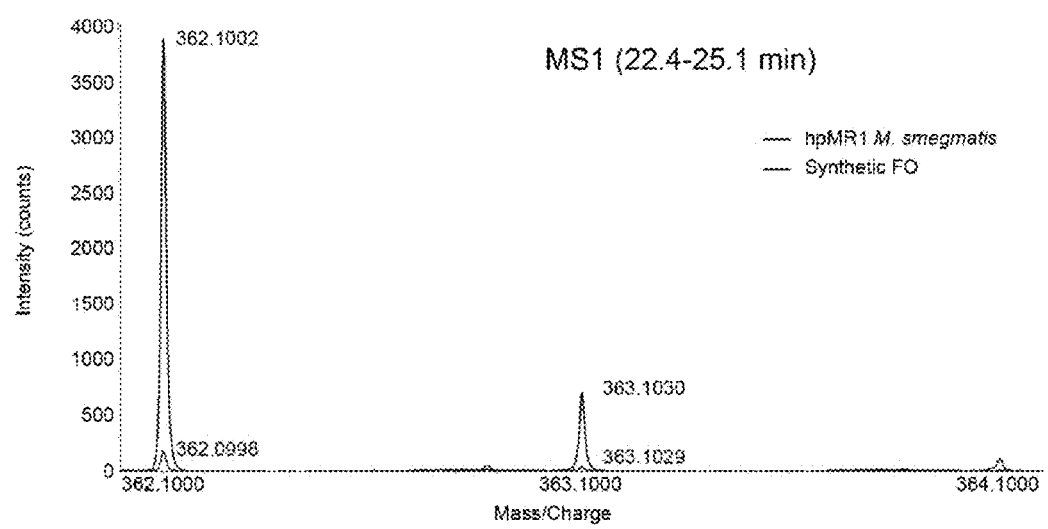
FIG. 18C depicts a MS1 survey spectra overlay of the relevant ion over the indicated retention time range for each indicated sample. Observed m/z for the ion and the respective +1 isotope are labeled and color coded to match the sample trace color.
Figure 18D:
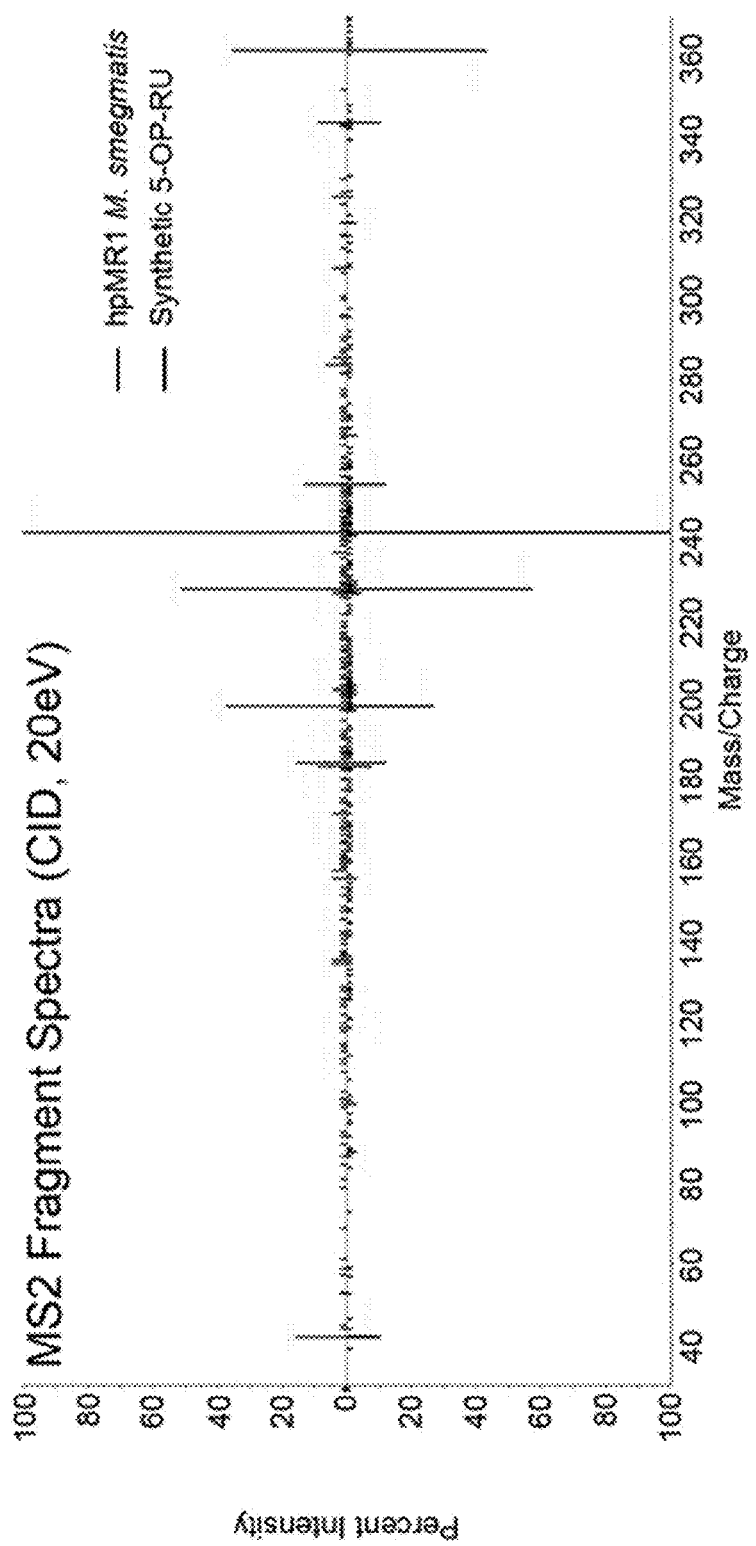
FIG. 18D depicts a MS2 fragment spectra of the precursor ion in indicated sample.
Figure 19A:
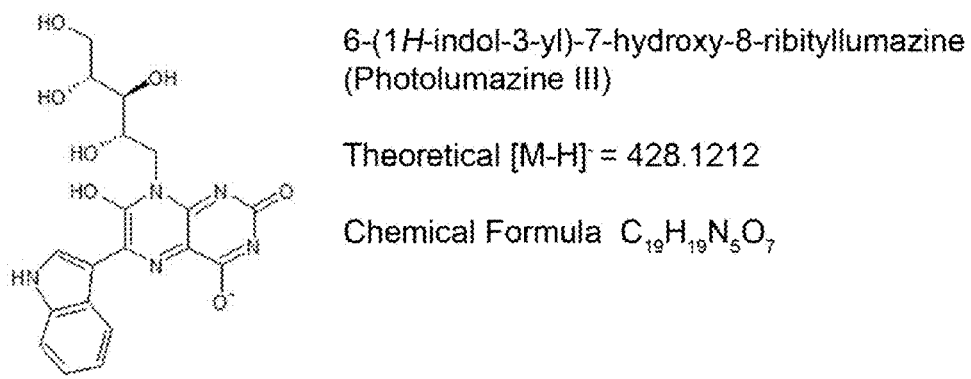
FIG. 19A shows the [M-H]− ion structure, theoretical monoisotopic mass, and chemical formula for 6-(1H-indol-3-yl)-7-hydroxy-8-ribityllumazine (photolumazine III, PLIII).
Figure 19B:
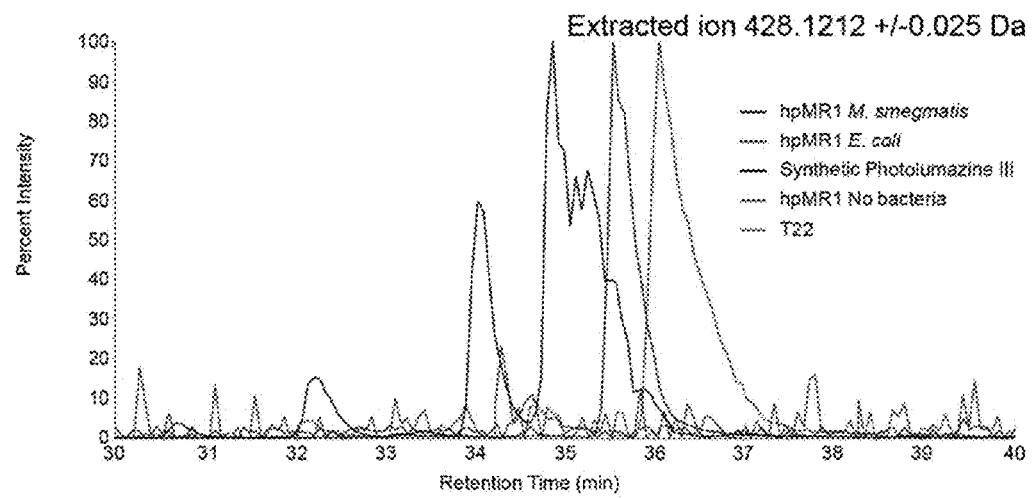
FIG. 19B depicts an extracted ion chromatogram overlay of the theoretical mass of PLIII in hpMR1+MS (blue), hpMR1+EC (red), hpMR1-bac (purple), T22 (green), or synthetic PLIII (black).
Figure 19C:
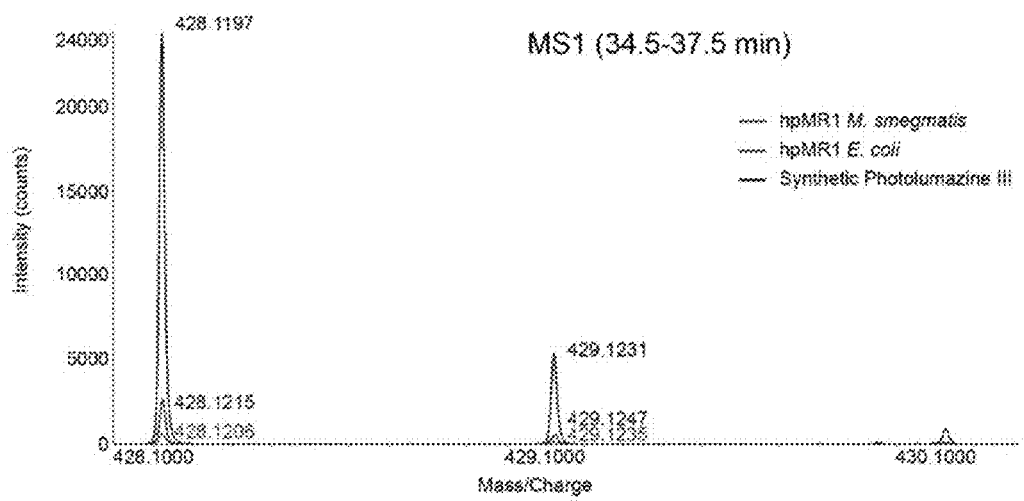
FIG. 19C depicts a MS1 survey spectra overlay of the relevant ion over the indicated retention time range for each indicated sample. Observed m/z for the ion and the respective +1 isotope are labeled and color coded to match the sample trace color.
Figure 19D:
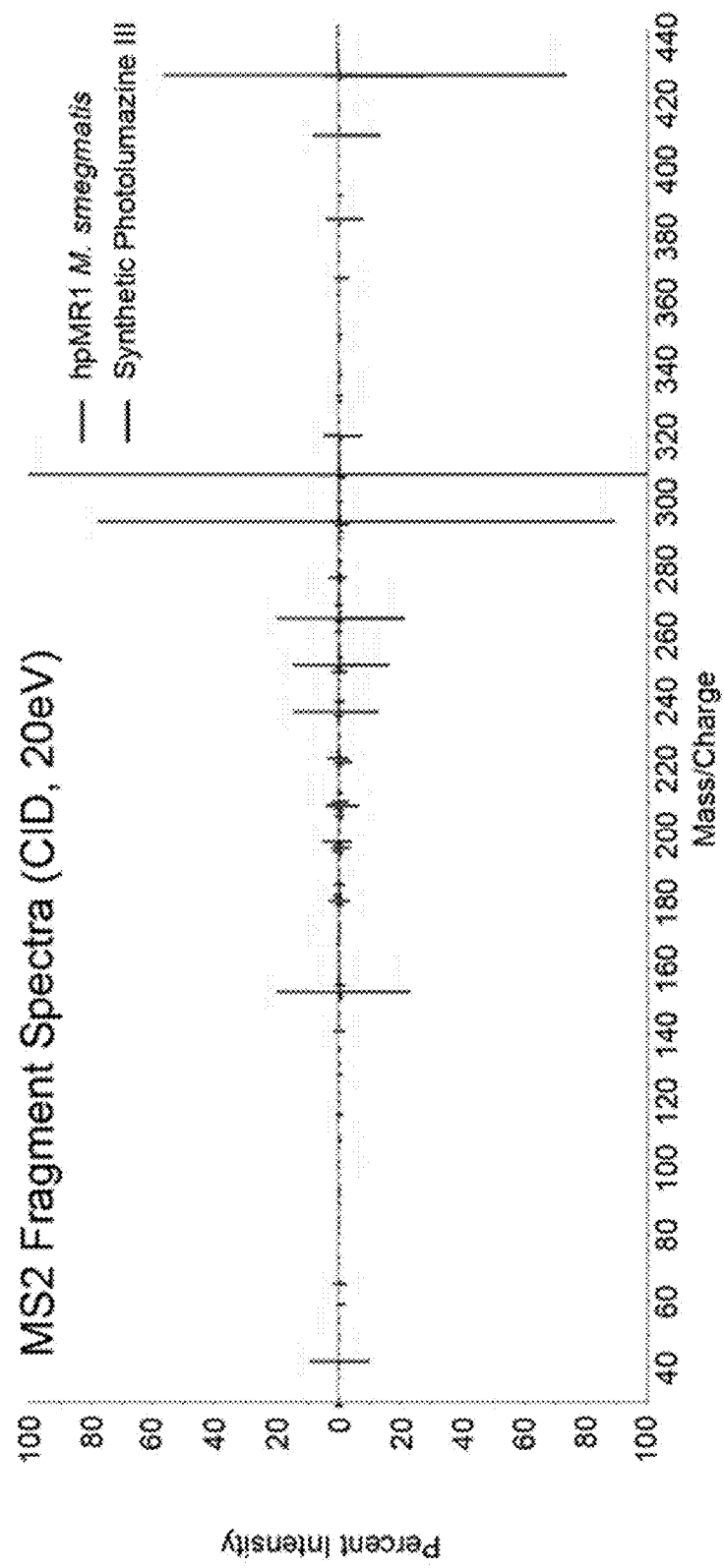
FIG. 19D depicts a MS2 fragment spectra of the precursor ion in indicated sample.
Figure 19E:
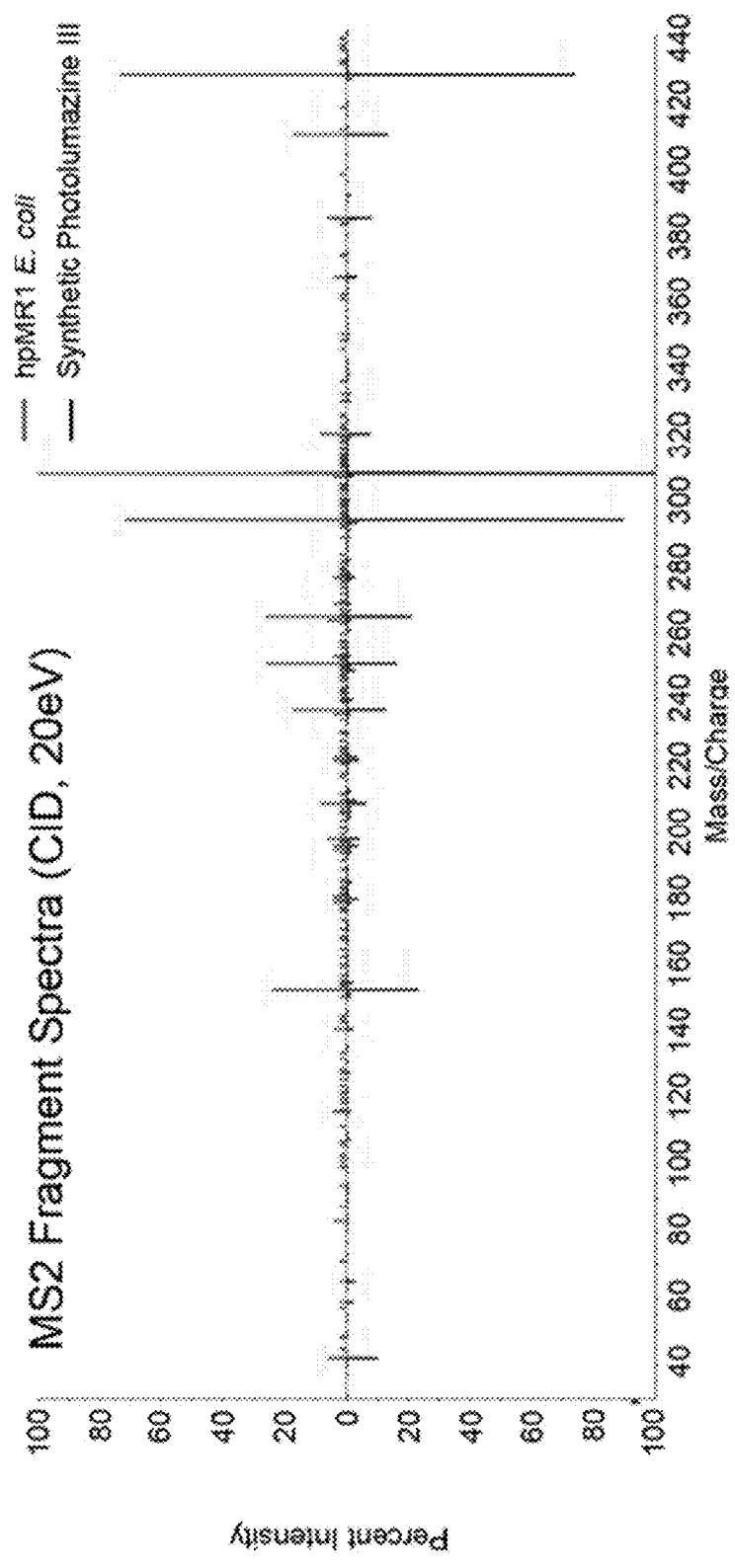
FIG. 19E depicts a MS2 fragment spectra of the precursor ion in indicated sample.
Figure 20A:
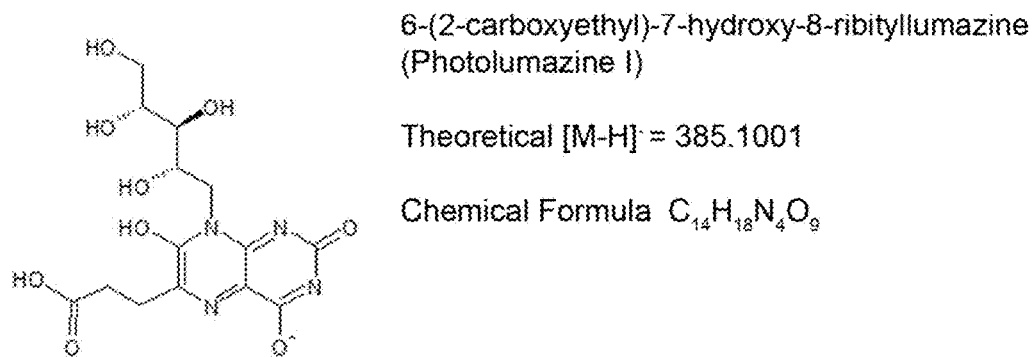
FIG. 20A shows the [M-H]− ion structure, theoretical monoisotopic mass, and chemical formula for 6-(2-carboxyethyl)-7-hydroxy-8-ribityllumazine (photolumazine I, PLI).
Figure 20B:
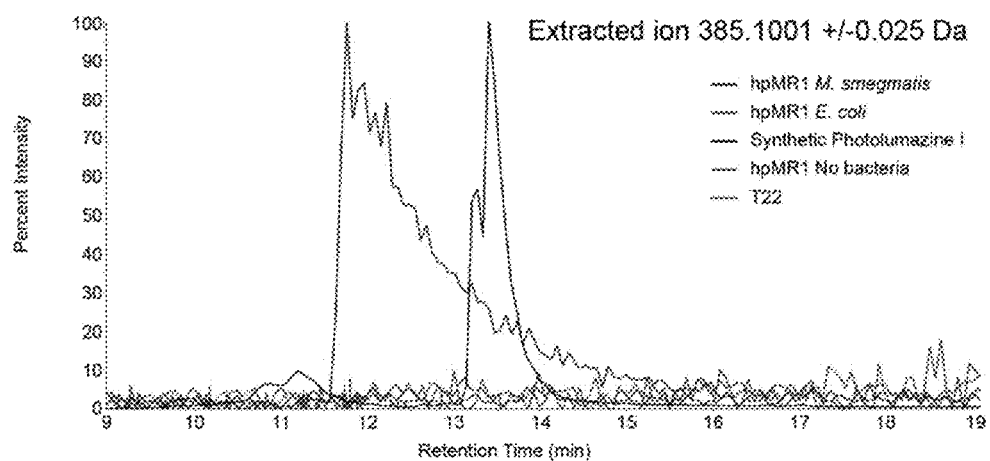
FIG. 20B depicts an extracted ion chromatogram overlay of the theoretical mass of PLI in hpMR1+MS (blue), hpMR1+EC (red), hpMR1-bac (purple), T22 (green), or synthetic PLI (black).
Figure 20C:
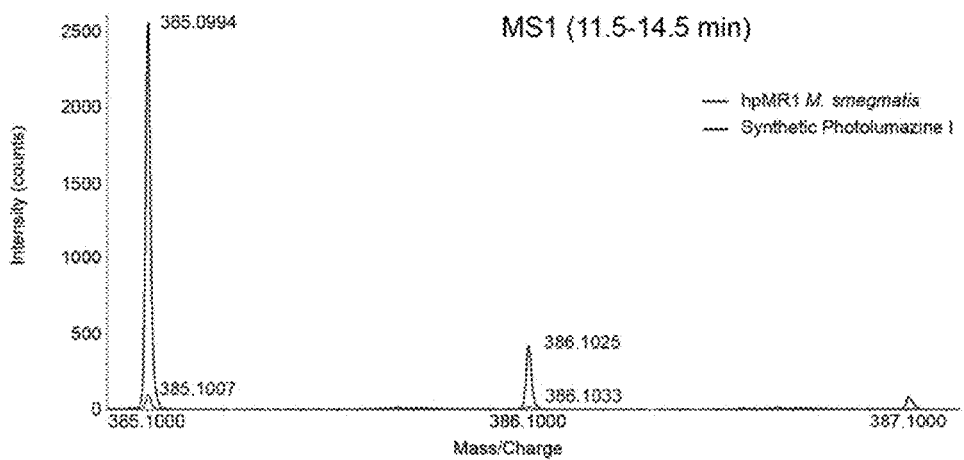
FIG. 20C depicts a MS1 survey spectra overlay of the relevant ion over the indicated retention time range for each indicated sample. Observed m/z for the ion and the respective +1 isotope are labeled and color coded to match the sample trace color.
Figure 20D:
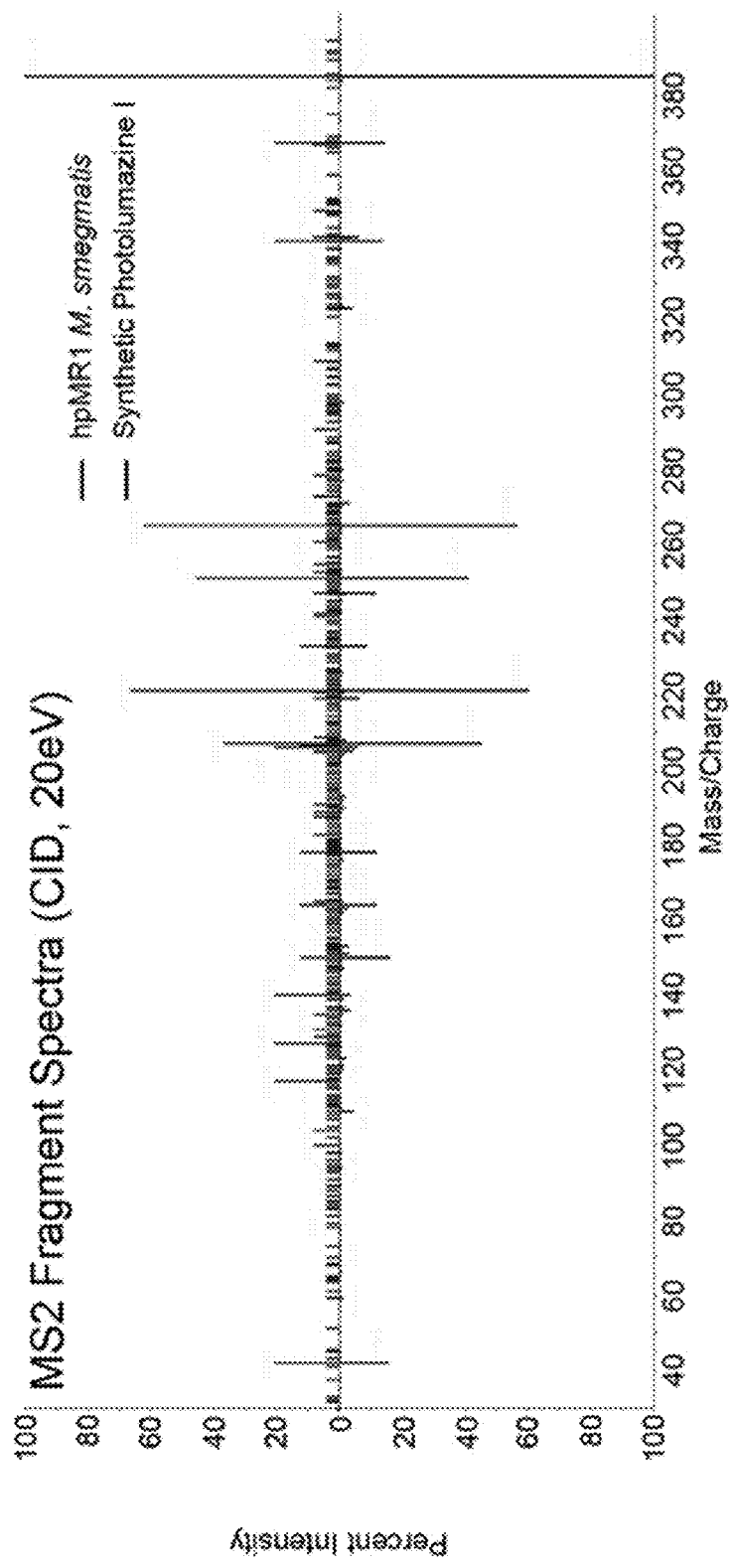
FIG. 20D depicts a MS2 fragment spectra of the precursor ion in indicated sample.

FIG. 12: A) Complete GNPS molecular network including nodes that clustered with no other node. B) Detailed information on the RL-6-Me-7-OH cluster, identifying Ac-RL-6-Me-7-OH. C) The node for 5-OP-RU/rRL-6CH2OH that clustered with no other node. In both B) and C) the average ion m/z and average normalized retention times are shown for each node.

FIGS. 13A, 13B, 13C, 13D: Raw LCMS data for Ac-RL-6-Me-7-OH. A) [M-H]− ion structure, theoretical monoisotopic mass, and chemical formula for Ac-RL-6-Me-7-OH. B) Extracted ion chromatogram overlay of the theoretical mass of Ac-RL-6-Me-7-OH in hpMR1+MS (blue), hpMR1+EC (red), hpMR1-bac (purple), or T22 (green). C) MS1 survey spectra overlay of relevant ion over the indicated retention time range in hpMR1+EC. Observed m/z for the ion and the respective +1 isotope are labeled and color coded to match the sample trace color. D) MS2 fragment spectra of precursor ion in indicated sample. The fragment spectra of synthetic RL-6-Me-7-OH is shown as a point of comparison.

FIGS. 14A, 14B, 14C, 14D, 14E, and 14F. Raw LCMS data for 6-hydroxy-riboflavin. A) [M-H]− ion structure, theoretical monoisotopic mass, and chemical formula for 6-hydroxy-riboflavin. B) Extracted ion chromatogram overlay of the theoretical mass of 6-hydroxy-riboflavin in hpMR1+MS (blue), hpMR1+EC (red), hpMR1-bac (purple), or T22 (green). C) MS1 survey spectra overlay of relevant ion over the indicated retention time range for each indicated sample. Observed m/z for the ion and the respective +1 isotope are labeled and color coded to match the sample trace color. D,E,F) MS2 fragment spectra of precursor ion in indicated sample. The fragment spectra of synthetic riboflavin is shown as a point of comparison.

FIGS. 15A, 15B, 15C, 15D, 15E. Raw LCMS data for 8-demethyl-8-hydroxy-riboflavin. A) [M-H]− ion structure, theoretical monoisotopic mass, and chemical formula for 8-demethyl-8-formyl-riboflavin. B) Extracted ion chromatogram overlay of the theoretical mass of 8-demethyl-8-formyl-riboflavin in hpMR1+MS (blue), hpMR1+EC (red), hpMR1-bac (purple), or T22 (green). C) MS1 survey spectra overlay of relevant ion over the indicated retention time range for each indicated sample. Observed m/z for the ion and the respective +1 isotope are labeled and color coded to match the sample trace color. D,E) MS2 fragment spectra of precursor ion in indicated sample. The fragment spectra of synthetic riboflavin is shown as a point of comparison.

FIGS. 16A, 16B, 16C, 16D, and 16E. Raw LCMS data for 8-demethyl-8-formyl riboflavin. A) [M-H]− ion structure, theoretical monoisotopic mass, and chemical formula for riboflavin. B) Extracted ion chromatogram overlay of the theoretical mass of riboflavin in hpMR1+MS (blue), hpMR1+EC (red), hpMR1-bac (purple), T22 (green), or synthetic riboflavin (black). C) MS1 survey spectra overlay of relevant ion over the indicated retention time range for each indicated sample. Observed m/z for the ion and the respective +1 isotope are labeled and color coded to match the sample trace color. D,E,F) MS2 fragment spectra of precursor ion in indicated sample.

FIGS. 17A, 17B, 17C, 17D, 17E and 17F: Raw LCMS data for riboflavin. A) [M-H]− ion structure, theoretical monoisotopic mass, and chemical formula for riboflavin. B) Extracted ion chromatogram overlay of the theoretical mass of riboflavin in hpMR1+MS (blue), hpMR1+EC (red), hpMR1-bac (purple), T22 (green), or synthetic riboflavin (black). C) MS1 survey spectra overlay of relevant ion over the indicated retention time range for each indicated sample. Observed m/z for the ion and the respective +1 isotope are labeled and color coded to match the sample trace color. D,E,F) MS2 fragment spectra of precursor ion in indicated sample.

FIGS. 18A, 18B, 18C, 18D: Raw LCMS data for 7,8-didemethyl-8-hydroxy-5-deazariboflavin (FO). A) [M-H]− ion structure, theoretical monoisotopic mass, and chemical formula for FO. B) Extracted ion chromatogram overlay of the theoretical mass of FO in hpMR1+MS (blue), hpMR1+EC (red), hpMR1-bac (purple), T22 (green), or synthetic FO (black). C) MS1 survey spectra overlay of relevant ion over the indicated retention time range for each indicated sample. Observed m/z for the ion and the respective +1 isotope are labeled and color coded to match the sample trace color. D) MS2 fragment spectra of precursor ion in indicated sample.

FIGS. 19A, 19B, 19C, 19D, 19E: Raw LCMS data for 6-(1H-indol-3-yl)-7-hydroxy-8-ribityllumazine (photolumazine III, PLIII). A) [M-H]− ion structure, theoretical monoisotopic mass, and chemical formula for photolumazine III. B) Extracted ion chromatogram overlay of the theoretical mass of PLIII in hpMR1+MS (blue), hpMR1+EC (red), hpMR1-bac (purple), T22 (green), or synthetic PLIII (black). C) MS1 survey spectra overlay of relevant ion over the indicated retention time range for each indicated sample. Observed m/z for the ion and the respective +1 isotope are labeled and color coded to match the sample trace color. D,E) MS2 fragment spectra of precursor ion in indicated sample.

FIGS. 20A, 20B, 20C, and 20D. Raw LCMS data for 6-(2-carboxyethyl)-7-hydroxy-8-ribityllumazine (photolumazine I, PLI). A) [M-H]− ion structure, theoretical monoisotopic mass, and chemical formula for PLI. B) Extracted ion chromatogram overlay of the theoretical mass of PLI in hpMR1+MS (blue), hpMR1+EC (red), hpMR1-bac (purple), T22 (green), or synthetic PLI (black). C) MS1 survey spectra overlay of relevant ion over the indicated retention time range for each indicated sample. Observed m/z for the ion and the respective +1 isotope are labeled and color coded to match the sample trace color. D) MS2 fragment spectra of precursor ion in indicated sample.

Figure 21A:
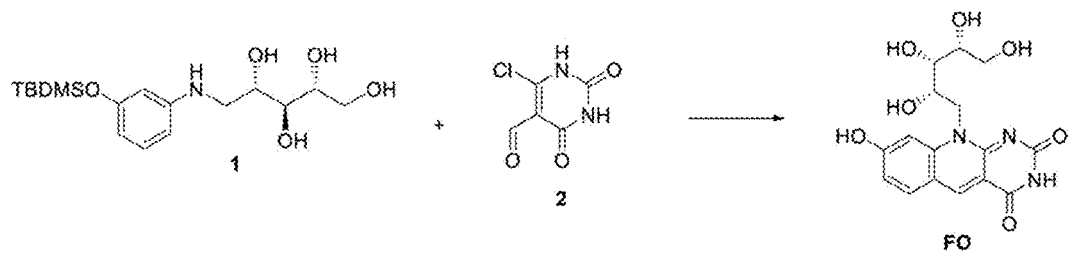
FIG. 21A depicts chemical synthesis of MR1 ligand 7,8-didemethyl-8-hydroxy-5-deazariboflavin (FO)
Figure 21B:
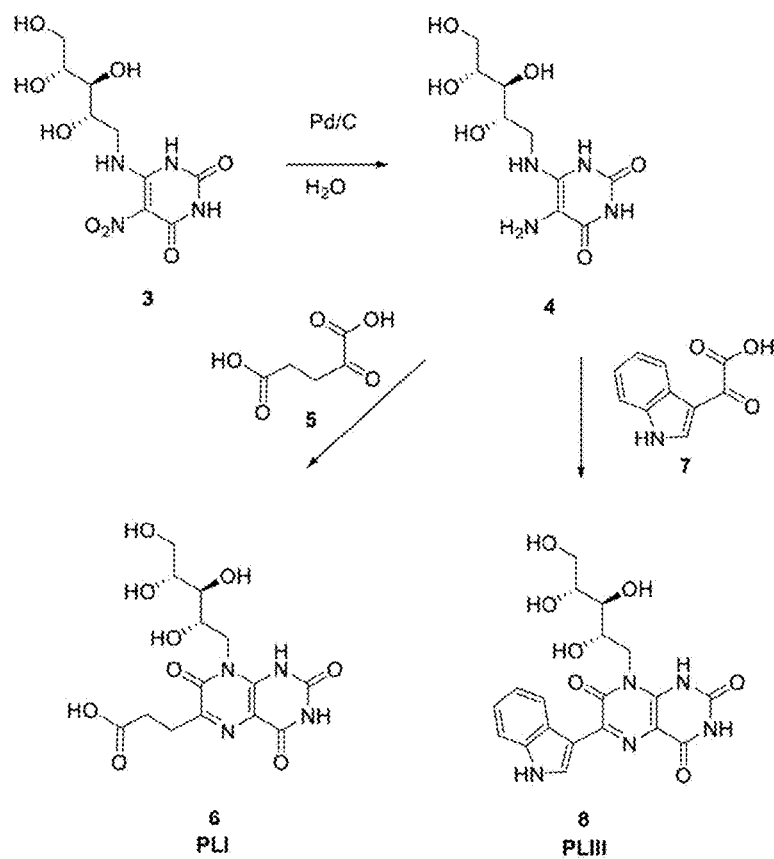
FIG. 21B depicts chemical synthesis of MR1 ligands 6-(1H-indol-3-yl)-7-hydroxy-8-ribityllumazine (PLI I) and 6-(2-carboxyethyl)-7-hydroxy-8-ribityllumazine (PLI).

FIGS. 21A and 21B. Chemical synthesis of MR1 ligands: A) 7,8-didemethyl-8-hydroxy-5-deazariboflavin (FO). B) 6-(1H-indol-3-yl)-7-hydroxy-8-ribityllumazine (PLIII) and 6-(2-carboxyethyl)-7-hydroxy-8-ribityllumazine (PLI).

Figure 22:
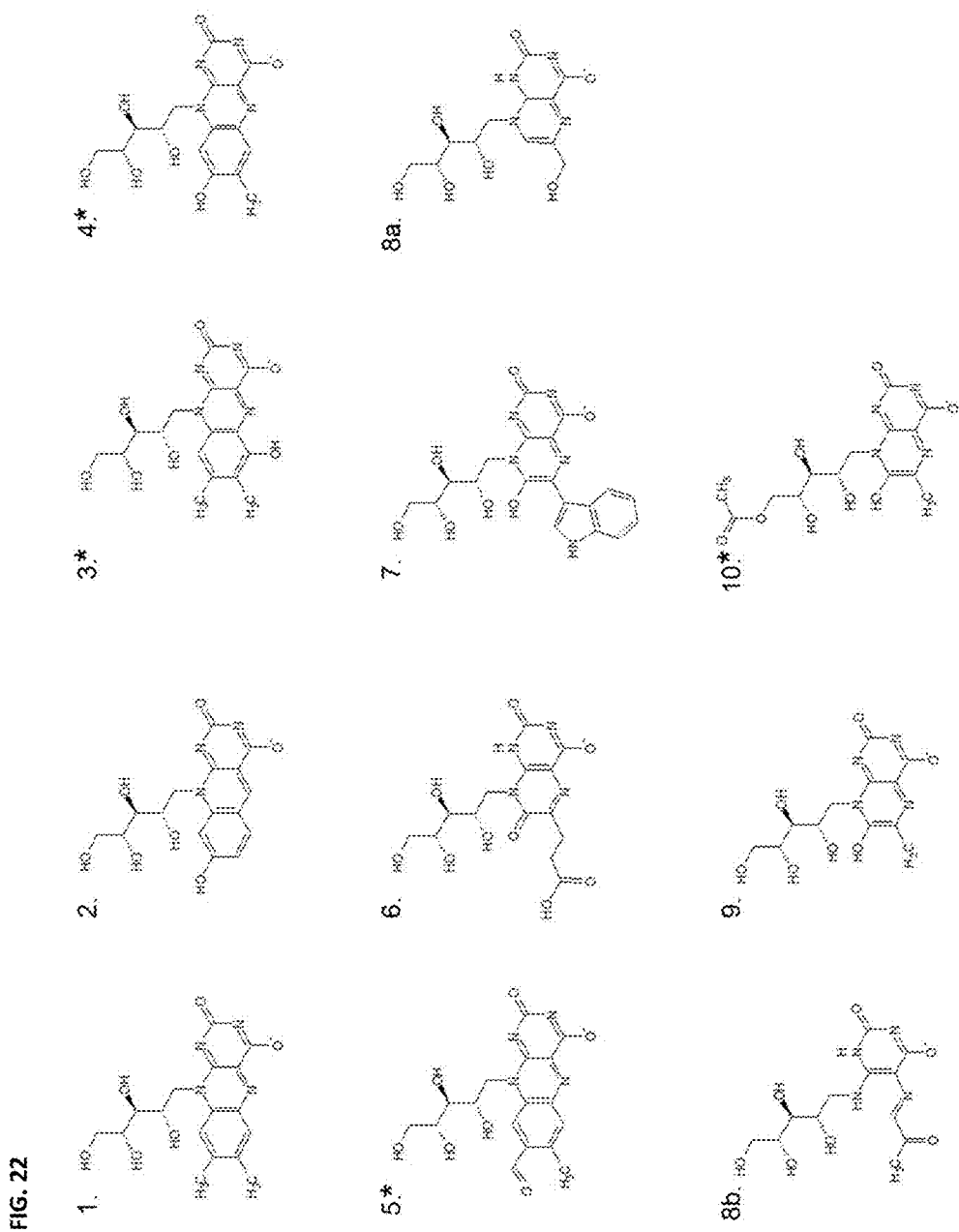
FIG. 22 depicts ion structures of identified or proposed compounds disclosed herein. Proposed and not confirmed structures are denoted with an asterisk. The structures are numbered corresponding to the 'Structure Number' column of Table S3.

FIG. 22. Ion structures of identified or proposed compounds in the study. Proposed and not confirmed structures are denoted with an asterisk. The structures are numbered corresponding to the 'Structure Number' column of Table S3.

The invention claimed is:

1. A method of treating a respiratory infection of *Mycobacterium tuberculosis* or *Streptococcus pyogenes* in a human subject, the method comprising administering to the human subject in need thereof a pharmaceutically effective amount of a compound selected from Formula 1b, Formula 2b, and Formula 3b, or a pharmaceutically acceptable salt thereof:

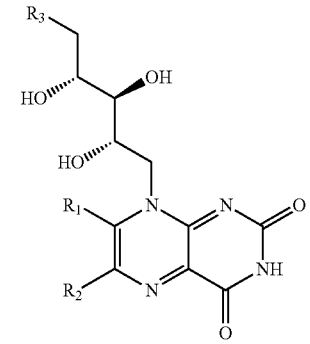

1b

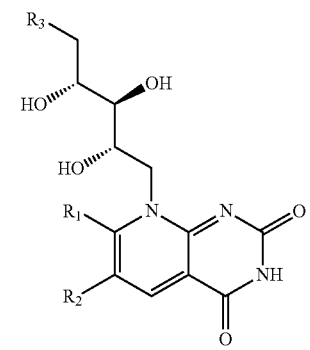

2b

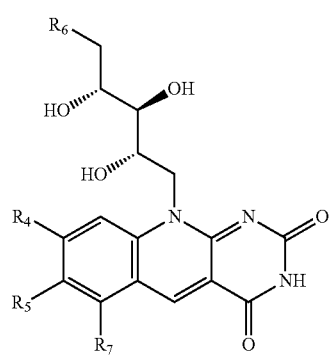

3b wherein, in each appearance:

$R_1$ is independently selected from H, OH, $C_1$-$C_3$ alkyl, and —CH=O;

$R_2$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$;

$R_3$ is selected from OH and —O(C=O)—$C_1$-$C_3$ alkyl;

$R_4$ is independently selected from H, OH, $C_1$-$C_3$ alkyl, and —CH=O;

$R_5$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$;

$R_6$ is selected from OH and —O(C=O)-$C_1$-$C_3$ alkyl; and $R_7$ is H or OH.

2. The method of claim 1, wherein the compound is of Formula 1b, or a pharmaceutically acceptable salt thereof:

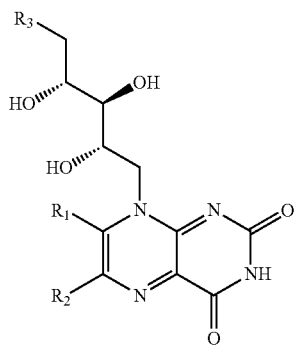

1b wherein $R_1$ is independently selected from H, OH, $C_1$-$C_3$ alkyl, and —CH=O;

$R_2$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$; and $R_3$ is selected from OH and —O(C=O)-$C_1$-$C_3$ alkyl.

3. The method of claim 1, wherein the compound is selected from the group of:

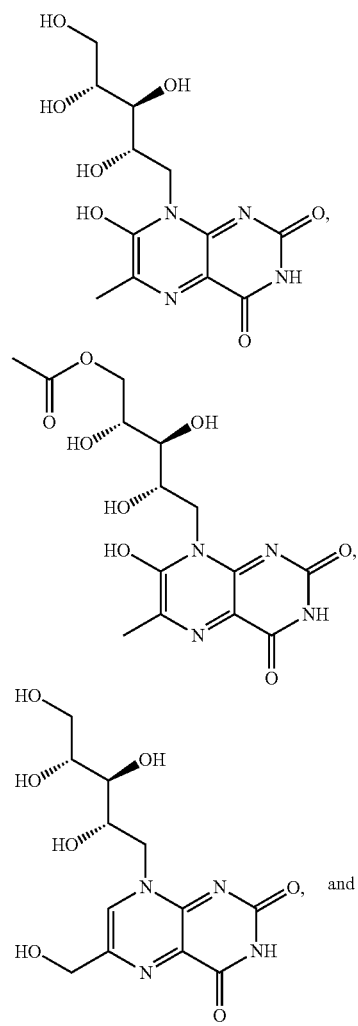

-continued

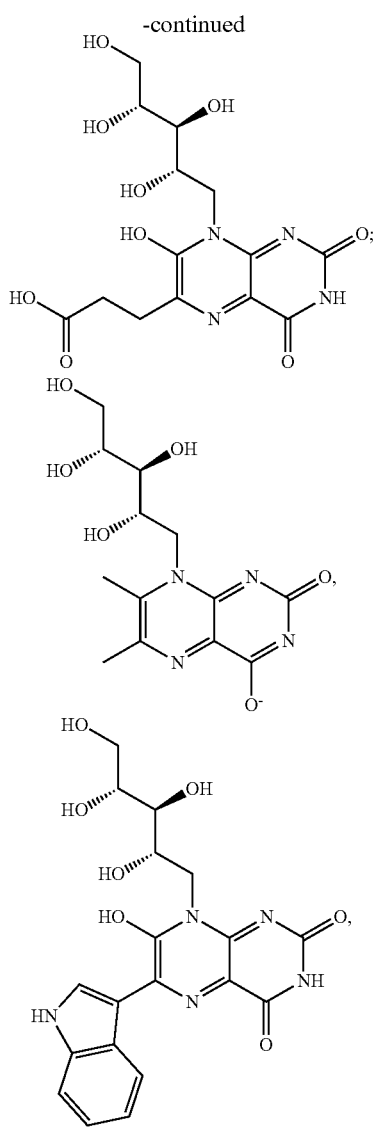

or a pharmaceutically acceptable salt thereof.

4. The method of claim 1, wherein the compound is of Formula 3b, or a pharmaceutically acceptable salt thereof:

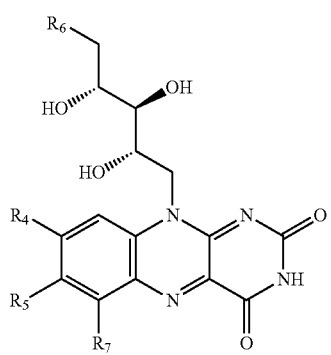

3b wherein $R_4$ is independently selected from H, OH, $C_1$-$C_3$ alkyl, and —CH=O;

$R_5$ is independently selected from H, a 5-10-membered carbocycle, a 5-10-membered heterocycle, and $C_1$-$C_3$ alkyl, wherein the $C_1$-$C_3$ alkyl can be substituted by 1 or 2 substituents selected from OH and $CO_2H$;

$R_6$ is selected from OH and —O(C=O)-$C_1$-$C_3$ alkyl; and $R_7$ is H or OH.

5. The method of claim 1, wherein the compound is selected from the group of:

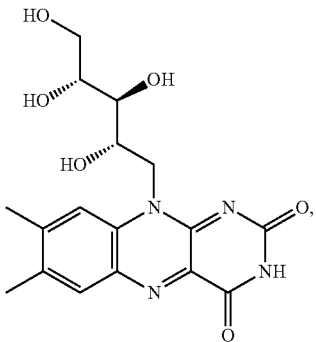

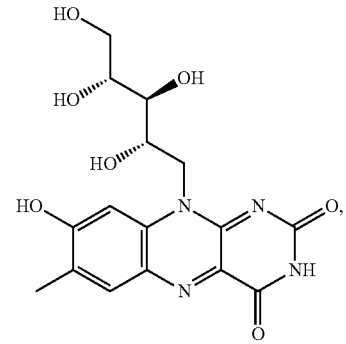

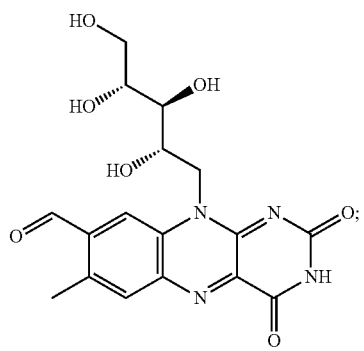

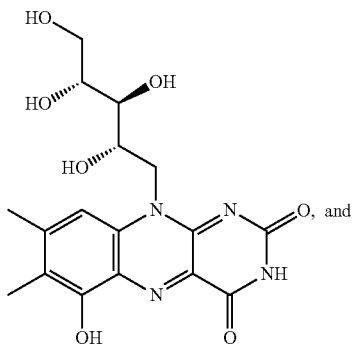

-continued
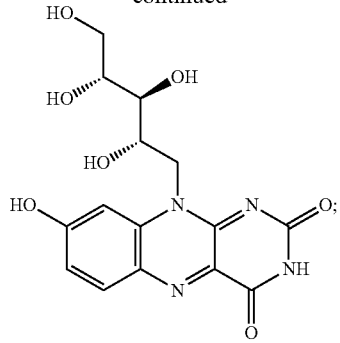
or a pharmaceutically acceptable salt thereof.
6. The method of claim 1, wherein the compound is:
or a pharmaceutically acceptable salt thereof.
7. The method of claim 1, wherein the compound is:
or a pharmaceutically acceptable salt thereof.
* * * * *